US008323931B2

(12) United States Patent
Gudynaite-Savitch et al.

(10) Patent No.: US 8,323,931 B2
(45) Date of Patent: Dec. 4, 2012

(54) HOSTS AND FERMENTATION PROCESSES FOR CELLULASE PRODUCTION

(75) Inventors: Loreta Gudynaite-Savitch, Kanata (CA); Christopher D. Hindle, Gloucester (CA); Theresa C. White, Ottawa (CA)

(73) Assignee: Iogen Energy Corporation, Ottawa, Ontario (CA)

( * ) Notice: Subject to any disclaimer, the term of this patent is extended or adjusted under 35 U.S.C. 154(b) by 363 days.

(21) Appl. No.: 12/611,486

(22) Filed: Nov. 3, 2009

(65) Prior Publication Data
US 2010/0129880 A1 May 27, 2010

Related U.S. Application Data

(60) Provisional application No. 61/110,732, filed on Nov. 3, 2008.

(51) Int. Cl.
C12P 19/14 (2006.01)
C12P 21/06 (2006.01)
C12N 9/42 (2006.01)
C12N 1/00 (2006.01)
C08B 37/00 (2006.01)
D21C 1/00 (2006.01)
C02F 3/34 (2006.01)

(52) U.S. Cl. ...... 435/99; 435/209; 435/69.1; 435/254.1; 435/254.3; 435/254.4; 435/254.6; 435/254.7; 435/274; 435/277; 435/262; 536/23.2; 530/350

(58) Field of Classification Search .................... 435/99, 435/209, 69.1, 254.1, 254.3, 254.6, 254.7, 435/274, 277, 262; 536/23.2; 530/350
See application file for complete search history.

(56) References Cited

U.S. PATENT DOCUMENTS

| 6,177,261 | B1 | 1/2001 | De Graaff et al. |
| 2009/0061486 | A1 | 3/2009 | Edwards et al. |

FOREIGN PATENT DOCUMENTS

| WO | 2008/025165 | 3/2008 |
| WO | 2008/060596 | 5/2008 |
| WO | 2009/026716 | 3/2009 |

OTHER PUBLICATIONS

Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Whisstock et al., Prediction of protein function from protein sequence. Q. Rev. Biophysics., 2003, vol. 36 (3): 307-340.*
Ahmed et al., "Induction of Xylanase and Cellulase Genes from Trichoderma harzianum with Different Carbon Sources", Pakistan Journal of Biological Sciences, vol. 6, No. 22 (2003) 1912-16.
Aro et al., "Transcriptional regulation of plant cell wall degradation by filamentous fungi ", FEMS Mircrobiol. Rev., vol. 29, No. 4 (2005) 719-39.
Brunner et al., "Xyr1 regulates xylanase but not cellulase formation in the head blight fungus Fusarium graminearum", Curr Genet., vol. 52, Nos. 5-6 (2007) 213-20.
Calero-Nieto et al., "Role of the Transcriptional Activator XlnR of Fusarium oxysporum in Regulation of Xylanase Genes and Virulence", Molecular Plant-Microbe Interactions, vol. 20, No. 8 (2007) 977-85.
De Vries et al., "*Aspergillus* Enzymes Involved in Degradation of Plant Cell Wall Polysaccharides", Microbiol. Mol. Biol. Reviews, vol. 65, No. 4 (2001) 497-522.
Furukawa et al., "Identification of specific binding sites for XYR1, a transcriptional activator of cellulolytic and xylanolytic genes in Trichoderma reesei", Fungal Genet Biol., vol. 46, No. 8 (2009) 564-74.
Hasper et al., "Functional analysis of the transcriptional activator XlnR from *Aspergillus niger*", Microbiology, vol. 150 (2004) 1367-75.
Hasper et al., "The *Aspergillus niger* transcriptional activator XlnR, which is involved in the degradation of the polysaccharides xylan and cellulose, also regulates D-xylose reductase gene expression", Mol. Microbiol., vol. 36, No. 1 (2000) 193-200.
Ilmen et al., "Regulation of Cellulase Gene Expression in the Filamentous Fungus Trichoderma reesei", Appl. Environ. Microbiol., vol. 63, No. 4 (1997) 1298-306.
Karaffa et al., "D-Galactose induces cellulase gene expression in Hypocrea jecorina at low growth rates", Microbiology, vol. 152 (2006) 1507-14.
Kubicek et al., "Metabolic engineering strategies for the improvement of cellulase production by Hypocrea jecorina", Biotechnology for Biofuels, vol. 2, No. 9 (2009) 1-14.
Mach et al., "Regulation of gene expression in industrial fungi: Trichoderma", Applied Microbiology and Biotechnology, vol. 60 (2003) 515-22.
MacPherson et al., "A Fungal Family of Transcriptional Regulators: The Zinc Cluster Proteins", Microbiol. Mol. Biol. Rev., vol. 70, No. 3 (2006) 583-604. Margolles-Clark et al., "Expression patterns of ten hemicellulase genes of the filamentous fungus Trichoderma reesei on various carbon sources", J. Biotechnol, vol. 57 (1997) 167-79.
Martinez et al., "Genome sequencing and analysis of the biomass-degrading fungus Trichoderma reesei", Nature Biotech., vol. 26, No. 5 (2008) 553-60.
Marui et al., "Transcriptional activator, AoXlnR, mediates cellulose-inductive expression of the xylanolytic and cellulolytic genes in Apsergillus oryzae", FEBS Letters, vol. 528, No. 1 (2002) 279-82.
Nagendran et al., "Reduced genomic potential for secreted plant cell-wall-degrading enzymes in the ectomycorrhizal fungus Amanita bisporigera, based on the secretome of Trichoderma reesei", Fungal Genet. Biol., vol. 46, No. 5 (2009) 427-35.
Phalip et al., "Diversity of the exoproteome of Fusarium graminearum grown on plant cell wall", Curr. Genet., vol. 48, No. 6 (2005) 366-79.

(Continued)

Primary Examiner — Ganapathirama Raghu
(74) Attorney, Agent, or Firm — Fitzpatrick, Cella, Harper & Scinto

(57) ABSTRACT

A fermentation process for the production of cellulase mixtures is provided. The process comprises providing a genetically modified host filamentous fungus that overexpresses a Xyr1 transcription factor and/or that is partially or completely deficient in expressing one or more hemicellulase enzyme. The host filamentous fungus is cultured in a medium comprising a carbon source. The carbon source contains from about 60 wt % to about 100 wt % hemicellulose-derived carbohydrate and less than 5% of a cellulase-inducing carbohydrate or contains from about 25 wt % to about 100% wt % hemicellulose-derived sugar alcohol in combination with from about 0 wt % to about 75 wt % glucose, glycerol or a combination thereof.

46 Claims, 17 Drawing Sheets

OTHER PUBLICATIONS

Rao et al., "Regulation of the xylanase gene, cgxA, from *Chaetomium gracile* by transcriptional factors, XInR and AnRP", Biotechnol. Letters, vol. 24, No. 13 (2002) 1089-96.

Rauscher et al., "Transcriptional Regulation of xyn1, Encoding Xylanase I, in Hypocrea jecorina", Eukaryotic Cell, vol. 5, No. 3 (2006) 447-56.

Strauss et al., "Cre1, the carbon catabolite repressor protein from *Trichoderma reesei*", FEBS Letters, vol. 376(1995) 103-7.

Stricker et al., "Xyr1 (Xylanase Regulator 1) Regulates both the Hydrolytic Enzyme System and D-Xylose Metabolism in Hypocrea jecorina", Eukaryotic Cell, vol. 5, No. 12 (2006) 2128-37.

Stricker et al., "Role of Ace2 (Activator of Cellulases 2) within the xyn2 transcriptosome of Hypocrea jecorina", Fungal Genet. Biol., vol. 45, No. 4 (2007) 436-45.

Stricker et al., "Regulation of transcription of cellulases- and hemicellulases-encoding genes in *Aspergillus niger* and *Hypocrea jecorina*", Appl. Microbiol. Biotechnol, vol. 78 (2008) 211-20.

Tamayo et al., "CreA mediates repression of the regulatory gene xlnR which controls the production of xylanolytic enzymes in *Aspergillus nidulans*", Fungal Genet. Biol., vol. 45, No. 6 (2008) 984-93.

Xiong et al., "Improved xylanase production by *Trichoderma reesei* grown on L-arabinose and lactose or D-glucose mixtures", Appl. Micribiol. Biotech., vol. 64 (2004) 353-58.

Zeilinger et al., "Different Inducibility of Expression of the Two Xylanase Genes xyn1 and xyn2 in *Trichoderma reesei*", J. Biol. Chem., vol. 271, No. 41 (1996) 25624-29.

Aro, et al., "ACEI of *Trichoderma reesei* Is a Repressor of Cellulase and Xylanase Expression", Appl. Environ. Microbiol. vol. 69, No. 1 (2003) 56-65.

Ling, et al., "Binding of two transcriptional factors, Xyr1 and ACEI, in the promoter region of cellulase cbhl gene", Biotechnol. Letters, vol. 31 (2009) 227-31.

Walker, et al., "The Language of Biotechnology: A Dictionary of Terms", Second Edition (1995) 133.

Chica, et al., "Semi-rational approaches to engineering enzyme activity: combining the benefits of directed evolution and rational design", Current Opinion in Biotechnology, vol. 16 (2005) 378-84.

* cited by examiner

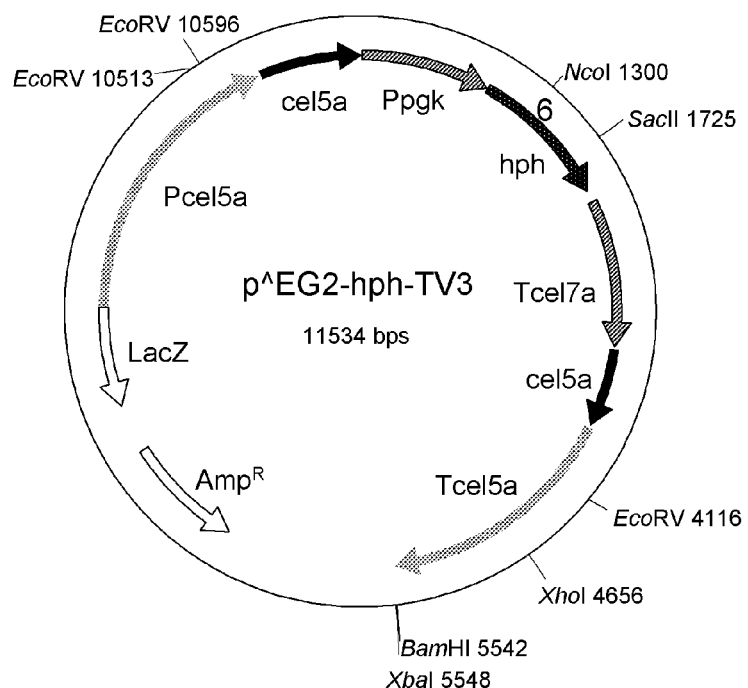
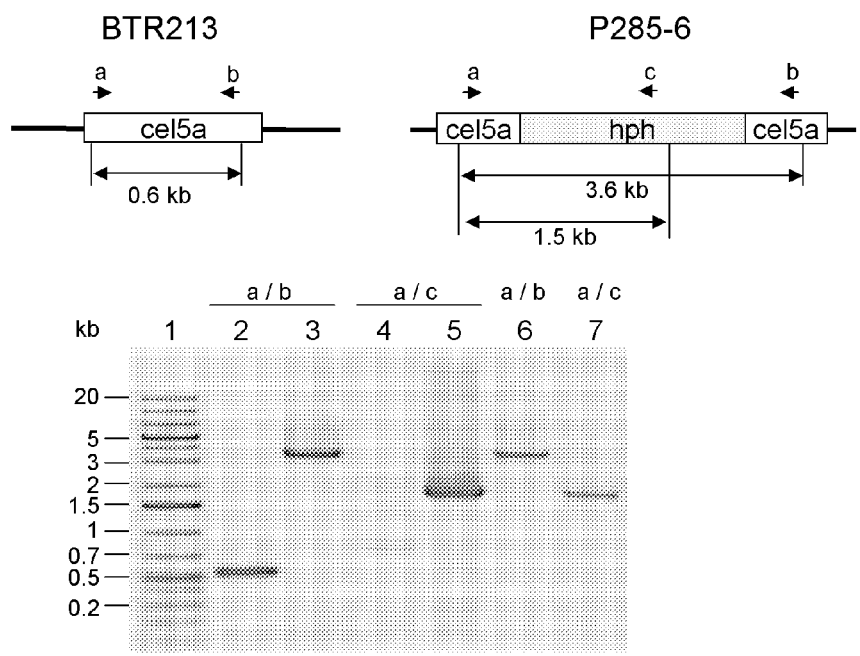
Figure 1

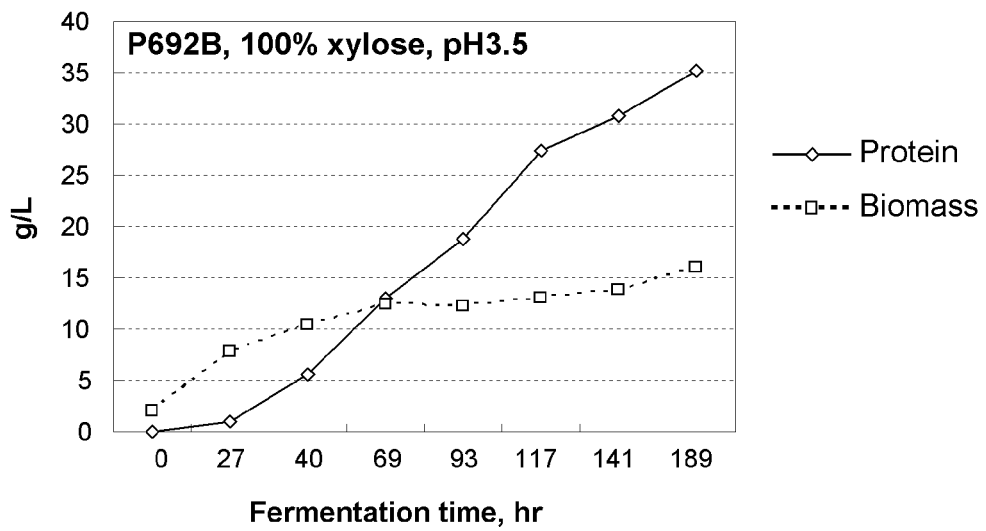
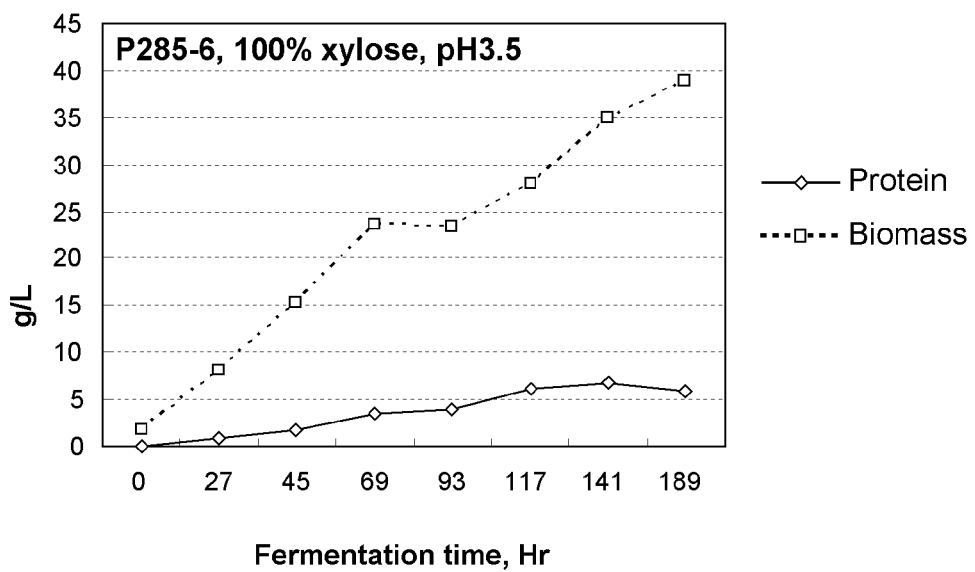
Figure 6

A
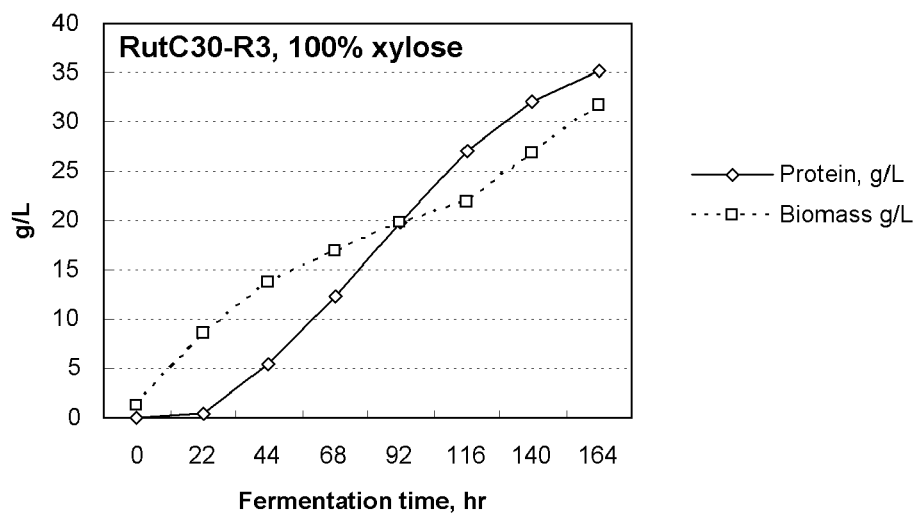
B
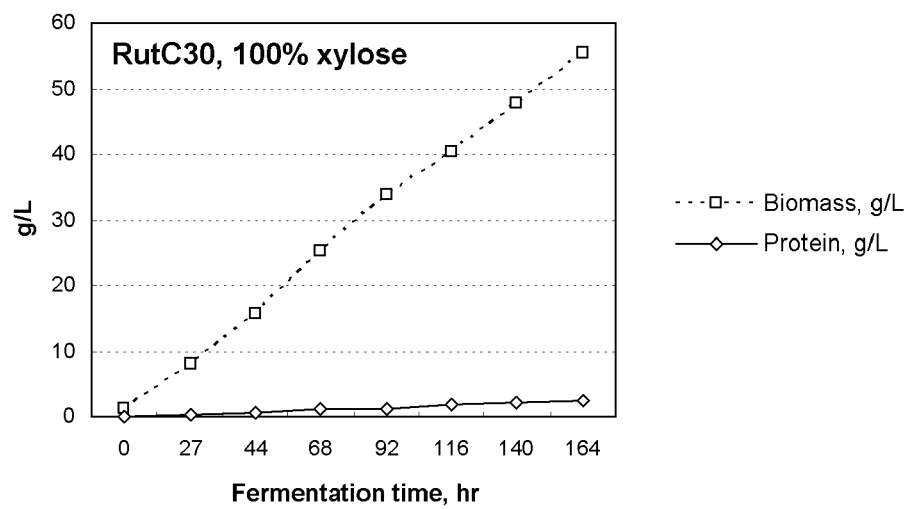
Figure 7

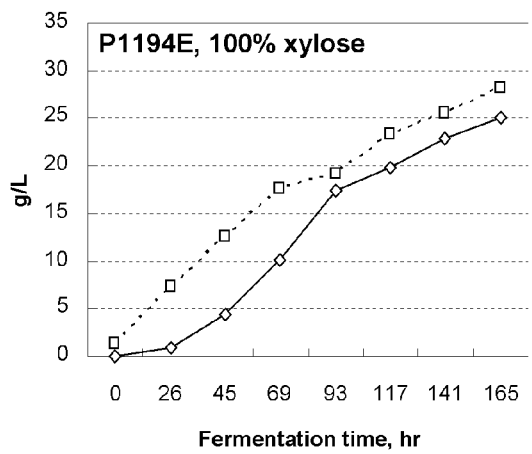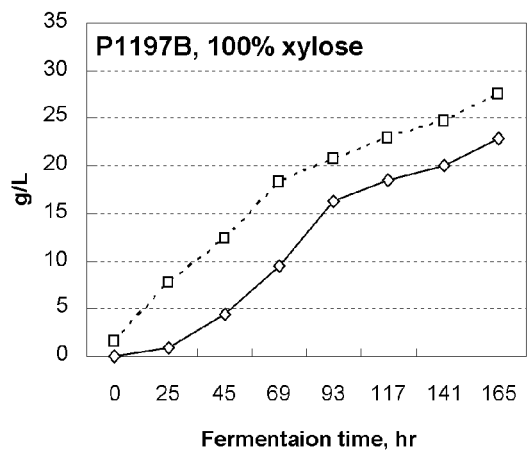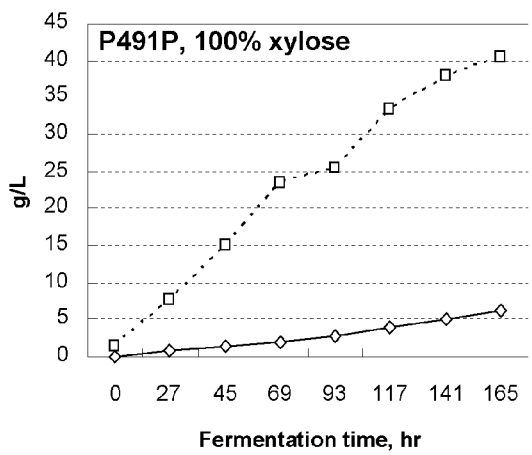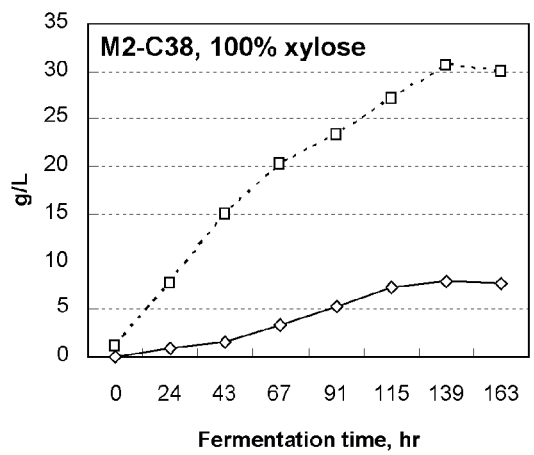
Figure 8

```
Trichoderma_reesei_xyr1    ........................M_SNPLRRYSAYPDISSASFDPNY    24
Aspergillus_niger_XlnR     ..................................................    0
Aspergillus_nidulans_xlnR  ................................................MS    2
Aspergillus_oryzae_AoXlnR  ..MSTTSIQHFTSSFSPFSSGTQPVGMAQSQTVGLDT_L_AEGSQYALEQLQLSREANGASA    58
Asperrgillus_terreus_XlnR  ........................MAPSQTIGLDT_L_AEGSQYSLEQLQLSREAGNDAA    34
Aspergillus_kawachii_XlnR  ..................................................    0
Neurospora_crassa_XlnR     ........................M_L_SNPLHRFAPYHAMPSPTLLSGG    24
Penicillum_canescens_XlnR  MSTTSTSLQSFANSYSPFSSRPQPNRMAQSQTPGLDT_L_AEGSQYALEQLQLARQ...ASA    57
Fusarium_oxysporum_XlnR    ........................M_L_SNPLQRFSPYQNITSSNISPDG    24
Pyrenophora_tritici_XlnR   .............................MLSTNLHQYPSAFSHLPAPNMVEHQHQHH    29
Consensus                                             l  psq Trichoderma_reesei_xyr1    HGSQSHLHSINVNTFGN_S_HPYPMQHLAQHAELSSSRMT_R_ASPV_Q_PK..........QR_QG_    74
Aspergillus_niger_XlnR     ................M_S_HTKDQPPFDNEKNQSTGSGF_R_DAL.QRD..........P_LM_    33
Aspergillus_nidulans_xlnR  QSQSQTIGLDTLAEGSQYVLEQLQLSREGGNSENNSTF_K_PSS.VRD..........S_LA_    51
Aspergillus_oryzae_AoXlnR  VDGGVPNPLRSSISKPQ_G_QQLYSDESSAQHTQNATTGF_R_NLP.QRD..........Q_LA_    107
Asperrgillus_terreus_XlnR  TATSSTS.LRSSSFSKSTDQSVSNPSGNHHSNNGPPSDFKSS.QRD..........P_LA_    82
Aspergillus_kawachii_XlnR  ................M_S_HAKDQPLFDDERNQSAGSGF_K_NTL.QRD..........P_LM_    33
Neurospora_crassa_XlnR     HVTASHLHAAGLDTMGP_G_SHYALQQLQQHVSVHNHHLA_R_AGP.QPK..........HRQH    73
Penicillum_canescens_XlnR  S.....NPPTDSEGKPV_S_PSEALEPPPYREQNGTHSGS_K_SSS.QQH..........DPLV    101
Fusarium_oxysporum_XlnR    NVQQGTMSGTGLESLGQ_S_HQYPIQPLSQAVPLSNAHLE_R_PGP.QVK..........NRQH    73
Pyrenophora_tritici_XlnR   HLAAPHMGHSPLDTLAHTSQYAALQFHQNRHVLPSGKSLVKNHRLPYASGPLAPRNHRDM    89
Consensus                                 l    shqy  qp   q   s  sgfr  sp qrd        l e Trichoderma_reesei_xyr1    SLIA_AR_NSTG_T_AG_P_IRRRISRACDQCNQLRTKCDG_L_HPCAHCIEFGLG_CEY_M_RERKKRG    134
Aspergillus_niger_XlnR     .ARSAVRK.TSS_G_APVRRRISRACDQCNQLRTKCDGQHPCAHCIEFGLTCEYARERKKRG    91
Aspergillus_nidulans_xlnR  .ARS_M_TRK.NSS_G_APVRRRISRACDQCNQLRTKCDGQNPCAHCIEFGLTCEYARERKKRG    109
Aspergillus_oryzae_AoXlnR  .ARS_T_TRK.SSN_G_GPVRRRISRACDQCNQLRTKCDGNPCAHCIEFGLTCEYARERKKRG    165
Asperrgillus_terreus_XlnR  .ARSAIRK.NST_G_APVRRRISRACDQCNQLRTKCDGQHPCAHCIEFGLTCEYARERKKRG    140
Aspergillus_kawachii_XlnR  .ARSAIRK.NSS_G_APVRRRISRACDQCNQLRTKCDGQHPCAHCIEFGLTCEYARERKKRG    91
Neurospora_crassa_XlnR     PYGPVT_R_A.T_G_AAGPIRRRISRACDQCNQLRTKCDGQHPCAHCIEFGLG_CEY_M_RERKKRG    132
Penicillum_canescens_XlnR  _D_ARSAIRK.NSTATAVRRRISRACDQCNQLRTKCDGQQPCAHCIEFGLS_CEY_ARERKKRG    160
Fusarium_oxysporum_XlnR    PYGIHF_NN_.AS_T_SQPIRRRISRACDQCNQLRTKCDGQHPCAHCIEFGLG_CEY_T_RERKKRG    132
Pyrenophora_tritici_XlnR   LQERSG_R_ANSTSGP.................CAHCIEFGLTCEY_T_RERKKRG    124
Consensus                       arsairk  nsssapvrrrisracdqcnqlrtkcdgqhpcahciefgltceyarerkkrg Trichoderma_reesei_xyr1    KASRKDIAAQQ_AAAAAAA_QHSG_Q_VQDGPEDG_R_.....KLSRQQSESSRGSAELAQP.AHD    188
Aspergillus_niger_XlnR     KASKKDI...AAAAAAAATQG.....HSG_ENG_.....H_SG_QANA.........S_LMGERT    125
Aspergillus_nidulans_xlnR  KASKKDI...AAAAAAAAGHQ_G_GMGNRSPTDRR.....LSQEPGG.........RYDSVLE    152
Aspergillus_oryzae_AoXlnR  KASKKDI...AAAAAAAVANN_G_TA....PTSNG.....NTSNDSV.........SSAKRHT    204
Asperrgillus_terreus_XlnR  KASKKDI...AAAAAAAA_G_S......TSES......TANDGGP.........MLTKGHS    177
Aspergillus_kawachii_XlnR  KASKKDI...AAAAAAATHG......SNG.....H_SG_QANA.........S_LMAERT    125
Neurospora_crassa_XlnR     KASRKDIAAQAAAAAAAQLN_G_HKNPSQAGE_ND_.....QSPPNRTESTTATKRA_SS_L.PIE    186
Penicillum_canescens_XlnR  KASKKDI...AAAAA_VA_TSTS_DKGLQDGG_S_VH.....GNSPNGH.........SSH....    199
Fusarium_oxysporum_XlnR    KASRKELAQQ_AAA_G_AAAA_NGQTLDESTS_T_NG.....QSGNKGLDSSNMVLEQQSN.ERH    186
Pyrenophora_tritici_XlnR   KASRKDIAQQQ_AAAAAAA_GNS_A_PKSEESST_FR_APEKVPQSKQAAKSPKLPEGQRALPELPS    184
Consensus                         kaskkdla  qaaaaaaaa     g      tsng       s      g               sl Trichoderma_reesei_xyr1    PPHGHIEGS_MS_G_FS_DN_G_LSQHAAMGGMDGLEDH....HGHVGVDPALGRTQLEASSAMGL    244
Aspergillus_niger_XlnR     SEDSRPGQD_MNG_I_LY_D_SA_E_ESHHLSSQPSHMQHA....STAGISGLHES_G_TAPS..HS_QS_S    179
Aspergillus_nidulans_xlnR  A_S_RVQSHLPA_NG_LSSIHNTQAA....................HS_QP_P    179
Aspergillus_oryzae_AoXlnR  _HS_DGQSTQ_EMSG_RY_D_PN_F_DASRNLATAGQSQLG....QHSDMSGMAGM_G_GSQQTP_HS_QP_S    260
Asperrgillus_terreus_XlnR  _HS_DGRSSHE_IN_G_RY_D_PA_F_DAARTLTNSAQSQLQ....SHADVPGMVGM_NSQQ.E_HS_QP_P    232
Aspergillus_kawachii_XlnR  SEDSRPAQD_MNG_R_YD_STE_ESHHISSQPSHMQHA....NNAGISGLHDS_G_TAPS..HS_QP_S    179
Neurospora_crassa_XlnR     HQTTSNDKT_MSD_MS_G_SVRSQRTGSMDSIDLGA.....HQTHIASHPGAMDRDLESPAALD    242
Penicillum_canescens_XlnR  ........E_MSMEY_D_PA_F_DAARAVPESAQPPLR....NHSVPGISRIQ_NN_HSASGHPQQ    247
Fusarium_oxysporum_XlnR    _HS_.TSSKSSRDPGD_D_VMRHTQGLEGLDPLGNIS....EQPHLGRSSLDGEHIENN_GL_DL    241
Pyrenophora_tritici_XlnR   R_S_ASIATTRPDMDTTP_IY_PNRTMSLSAIDNIPEVDMHHQMSESMHPMQPMQPHRI_ST_GL    244
Consensus                                psd  s  vng  ydp  f   r             q           sg   q      hsqp
```

Figure 13 (cont)

```
Trichoderma_reesei_xyr1      GAYGEVHP.......GYESPGM.....NGHVMPPSYGAQTTMAGYSGISYAAQAPSFAT  292
Aspergillus_niger_XlnR       LGTTIDAM.......HLNHFNTMIDSGRPAMSISDLRSLPPSV............LPPQG  220
Aspergillus_nidulans_xlnR    LGSALDAL.......HLNHFTQLNESGRSQFVSDLRSLQILHNNP...RSPS.ALPHGL  228
Aspergillus_oryzae_AoXlnR    LGGAIDAI.......HLNHFNTILNDSNRPQMSVPDLRSLQMLHPSGANTRSPSGALPPQG  313
Asperrgillus_terreus_XlnR    LGAALDAL.......HLNHFSALNESNRPQMSVPDLRILQMLHPSGTNPRSPSAVLPSQG  285
Aspergillus_kawachii_XlnR    LGTTIDAM.......HLGHFNTILDQGRPAMSMGDLRSLPPSV............LPPQG  220
Neurospora_crassa_XlnR       LSYGNVHQ.......EYHRQGMGAHLMNGASHHTPYGSNQAAMSNYPDLPYALHTQSFTG  295
Penicillum_canescens_XlnR    QVGSGIDS.......ISLNYGNVPDGNRFSMSVFDLRSLQMMQQNGNP.RSPAAMIHSQG  299
Fusarium_oxysporum_XlnR      NGFGSMAH.......GYETQGLEGPVLNGQSYAANGRGNMPGYAEF...PYSMQAQSFPN  291
Pyrenophora_tritici_XlnR     PMHNFNPMAEYTSMEEYHRNLAYQSPLQMMQPGMHPGVSSHDRGIEYSDSPYSMMSFQSA  304
Consensus                    lg    da       hlnhfg lnds rpqmsvpdlrslq       rsps alppqg Trichoderma_reesei_xyr1      YSFDGNFRLTGHIFD...YPLA......NGSSPSWGVSLLASFSNQFCLQLSCPIFKQSD  342
Aspergillus_niger_XlnR       LSSGYNASAFALVNPQEPGSPA.NQFRLGSSAENPIAFFLGL.SPPGQSPGWLPLPSPSP  278
Aspergillus_nidulans_xlnR    NA..YNDNTFSLLNSQEPNTTSLNHFRLGNSTDNPSAQFLGL.SPPAQSPGWLPLPSPSP  285
Aspergillus_oryzae_AoXlnR    MNSGYNDGAYSLMNAGEANHPSINQYRLGNSAENPPAFFLGL.SPPAQSPGWLGLPSPSE  372
Asperrgillus_terreus_XlnR    LNG.YNETAYSLMNPQESNPASMNHFRLGNSAENQPPSFLGL.SPPAQSPGESHLSPLSPYV  343
Aspergillus_kawachii_XlnR    LSSGYNASAFALVNPQEPGSPA.NQFRLGSSAENDTAPFLGL.SPPGQSPGWLPLPSPSE  278
Neurospora_crassa_XlnR       YSANTSSGFRIGASFLSAYPMA......GGSTSPGWMNLLASPFHQFAQHIPQFTYSHAQ  348
Penicillum_canescens_XlnR    FGSGYHDGAYPLMNSHDTNANSIGQFRLGSSAENPSASFLGCFSPPAQSPSWLPLPSPSP  359
Fusarium_oxysporum_XlnR      FANNPT..FRMGNSFLGYSMGK......G..TSPGWGISMASPPGQYQSQVPAEPAFNNSK  341
Pyrenophora_tritici_XlnR     HGQVPSNPFRIAELEQSNMGYMAQSPVGAFGNMILESETTMYSGAPHQTPSQQLRYPVLQ  364
Consensus                        ssgyn   a  l npqe n  a nqfrlg saenp  asflgl sppaqspgwlplpspsp Trichoderma_reesei_xyr1      ..............LRYPVLEPLLPHLGNILPVSLACDLIDLYFSSSSSAQMHPMSPYV  387
Aspergillus_niger_XlnR       ANFPSFSLHPFSST.LRYPVLQPVLPHIASIIPQSLACDLLDVYFTSSSSSHLSPLSPYV  337
Aspergillus_nidulans_xlnR    ANFPSFPMAPFQGTSLRYPVLQPVLPHIASIIPQSLACDLLDLYFTSSSSSHLSPQSPYV  345
Aspergillus_oryzae_AoXlnR    ANFASFSMPPFSST.LRYPVLQPVLPHIASIIPQSLACDLLDVYFTSSSSHLSPQSPYV  431
Asperrgillus_terreus_XlnR    ANFPSFSMNPYFST.LRYPVLQPVLPHIASIIPQSLACDLLDVYFTSSFSSHLSPLSPYV  402
Aspergillus_kawachii_XlnR    ANFPSFSLHPFSST.LRYPVLQPVLPHIASIIPQSLACDLLDVYFTSSSPSHLSPSSPYV  337
Neurospora_crassa_XlnR       ..............LRYPVLEPLLPHLGNLMPVSLACDLIDLYFASSSSAQMHPMSPYV  393
Penicillum_canescens_XlnR    ANFPSFSMAPFAST.LRYPVLQPVLPHIASIIPQSLACDLLDVYFTSSSSSHMSPLSPYV  418
Fusarium_oxysporum_XlnR      ..............LRYPVLEPLVFMLNNPLFIPLACDLIDLYFASSSSAQMHPMSPYV  386
Pyrenophora_tritici_XlnR     ELVPHLANMMPLSLACDLLELYFESSSSAFMQEMSPYVLGYVFRKRSFLRTNSPRVCSPA  424
Consensus                    anfpsfsm  pfsst lrypvlqpvlphiasiipqslacdlldvyftsssshlsp spyv Trichoderma_reesei_xyr1      LGFVFRKRSFLHPTNPRQQSPALLASMLWVAAQTSEASFLTSLPSARSKVCQKLLELTVG  447
Aspergillus_niger_XlnR       VGYIFRKQSFLHPTKPRICSPGLLASMLWVAAQTSEAAFLTSPPSARGRVCQKLLELTIG  397
Aspergillus_nidulans_xlnR    VGYIFRKQSFLHPTKPRVCSPGLLASMLWVGAQTSDAPFLTSPPSARGRVCQKLLELTIG  405
Aspergillus_oryzae_AoXlnR    VGYIFRKQSFLHPTKPRVCSPGLLASMLWVAAQTSDAAFLTSPPSARGRVCQKLLELTVG  491
Asperrgillus_terreus_XlnR    VAYIFRKQSFLHPTKPRVCSPGLLASMLWVAAQTSDAAFLTSPPSARGRVCQKLLELTIG  462
Aspergillus_kawachii_XlnR    VGYIFRKQSFLHPTKPRLCSGGLLASMLWVAAQTSEAAFLTSPPSARGRVCQKLLELTIG  397
Neurospora_crassa_XlnR       LGFVFRKRSFLHPTKPRQQFALLASMLWVAAQTSDAFFLTSVPSARGKICQKLLELTVS  453
Penicillum_canescens_XlnR    VGFVFRKQSFLHPTKPRVCSPGLLASMLWVAAQTSEAAFLTSPPSARGRVCQKLLELTIG  478
Fusarium_oxysporum_XlnR      LGFVFRKRYFLDQTRPRFQQSPALLASMLWVAAQTSDAPFLASTPSARAKTCQKLLELTVY  446
Pyrenophora_tritici_XlnR     LLASMLWIGSLTSESEFYLSGSPSARGQLGSERLINLTISLLKPLVHQTPGDPDC.....  477
Consensus                    vgyifrkqsflhptkprvcspgllasmlwvaaqtsdaafltsppsargrvcqklleltig Trichoderma_reesei_xyr1      LLQPLIHTGTNGPSPKTSPVVG...AAALGMLGVAMPGSLNMDSLAGFTGAF........  496
Aspergillus_niger_XlnR       LLRPLVHGPATGEASPNYAANMVINGVALGGFGV......SMDQLGAQSSAT........  443
Aspergillus_nidulans_xlnR    LLRPLIHGPALGEASPNYAANMVINGVALGGFGV......SMDQLGAQSTAT........  451
Aspergillus_oryzae_AoXlnR    LLRPLIHGPAPGETSPNYAANMVINGVALGGFGV......SMDQLGAQSSAT........  537
Asperrgillus_terreus_XlnR    LLRPLIHGPAPGFTSPNYAANMVINGVALGGFGV......SMDQLGAQSTAT........  508
Aspergillus_kawachii_XlnR    LLRPLVHGPATGEASPNYAANMVINGVALGGFGV......SMDQLGAQSSAT........  443
Neurospora_crassa_XlnR       LLKPLIHTPSFPPSPVSSPIVD...GVALGGLGVALPGSISMDALLGSFTGAF........  502
Penicillum_canescens_XlnR    LLRPLIHGPATGEASPNYAANMVINGVALGGFGV......SMDQLGAQSSAT........  524
Fusarium_oxysporum_XlnR      LLRPLIHTA...PSDAPSPVAD...GVALGGLGVAMPGSLSLDATSGESGPF........  492
Pyrenophora_tritici_XlnR     ........SPTAFANGGMVNGVTM..............GAFGMPTHDSE  504
Consensus                    llrplihgpa geaspnyaanmvingvalggfgv      smdqlgaqsgat
```

Figure 13 (cont)
REPLACEMENT SHEET

```
Trichoderma_reesei_xyr1       ....GAIGSLDDVLITYVHLATVVSASEYKGASLRWWGAAWSLARELKLGRELPFGNPFAN    552
Aspergillus_niger_XlnR        ....GAV...DDVATYVHLATVVSASEYKAASMRWWTAAWSLARELKLGRELPPNVSHAR    496
Aspergillus_nidulans_xlnR     ....GAV...DDVATYVHLATVVSASEYKAASMRWWTAAWSLARELKLGRELPPNASQFG    504
Aspergillus_oryzae_AoXlnR     ....GAV...DDVATYVHLATVISASEYKAASMRWWTAAWSLARELKLGRELPPNAPQFR    590
Asperrgillus_terreus_XlnR     ....GAV...DDVATYVHLATVVSASEYKAASIRWWTAAWSLARELKLGRELPPNTNTAR    561
Aspergillus_kawachii_XlnR     ....GAV...DDVATYVHLATVVSASEYKAASMRWWTAAWSLARELKLGRELPPNVSHAR    496
Neurospora_crassa_XlnR        ....GAAGTLDDVMTYIHLATVVSASEYKGASLRWWLAAWSLARELKLGREIFQNSPSMQ    558
Penicillum_canescens_XlnR     ....GAV...DDVATYVHLATVVSASEYKAASMRWWTAAWSLARELKLGRELPPNTNRQD    577
Fusarium_oxysporum_XlnR       ....GAAGSLDDVLITYIHLAVVVSASEYKGASMRWWTAAWGLARELKLGRELPFGPSFAT    548
Pyrenophora_tritici_XlnR      IGLPGAPGGLDDVATYMHLAIVISASEYKAASLRWWNAAWSLARELKLGKEVFVTPPPET    564
Consensus                         gavg lddvatyvhlatvvsaseykaasmrwwtaawslarelklgrelppn p ar Trichoderma_reesei_xyr1       QE...............DGE.................GLSEDVDEHDLNRNNTRF    575
Aspergillus_niger_XlnR        Q...............DGERDGDEAD..KRHPPTLITSLGHGSGSSGINVT.....    531
Aspergillus_nidulans_xlnR     Q...............DGERENEGDNP..SKRNQSLH....GGNSNV...NVT.....    533
Aspergillus_oryzae_AoXlnR     Q...............DGEPEDDTDVDMSKRNLPPLITSMGNSGSTILNVT.....    627
Asperrgillus_terreus_XlnR     Q...............DGDRDADSVDMSKRNLPSLVTSMGHGSGTP.LNVT.....    597
Aspergillus_kawachii_XlnR     Q...............DGERDGDEAD..RRHPPTLITSLGHGPGSSGINVT.....    531
Neurospora_crassa_XlnR        N...............SGSELDGE.................MGNIPGMI..........    575
Penicillum_canescens_XlnR     G...............ELEGESEMDLNGNKRQTTSLLNGMGHGPGSSINLS.....    614
Fusarium_oxysporum_XlnR       QENMDTDTADDGEGGISGSGYVGE.................................    572
Pyrenophora_tritici_XlnR      NDDDAPVDVDAGHTGRRYPTGQNTPVDY.............................    592
Consensus                     q               dgege d d d   kr  p l ts ghgsgs   nvt Trichoderma_reesei_xyr1       VIEEEREERRRAWWLVYIVDRHLALCYNRPLELLDSEGSDLMHPMDDLKWQAGLFRSHDA    635
Aspergillus_niger_XlnR        ..EEEREERRRLWWLLYATDRHLALCYNRPLTLLDKECGLLQPMNDDLWQMGDFAAAAM    589
Aspergillus_nidulans_xlnR     ..EEEREERRRLWWLLYATDRHLALCYNRPLTLLDKECSQLQPMNDDLWQAGDFPAAIM    591
Aspergillus_oryzae_AoXlnR     ..EEEREERRRLWWLLYATDRHLALCYNRPLTLLDKECFGLLQPMNDDLWQAGDFAGAIM    685
Asperrgillus_terreus_XlnR     ..EEEREERRRLWWLLYATDRHLALCYNQPLRLLDKECGLLQPMNDDLWQAGDFGAVGY    655
Aspergillus_kawachii_XlnR     ..EEEREERRRLWWLLYATDRHLALCYNRPLTLLDKECGGLLQPMNDDLWQMGDFAAAAM    589
Neurospora_crassa_XlnR        .TEEEREERRRIWWLVYIVDRHLALCYNRPLFLLDIECDGLLQPMDDTDYQNGNFYAY..    632
Penicillum_canescens_XlnR     ..EEEREERRRIWWLLYVMDRHLALCYNRPLTLLDKECGLLQPMNDDLWQAGDFGAASM    672
Fusarium_oxysporum_XlnR       ...EEEREERRRIWWLLYIVDRHLALCYNRPLFLLDTECQGLLQPMDDARWQSGDFSGHSN    629
Pyrenophora_tritici_XlnR      .TEEQREERRRIWWLLFTVDRHLALCYNRPLSLLDVECSGLMQPLEDNVWQGGEFFEVSA    651
Consensus                        eeereerrrlwwllyatdrhlalcynrpltlldkec  gllqpmnddlwqagdf aa y Trichoderma_reesei_xyr1       GNSSINIDSSMTDEFGDSPRAAR...GAHYEGRGRSIFGYFLGLMTILGEIVDVHHAKSH    692
Aspergillus_niger_XlnR        RQM.....................GPPVECTGHSMYGYFLPLMTILGGIVDLHHARNH    626
Aspergillus_nidulans_xlnR     RAM.....................GPPIECTALGMFGYFLPLMTILGGIIDLQQAREH    628
Aspergillus_oryzae_AoXlnR     RQM.....................GPQVECTGHSMFGFFLPLMTILGEIVDLQQAKEH    722
Asperrgillus_terreus_XlnR     RQM.....................GPPIECSGHSMFGYFLPLMTILGGIVDLQQAKEH    692
Aspergillus_kawachii_XlnR     RQM.....................GPPVECTGHSMYGYFLPLMTILGGIVDLHHARNH    626
Neurospora_crassa_XlnR        ..TDPNVLASDPNTPAARH...R...GPSFVCTGHSIFGYFLPLMTILGEIVDLHHARNH    684
Penicillum_canescens_XlnR     RRA.....................GPAFECTSHSIFGYFLPLMSILGEIVDLQHARNH    709
Fusarium_oxysporum_XlnR       STTDPNLLGTSPEGYGADM...TQAHGPOYECRGHSIFGYFLPLMTILGEIVDLHHAKNH    686
Pyrenophora_tritici_XlnR      QPFSDSTFRR..........R...GPAFECTGHSIFGFFLPLMTILGEIIDLMHARNH    696
Consensus                                             rqv         gpp ectghsmfgyflplmtilgeivdlhhaknh Trichoderma_reesei_xyr1       PRFGVGFRSARDWDEQVAEITRHLDMYEESLKRFMAKHLPLSSKDKEQFMHDSGAVTDM    752
Aspergillus_niger_XlnR        PRFGLAFRNSEWEPQVLDVTRQLDTYGRSLKEFEARYTSNLILGATDNEPVEGAHLDH    686
Aspergillus_nidulans_xlnR     PRYGLTFRGSEDLDQYLMAITQLDAYGQSLKDFEARYINSLALAENEPPENPHI...DH    685
Aspergillus_oryzae_AoXlnR     PRFGRVFRNSADWDHQVLEITRQLDTYAQSLKEFEARYTSSLALGAGESFAATEGSHLDH    782
Asperrgillus_terreus_XlnR     PRFGIAFRNSGEWEHQVLELTRQLETYGQSLKEFESRYTSGLALGAADNETIVDGHLDH    752
Aspergillus_kawachii_XlnR     PRFGLAFRNSEWEPQVQDVTRQLDTYGRSLKEFEARYTSNLILGTAENEPAVEGAHLDH    686
Neurospora_crassa_XlnR        PRFGVGFRGSGREWDDQTAEITRHLEDYEESIKRFELRNLSLSAQAQAADEKAAEAA.GVP    743
Penicillum_canescens_XlnR     PRFGLHFRNSGEWESQAMEITRQLDMYGNSLKEFEARYTSSLALGDNDTAM.EGAHINH    768
Fusarium_oxysporum_XlnR       PRFGTGFRKQGHEWNAQTAEITRHLEIYEQSLQAFERHNLPRPAEERVDAQNEGNERSGVP    746
Pyrenophora_tritici_XlnR      PRFGTKTD...WDDHAREISQQLDAYGRSLQELRNNAVNEANAEPVHP..........    742
Consensus                     prfgl frns ewd qv eitrqldtygqslkefearytsslalg  e  egahldh
```

Figure 13 (cont)
REPLACEMENT SHEET

```
Trichoderma_reesei_xyr1      ...........QSPLSVRTNASSRMTESEIQASIVVAYSTHVMHVLHILLADKWDPI  798
Aspergillus_niger_XlnR       TSPSGRSS.STVGSRVS...........ESIVHTRMVVAYGTHIMHVLHILLAGKWDPV  733
Aspergillus_nidulans_xlnR    LSPSGRSS.STVGSRVN...........ESIVHTKMVVAYGTHIMHVLMVLLAGKWDPI  732
Aspergillus_oryzae_AoXlnR    VSPSGRST.STAGSRVN...........ESIVHTKMVVAYGTHIMHVLHVLLAGKWDPI  829
Asperrgillus_terreus_XlnR    VSPSGRSS.STVGSRIN...........ESIVHTKMVVAYGTHIMHVLHILLAGKWDPI  799
Aspergillus_kawachii_XlnR    TSPSGRSS.STVGSRVS...........GSIMHTRMVVAYGTHIMHVLHILLAGKWDPV  733
Neurospora_crassa_XlnR       TANDVPHDAGTRSVQSVHSVHTT.SSRMTESDIQTRIVMAYGTHVMHVLHILLGKWDPI  802
Penicillum_canescens_XlnR    VSPSGRSNSSTVGSHVS...........ESIVHTRMVVAYGTHIMHVLHILLAGKWDPI  816
Fusarium_oxysporum_XlnR      .......DANTPSAHSVHTNGSN.RL...TESNIQTRIVIAYGTHVMHVLHILLAGKWDPI  796
Pyrenophora_tritici_XlnR     .........GTPSVQ...SVNST.ISRAQESLMHAKIVRAYGTHLMFTLHILLNGKWDPI  789
Consensus                     spsgrss stvgsrv         esivhtrmvvaygthimhvlhillagkwdpi Trichoderma_reesei_xyr1      NLLDDDLWISSEGFVTALSHAVSAAEAISQILEFDPGLEFMPFFYGVYLLQGSFLLLLI  858
Aspergillus_niger_XlnR       NLLEDHDLWISSESFVSAMSHAVGAAEAAAEILEYDPDLSFMPFFFGIYLLQGSFLLLLA  793
Aspergillus_nidulans_xlnR    NLLEDHDMWISSESFLAAMSHAVGAAEAAADILEYDPDLSFMPFFFGIYLLQGSFLLLLA  792
Aspergillus_oryzae_AoXlnR    NLLEDHDLWISSESFTAAMSHAVGAADAAADILEYDPDIQFMPFFFGIYLLQGSFLLLLA  889
Asperrgillus_terreus_XlnR    NLLEDQDLWISSESFITAMGHAVGAADAAADILEYDPDLSFMPFFFGIYLLQGSFLLLLA  859
Aspergillus_kawachii_XlnR    NLLEDHDLWISSESFVSAMSHAVGAAEAAAEILEHDPDLSFMPFFFGIYLLQGSFLLLLA  793
Neurospora_crassa_XlnR       NLLDDNDLWISSQGFITALGHAVSAAEALSNILEYDPGLEFMPFFFGIYLLQGSFLLLLI  862
Penicillum_canescens_XlnR    NLLDDNDLWISSDSFITAMGHAVSAAEEAASDILEYDPDLSFMPFFFGIYLLQGSFLLLLT  876
Fusarium_oxysporum_XlnR      NLLDDEDLWISSQGFITSTSHAVAAAEAIDQILEFDPGLEFMPFFFGIYLLQGSFLLLLI  856
Pyrenophora_tritici_XlnR     SLLDDNDLWISSQSFVFATGHAVSAAEALNEILEYDPDLSFMPFFFGIYLLQGSFLLLLI  849
Consensus                    nlldhdlwissesfitamshavgaaeaaadileydpdlsfmpfffgiyllqgsfllla Trichoderma_reesei_xyr1      ADKLQAEASPSVIKACETIVRAHEACVVTLGTEYQRNFKVMRSALALIRGRVPEDLAEQ  918
Aspergillus_niger_XlnR       ADKLQGDASPSVVRACETIVRAHEACVVTLNTEYQRTFRKVMRSALAQVRGRIPEDFGEQ  853
Aspergillus_nidulans_xlnR    ADKLQGDAITPSVVRACETIVRAHEACVVTLNTEYQRTFRKVMRSALAQVRGRVPDDFGEQ  852
Aspergillus_oryzae_AoXlnR    ADKLQGDVSPSVVRACETIVRAHEACVVTLNTEYQRTFRKVMRSALAQVRGRMPEDFGEQ  949
Asperrgillus_terreus_XlnR    ADKLQGDASPSVVRACETIVRAHEACVVTLNTEYQVRSHSQGYAPRLY............  907
Aspergillus_kawachii_XlnR    ADKLQGDASPSVVRACETIVRAHEACVVTLNTEYQRTFRKVMRSALAQVRGRIPEDFGEQ  853
Neurospora_crassa_XlnR       ADKLQMEASPSVVKACETIIRAHEACVVTLNTEYQRNFGRVMRSALAQVRGRVPEDLGEQ  922
Penicillum_canescens_XlnR    ADKLQGDASPSVVRACETIVRAHEACVVTLNTEYQRTFRKVMRSALAQVRGRVPEDFGEQ  936
Fusarium_oxysporum_XlnR      ADKLQSEASPSVAKACETIVRAHEACVVTLGTEYQRFGKVMRSALAQVRGRVPEDLGEQ  916
Pyrenophora_tritici_XlnR     ADKLQGDANERIVRACEMIVRAHEACIVTLNTEYQRNFRKVMRSTLQQVRGRGMDERAEL  909
Consensus                    adklqgdaspsvvracetivraheacvvtlnteyqrtfrkvmrsalaqvrgrvpedfgeq Trichoderma_reesei_xyr1      QQRRELLALYRWTGNGIGLAL.         940
Aspergillus_niger_XlnR       QQRREVLALYRWSGDGSGLAL.         875
Aspergillus_nidulans_xlnR    QQRREVLGLYRWTGDGIGLALS         875
Aspergillus_oryzae_AoXlnR    QQRREVLALYRWTGDGSGLAL          971
Asperrgillus_terreus_XlnR    ....................           907
Aspergillus_kawachii_XlnR    QQRREVLALYRWSGDGSGLAL.         875
Neurospora_crassa_XlnR       HQRRELLALYRWTGDGIGLAL.         944
Penicillum_canescens_XlnR    QQRREVLALYRWSGDGSGLAL.         958
Fusarium_oxysporum_XlnR      QQRRELLAVYRWTKDGIGLAL.         938
Pyrenophora_tritici_XlnR     ADRFQGNVEPLPLDW.......         925
Consensus                    qqrrevlalyrwtgdgsglal
```

Figure 13 (cont)

| Fungal species | T. reesei | A. niger | A. nidulans | A. kawachii | A. oryzae | A. terreus | F. oxysporum | N. crassa | P. canescens | P. tritici |
|---|---|---|---|---|---|---|---|---|---|---|
| T. reesei | | 54.66 | 53.95 | 54.50 | 55.28 | 48.91 | 64.29 | 66.46 | 56.06 | 48.29 |
| A. niger | 46.65 | | 74.57 | 88.04 | 78.73 | 72.83 | 55.43 | 57.14 | 77.33 | 49.07 |
| A. nidulans | 46.24 | 71.62 | | 73.95 | 75.81 | 67.44 | 54.11 | 55.81 | 72.56 | 48.68 |
| A. kawachii | 47.06 | 95.54 | 72.28 | | 77.64 | 71.27 | 55.12 | 56.68 | 76.09 | 48.76 |
| A. oryzae | 46.55 | 71.09 | 69.99 | 70.78 | | 74.38 | 55.75 | 56.99 | 75.78 | 48.29 |
| A. terreus | 42.83 | 67.97 | 68.57 | 67.65 | 74.38 | | 49.53 | 51.09 | 69.25 | 45.77 |
| F. oxysporum | 59.30 | 48.76 | 48.38 | 47.49 | 47.54 | 45.07 | | 68.79 | 57.30 | 48.76 |
| N. crassa | 58.65 | 48.86 | 48.30 | 48.72 | 48.19 | 43.66 | 61.40 | | 59.94 | 52.64 |
| P. canescens | 50.91 | 68.09 | 66.39 | 67.15 | 71.12 | 67.38 | 47.94 | 49.05 | | 50.31 |
| P. tritici | 42.11 | 43.14 | 42.33 | 42.68 | 41.71 | 40.00 | 42.54 | 44.02 | 42.77 | |

Figure 14 ns and Visser, 2001; Aro et al., 2005, and references# HOSTS AND FERMENTATION PROCESSES FOR CELLULASE PRODUCTION

FIELD OF THE INVENTION

The present invention relates to a fermentation process for the production of a cellulase mixture. More specifically, the present invention relates to a fermentation process comprising the use of genetically modified filamentous fungi hosts for the production of a cellulase mixture.

BACKGROUND OF THE INVENTION

Plant cell walls consist mainly of the large biopolymers cellulose, hemicellulose, lignin and pectin. Cellulose and hemicellulose constitute an important renewable and inexpensive carbon source for the production of fermentable sugars. Cellulose consists of D-glucose units linked together in linear chains via beta-1,4 glycosidic bonds. Hemicellulose consists primarily of a linear xylan backbone comprising D-xylose units linked together via beta-1,4 glycosidic bonds and numerous side chains linked to the xylose units via beta-1,2 or beta-1,3 glycosidic or ester bonds (e.g., L-arabinose, acetic acid, ferulic acid, etc).

Filamentous fungi of the phylum (division) Ascomycota, including various *Penicillium, Phanerochaete, Agaricus, Neurospora, Humicola, Fusarium, Chaetomium, Magnaporthe, Aspergillus* and *Trichoderma* species, have a key role in degradation of the most abundant polymers found in nature, cellulose and hemicellulose. *Trichoderma reesei* (the asexual anamorph of *Hypocrea jecorina*) is an important industrial source of cellulase and hemicellulase enzymes. The term cellulase (or cellulase enzymes) broadly refers to enzymes that catalyze the hydrolysis of the beta-1,4-glucosidic bonds joining individual glucose units in the cellulose polymer. The catalytic mechanism involves the synergistic actions of endoglucanases (E.C. 3.2.1.4), cellobiohydrolases (E.C. 3.2.1.91) and beta-glucosidase (E.C. 3.2.1.21). The term hemicellulase broadly refers to enzymes that catalyze the hydrolysis of the various glycosidic bonds joining individual xylose, arabinose, mannose, galactose and other moieties in the hemicellulose polymer. Hemicellulases include, for example, endo-1,4-beta-xylanases (EC 3.2.1.8), beta-mannanases (EC 3.2.1.28), alpha-L-arabinofuranosidases (EC 3.2.1.55), 1,4-beta-xylosidase (EC 3.2.1.27) and alpha-glucuronidase (EC 3.2.1.139).

*Trichoderma reesei* is a commonly used industrial species of filamentous fungi for the production of biomass degrading enzymes such as cellulases and hemicellulases. Analysis of the secretome of *T. reesei* strain RutC30 revealed the presence of 31 secreted glycosyl hydrolases when grown in media supplemented with pretreated corn stover (Nagendran et al., 2009) Studies of the secretome of *F. graminearum* grown on hop cell wall identified that at least 45% of the secreted proteins are involved in plant cell wall degradation, with 25, 19 and 11 different proteins for hemicellulose, pectin and cellulose degradation, respectively (Phalip et al., 2005).

Sequencing and analysis of the *T. reesei* genome has revealed the presence of 10 genes encoding cellulase and 16 genes encoding hemicellulases (Martinez et al., 2008). These include two cellobiohydrolases, eight endoglucanases, four xylanases, two alpha-L-arabinofuranosidases, and a beta-mannanase. *T. reesei* also produces a number of accessory enzymes that assist in the generation of monosaccharides from the cellulose and hemicellulose, including acetyl xylan esterase, beta-xylosidase and several beta-glucosidases (de Vries and Visser, 2001; Aro et al., 2005, and references therein). However, when compared with the genomes of other filamentous fungi, the *T. reesei* genome has surprisingly few genes encoding glycoside hydrolases (total 200) (Martinez et al., 2008). For example, *Aspergillus oryzae, Aspergillus fumigatus, Aspergillus nidulans* and *Fusarium graminearum* encodes 285, 263, 247 and 243 glycosyl hydrolases, respectively (Martinez et al., 2008).

The production of plant cell wall degrading enzymes such as cellulases, hemicellulases, ligninases and pectinases, by filamentous fungi is regulated mainly at the transcriptional level in response to available carbon sources. Glucose represses cellulase gene expression through the action of transcriptional regulators such as cre1 (Strauss et al., 1995,). Under glucose-limiting conditions, cellulase transcription is derepressed, with full activation of transcription requiring the presence of a cellulase-inducing carbohydrate, or inducer, such as cellulose, or beta-linked disaccharides such as cellobiose, sophorose, gentiobiose and lactose (Ilmen et al., 1997), while activation of hemicellulase transcription is dependent on the presence of xylan or its derivatives (xylose, xylobiose, arabinose) in the growth media (Margolles-Clark et al., 1997).

The transcriptional regulator XlnR (xylanase regulator), initially identified in *Aspergillus niger*, controls the transcription of about 20-30 genes encoding hemicellulases and cellulases (Stricker et al, 2008 and references therein). Moreover, the extracellular xylan degradation and intracellular D-xylose metabolism is coupled via the transcriptional regulation of the xyrA (D-xylose reductase-encoding) gene by XlnR (Hasper et al, 2000). The orthologous transcription factors in *T. reesei*, Xyr1 (xylanase regulator 1) and *Aspergillus oryzae* (Ao XlnR) are also a general regulators of cellulase and hemicellulase gene expression (Striker et al, 2006; Marui et al, 2002). Studies of several other identified regulators of xylanase expression in fungi are limited to the regulation of hemicellulase genes (Tamayo et al, 2008; Rao et al, 2002; Calero-Nieto et al, 2007). For examples, it has been shown that deletion of an orthologous transcription factor to Xyr1 from *Fusarium graminearum* did not affect the basic expression levels of xylanases and cellulases but did prevent high inducible expression (Brunner et al, 2007). This finding is in contradiction to the studies with *Trichoderma* and *Aspergillus*, where the knock out of the corresponding regulator abolishes cellulase and xylanase expression completely. These observations led to a system for production of homologous and/or heterologous proteins using XlnR regulated promoter along with overexpression of xylanase regulator, XlnR, from multiple gene copies (U.S. Pat. No. 6,177,261 B1, 2001).

Xylanase regulators, such as Xyr1 from *Trichoderma* and XlnR from *Aspergillus*, belong to class III zinc binuclear cluster protein family found exclusively in fungi and possess a conserved amino acid motif $(CX_2CX_6CX_{5-12}CX_2CX_{6-8}C)$ at the N-terminal part of the protein (MacPherson et al., 2006). This class of transcription factors is unique in containing only one zinc finger that binds two zinc atoms. Xylanase regulators bind 5'-GGC(T/A)$_3$-3' response elements in the promoters of target genes, and may interact with DNA as monomers, homodimers or heterodimers (MacPherson et al., 2006; Stricker et al., 2008). Several studies have shown that *T. reesei* Xyr1 is essential for the expression of all major (hemi) cellulase genes (Stricker et al., 2006) and that it binds to xylanase 1, 2 and 3 gene promoters (Rauscher et al, 2006; Stricker et al, 2007; Furukawa et al, 2009). However, in vitro binding of *T. reesei* Xyr1 to cellulase gene promoters was only recently demonstrated (Furukawa et al, 2009; Ling et al., 2009). In silico analysis has revealed that the 5'-GGC(T/A)$_3$-3' motifs are widespread as single sites in 5'-upstream region of all Xyr1-regulated genes in *T. reesei* (Furukawa et al, 2009). However in vitro studies of Xyr1 binding to selected motifs revealed that only several of them can be recognized by this transcription factor (Furukawa et al, 2009).

Other functional domains have been identified for *A. niger* XlnR by loss-of-function mutations and rational design mutagenesis analyses (Hasper et al., 2004). These studies demonstrated that the second putative coiled-coil domain is involved in the nuclear localization of the protein. Protein structure predictions suggest the presence of two coiled-coil domains at similar positions in *A. niger* XlnR and *T. reesei* Xyr1. Thus, the second coiled-coil domain of *T. reesei* Xyr1 may likewise be responsible for its transport into the nucleus. The C-terminus of XlnR is essential for transcriptional regulation; deletion of 78 C-terminal amino acids causes increased expression of XlnR target genes, even under glucose repression conditions, suggesting this region dampens transcriptional activation by XlnR (Hasper et al., 2004). However, certain single-amino acid mutations in this region such as Tyr864Phe, Leu823Ser and Tyr864Asp lead to severely diminished activation by XlnR (Hasper et al., 2004).

Although *A. niger* XlnR and *T. reesei* Xyr1 share similarities in structure and in consensus binding sites, there is evidence to suggest that these factors interact with promoters via different mechanisms. For example, it was suggested that *A. niger* XlnR binds as a monomer (Hasper et al., 2004), while *T. reesei* Xyr1 binds to an inverted repeat within a regulated gene promoter, as either a homo- or a heterodimer with Ace2, a known positive regulator of cellulase expression in *T. reesei* (Stricker et al., 2006, 2008). It is also hypothesized that regulation of hemicellulase and cellulase gene expression in *T. reesei* by Xyr1 and Ace2 may involve phosphorylation and recruitment of other regulatory proteins (Stricker et al., 2008). *T. reesei* Xyr1 also has an antagonistic relationship with Ace1, a negative regulator of cellulase genes, through a possible competition of the two factors for the same binding site within cellulase promoters (Stricker et al, 2006). Putative Ace1-encoding genes were isolated from several other fungal species, such as *Aspergillus nidulans, Talaromyces emersonii*, and *Neurospora crassa* (Aro et al, 2005); however, their possible interaction with XlnR and their participation in transcriptional activation of hydrolase-encoding genes has not yet been shown (Stricker et al., 2006).

*T. reesei* produces low levels of xylanase activity under cellulase-inducing conditions; however, the enzyme system produced by cultures of *T. reesei* growing on xylan, xylose and arabinose, is enriched in hemicellulase activities relative to cellulase activities (Mach and Zeilinger 2003; Margolles-Clark et al., 1997; Xiong et al., 2004). This could be beneficial when the goal is to produce an enzyme composition having high xylanolytic activity relative to cellulase activity, as in the animal feed and pulp and paper industry. U.S. Pat. Nos. 6,300,112 and 5,298,405 disclose the use of cellulase-deletion strains as an alternative approach to the production of hemicellulase-enriched enzyme preparations for use in animal feed and for bio-bleaching applications There are situations in which it is desirable to produce cellulase mixtures with a high cellulase specific activity from fungal cultures using carbohydrate sources comprising mainly xylose and other pentose sugars derived from hemicellulose, such as those produced by chemical treatments of lignocellulosic biomass. These may contain HDC or CIC However, such carbon sources result in enzyme compositions containing high hemicellulase activity with decreased cellulase specific activity, and, as a consequence, higher dosages of total protein are needed for effective hydrolysis of cellulose.

Further, the production and secretion of hemicellulase enzymes uses cell energetic and secretion pathway resources and limits the cellulase expression and secretion capacity of the host cell.

It has been reported that a combination of xylan-derived carbohydrates with cellulase inducers such as cellobiose or lactose can lead to different proportions of cellulase and hemicellulase in the protein mixture secreted by *Trichoderma reesei* (Zeilinger, S., et al., 1996,). In addition, it has been found that concentrations of inducer (need to define) of 8 (check)-15% can improve protein production on hemicellulose derived carbohydrate (HDC) almost up to the levels produced when cellulase inducing carbohydrates are used as the carbon source. (See co-pending U.S. application Ser. No. 12/200,492). However, due to high cost of inducing carbohydrates, the use of such mixtures on a large scale can significantly increase enzyme production costs. Moreover, a significant proportion of such an enzyme mix will still be composed of hemicellulases. Consequently, due to the high content of hemicellulases, and the requirement of adding cellulase inducing carbohydrates, the production of cellulase on hemicellulase derived carbohydrates is currently not cost effective.

Thus, there is a need in the art for a cost-effective method of producing a cellulase mixtures containing low levels of hemicellulase activity from filamentous fungi using primarily hemicellulose derived carbohydrate (HDC) in the absence of the cellulase inducing carbohydrates, such as cellulose, or β-linked disaccharides such as cellobiose, sophorose, gentiobiose and lactose, or containing low levels of such carbohydrates.

SUMMARY OF THE INVENTION

The present invention relates to a fermentation process for the production of cellulase mixtures with a high proportion of cellulase components using genetically modified filamentous fungi provided with a carbon source comprising hemicellulose-derived carbohydrates (HDC) in the absence of, or containing low levels of, traditional cellulase inducing carbohydrates (CIC). The process and genetic modifications described herein can be used for the development of fungal strains producing high yields of high quality cellulase enzymes where cellulase expression is not dependent on the presence or absence of cellulase inducible carbohydrates.

The host filamentous fungus is genetically modified to overexpress a Xyr1 transcription factor or a Xyr1 equivalent transcription factor. This genetic modification results in the production of a cellulase mixture enriched in cellulase activity when the host filamentous fungus is supplied with a carbon source containing hemicellulose-derived carbohydrate and low levels of a cellulase inducing carbohydrate.

The present invention provides a fermentation process for the production of a cellulase mixture comprising: a) providing a genetically modified host filamentous fungus that overexpresses a Xyr1 transcription factor or a Xyr1 equivalent transcription factor and b) culturing the host filamentous fungus of step a) in a medium comprising a carbon source containing from about 60 wt % to about 100 wt % hemicellulose-derived carbohydrate and from about 0 wt % to about 3 wt % of a cellulase-inducing carbohydrate or in a medium comprising a carbon source containing from about 25 wt % to about 100 wt % of a hemicellulose-derived sugar alcohol, about 0% cellulase-inducing carbohydrate and from about 0 wt % to 75 wt % glucose, glycerol or a combination thereof to produce the cellulase mixture. The cellulase mixture thus produced comprises form about 40% to about 100% cellulase components and has at least a 1.7-fold increase in cellulase activity relative to a cellulase mixture produced by a parental filamentous fungus that does not overexpress a Xyr1 transcription factor when cultured in the same medium.

The Xyr1 transcription factor that is overexpressed in the host filamentous fungus used in the fermentation process of the present invention is a protein comprising the amino acid sequence of SEQ ID NO: 27, a protein with an amino acid sequence exhibiting from about 90% to about 100% identity to the amino acid sequence of SEQ ID NO: 27. The Xyr1 equivalent transcription factor, a protein with an amino acid sequence exhibiting from about 45% to about 99% identity to the amino acid sequence of SEQ ID NO: 27, a protein with an amino acid sequence exhibitin from about 90% to about 99% identity to the amino acid sequence of SEQ ID NO: 25, SEQ ID NO: 28, SEQ ID NO: 29, SEQ ID NO: 30, SEQ ID NO: 31, SEQ ID NO: 32, SEQ ID NO: 33, SEQ ID NO: 34, or SEQ ID NO: 35 or a protein containing a zinc binuclear cluster that that possesses equivalent DNA binding activity specific to a consensus sequence $GGC(T/A)_3$-like motif within cellulase and/or hemicellulase promoter sequences as the protein with the amino acid sequence of SEQ ID NO: 27.

The host filamentous fungus used in the fermentation process of the present invention may be a species of cellulolytic fungus belonging to the subphylum *Pezizomycotina*. For example, the host filamentous fungus may be a species of *Trichoderma, Hypocrea, Aspergillus, Fusarium, Penicillium*, or *Neurospora*. Preferably, the host filamentous fungus is *Trichoderma reesei* or *Hypocrea jecorina*.

In a first embodiment of the fermentation process of the present invention, the host filamentous comprises a Xyr1 genetic construct in which a nucleic acid sequence encoding a Xyr1 transcription factor or a Xyr1 equivlalent transcription factor is operatively linked to a promoter nucleic acid sequence. The host filamentous fungus may be produced by transformation with the Xyr1 genetic construct and selecting transformants containing the genetic construct.

The promoter nucleic acid sequence may be native or heterologous with respect to the nucleic acid sequence encoding the Xyr1 transcription factor. The promoter nucleic acid sequence may be derived from a gene whose expression is induced during growth of the host filamentous fungus on a carbon source comprising hemicellulose derived carbohydrate. For example, if the host filamentous fungus is *T. reesei*, the promoter nucleic acid sequence may be derived from one or more *T. reesei* genes encoding beta-xylosidase 1, beta-xylosidase 2, xylanase 1, xylanase 2, xylanase 3, or any combination thereof. The promoter nucleic acid sequence may also be a combination of nucleic acid sequences derived from two or more promoters. Alternately, the promoter nucleic acid sequence may be derived from a gene whose expression is constitutive during growth of the host filamentous fungus and whose expression levels are independent of the carbon source used for the fermentation process.

In a second embodiment of the fermentation process of the present invention, the modified host filamentous fungus is modified further to be partially or completely deficient in the expression of one or more hemicellulase enzymes including, but not limited to, xylanases, beta-xylosidases, alpha-arabinofuranosidases, beta-mannases, alpha-glucuronidases, acetyl xylan esterases or any combination thereof. For example, the modified host filamentous fungus may be deficient in the expression of one or more xylanases, one or more beta-xylosidases, one or more alpha-arabinofuranosidases, or any combination thereof. If the modified host filamentous fungus is a strain of *T. reesei* or *H. jecorina*, the host may be modified to be partially or completely deficient in xylanase 1, xylanase 2, beta-xylosidase 1, beta-xylosidase 2, alpha-arabinofuranosidase 1, alpha-arabinofuranosidase 2, or any combination thereof.

The carbon source provided to the host filamentous fungus during the fermentation process of the present invention may comprise other carbon sources in addition to the hemicellulose-derived carbohydrate. For example, the carbon source may comprise glycerol or other sugar alcohols such as xylitol or arabitol or an organic acid such as acetic acid or glucuronic acid.

The fermentation process of the present invention may exhibit at least about a 2-fold increase in specific productivity ($q_p$) when compared to the $q_p$ of a process in which the host filamentous fungus does not overexpress Xyr1

The fermentation process of the present invention may be conducted at a temperature of from about 20° C. to about 35° C. and at a pH from about 3.0 to about 6.5 and may be carried out as a batch, fed-batch, or continuous process. Any of these modes may be operated aerobically, in the presence of oxygen, or anaerobically, in the absence of oxygen.

The present invention is based in part on the observation that cellulase mixtures with a high proportion of cellulase components can be produced by a host filamentous fungus that overexpreses a Xyr1 transcription factor in a fermentation process in which the carbon source comprises hemicellulose-derived carbohydrates (HDC) or hemicellulose-derived sugar alcohols (HDSA) in the absence, or containing low levels, of cellulase-inducing carbohydrates. The productivity of the fermentation process is significantly higher than the same process using a host filamentous fungus that does not overexpress a Xyr1 transcription factor and/or posseses wild type production levels of hemicellulases.

The fermentation process of the present invention produces a cellulase mixture that has at least about a 1.7-fold increase in cellulase activity relative to the cellulase activity of a cellulase mixture produced by a parental filamentous fungus that does not overexpress Xyr1. Cellulase components comprise about 40 wt % to about 100 wt % of the total protein present in the cellulase mixture produced by the fermentation process of the present invention. The cellulase mixture thus produced may be used in the hydrolysis of a cellulose substrate to produce glucose. For example, the cellulase mixture may be used to hydrolyze cellulose contained in a pretreated lignocellulosic feedstock.

BRIEF DESCRIPTION OF THE DRAWINGS

FIG. 1. A—*Trichoderma reesei* transformation vector used for endoglucanase 2 (cel5a) deletion and generation of P285-6 strain. B—Top panel: Schemes of intact, native cel5a gene in strain BTR213 and disrupted cel5a gene in strain P285-6. Primers used for PCR (a, b and c) are indicated as arrows above the schemes and the expected size of the amplified PCR product using each pair of primers (a/b or a/c) is indicated below each scheme. Bottom panel: PCR amplification of intact and disrupted cel5a genes using DNA isolated from strain BTR213 (lanes 2 and 4), strain P285-6 (lanes 3 and 5) and transformation vector pEG2-hph-TV (lanes 6 and 7) as templates. Pairs of primers used for amplification (a/b or a/c) are indicated above each lane number and the sizes of molecular weight markers in lane 1 are indicated to the left.

FIG. 6. The protein (solid lines) and biomass (dotted lines) accumulation, expressed in g/L, in fermentations of modified host filamentous fungal overexpressing Xyr1 (T. reesei P692B) (A) and parental filamentous fungi (T. reesei strain P285-6) (B) strains grown on 100% xylose as a carbon source at pH 3.5.

FIG. 7. The protein (solid lines) and biomass (dotted lines) accumulation, expressed in g/L, in fermentations of modified host filamentous fungal overexpressing Xyr1 (T. reesei RutC30-R3) (A) and parental filamentous fungi (T. reesei strain RutC30) (B) strains grown on 100% xylose as a carbon source atpH 3.5.

FIG. 8. The protein (solid lines) and biomass (dotted lines) accumulation, expressed in g/L, in fermentations of T. reesei P1194E(A), P1197B (B), P491P(C) and M2C38 (D) strains grown on 100% xylose as a carbon source at pH 3.5.

FIG. 13. Alignment of the amino acid sequence of T. reesei Xyr1 of SEQ ID NO:27 with the Xyr1 equivalent transcription factors from Aspergillus niger (identity 46.65%, SEQ ID 25), Aspergillus nidulans (identity 46.24%, SEQ ID 28), Aspergillus kawachii (identity 47.06%, SEQ ID 29), Aspergillus oryzae (identity 46.55%, SEQ ID 30), Aspergillus terreus (identity 42.83%, SEQ ID 31), Fusarium oxysporum identity 59.30%, SEQ ID 32), Neurospora crassa (identity 58.65%, SEQ ID 33), Penicillum canescens (identity 50.91%, SEQ ID 34), and Pyrenophora tritici-repentis (identity 42.11%, SEQ ID 35). Amino acids identical between the two sequences are indicated by the open boxes.

FIG. 14 shows the % amino acid sequence identity for the region corresponding to amino acids 343-940 of Trichoderma reesei Xyr1 with the corresponding region between pairs of Xyr1 equivalent transcription factors from Aspergillus niger, Aspergillus oryzae Aspergillus nidulans Aspergillus terreus, Aspergillus kawachii, Neurospora crassa Penicillum canescens, Fusarium oxysporum, Pyrenophora tritici-repentis and Trichoderma reesei. 343-940 amino acids of xyr1 from T.

Figure 2:
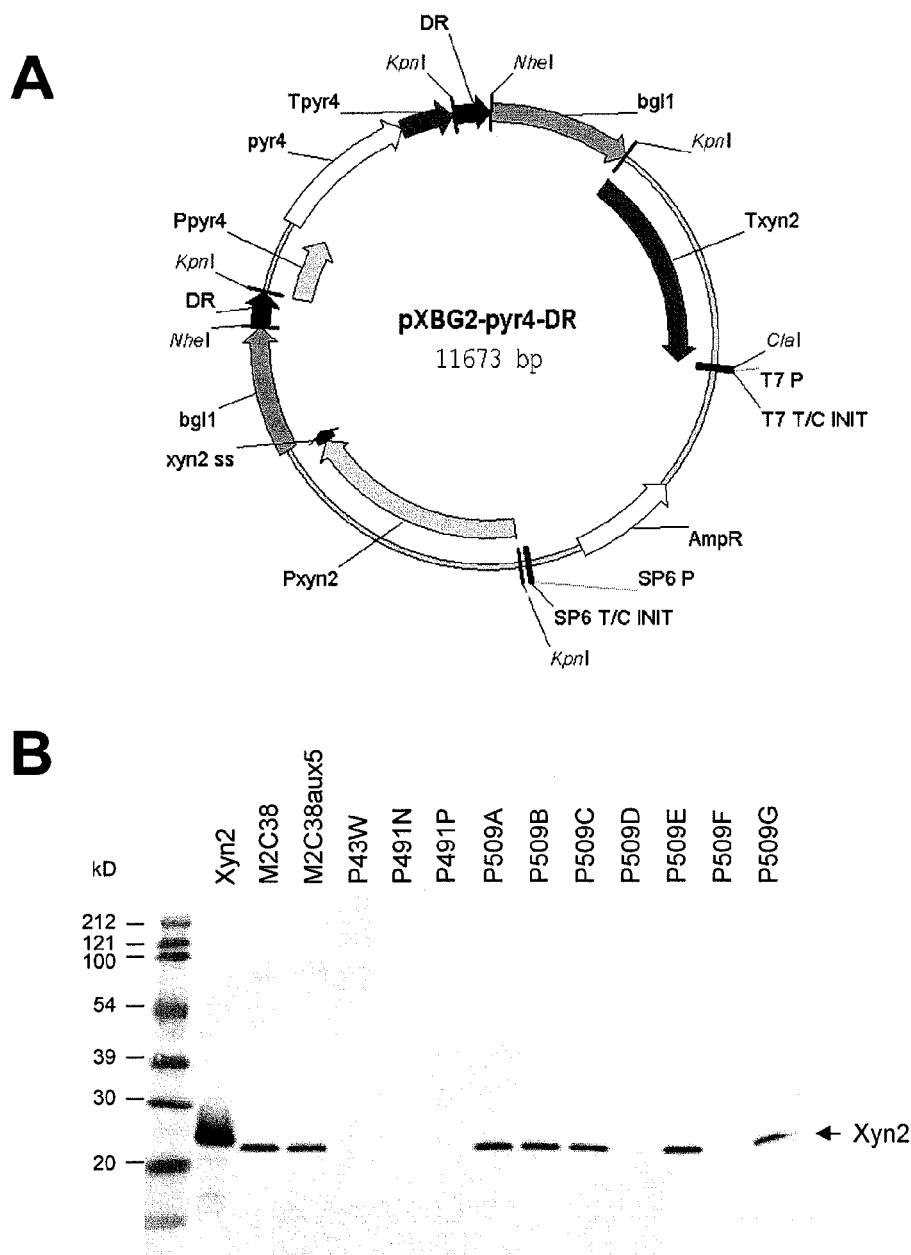
FIG. 2. A—*Trichoderma reesei* transformation vector used for xylanase 2 deletion and generation of P491P strain. B—Production of xylanase 2 in parental and transformant strains grown in microcultures on xylose as a carbon source. Aliquots (10 µg) of total secreted protein produced by parental strains (M2C38 and M2C38aux5) and transformants (P43W, P491N, P491P, P509A-G) were separated on SDS-PAGE, transferred to PVDF membrane and immunoblotted with antibodies raised against T. reesei xylanase 2. Purified Xyn2 (lane 1) was used as a control. The protein band corresponding to Xyn 2 is indicated with arrow. The weight of protein molecular weight markers is indicated in kD on the left.

reesei. The identity was calculated using DNAman program with gap penalty 3 and K-tuple 2.

DETAILED DESCRIPTION OF THE INVENTION

The present invention relates to a fermentation process for producing cellulases from a modified host filamentous fungus.

The following description is of a preferred embodiment by way of example only and without limitation to the combination of features necessary for carrying the invention into effect.

Modified Host Filamentous Fungi

Add a sentence or two about the domain structure and where the various domains start and stop The host filamentous fungus used in the fermentation process of the present invention is modified for increased expression of a Xyr1 transcription factor or a Xyr1 equivalent transcription factor. As used herein, a "Xyr1 transcription factor" is a protein belonging to zinc binuclear cluster family of fungal transcription factors and having an amino acid sequence from about 90% to about 100% identity to SEQ ID NO: 27 or demonstrating equivalent DNA binding activity as the T. reesei Xyr1. For example, the protein may have 90, 92, 94, 95, 96, 97, 98, 99 or 100% sequence identity to SEQ ID NO: 27, or any value therebetween.

As used herein, a Xyr1 equivalent transcription factor is a protein belonging to zinc binuclear cluster family of fungal transcription factors and having an amino acid sequence exhibiting from about 45% to about 99% identity to the amino acid sequence of SEQ ID NO: 27, a protein with an amino acid sequence exhibiting from about 90% to about 99% identity to the amino acid sequence of any one of SEQ ID NO: 25, SEQ ID NO: 28, SEQ ID NO: 29, SEQ ID NO: 30, SEQ ID NO: 31, SEQ ID NO: 32, SEQ ID NO: 33, SEQ ID NO: 34, or SEQ ID NO: 35 or a protein containing a zinc binuclear cluster that that possesses equivalent DNA binding activity specific to a consensus sequence GGC(T/A)$_3$-like motif within cellulase and/or hemicellulase promoter sequences as the protein with the amino acid sequence of SEQ ID NO: 27.

FIG. 13 shows an alignment of the T. reesei Xyr1 transcription factor of SEQ ID NO: 27 with Xyr1 equivalent transcription factors from other fungal species. All of these enzymes exhibit from about 42% to about 59% amino acid sequence identity to SEQ ID NO: 27 (Table 1). Further, as shown in FIG. 14, amino acids corresponding to amino acids 343-940 of Trichoderma reesei Xyr1 in Xyr1 equivalent transcription factors from other cellulolytic filamentous fungi of the Subphylum Pezizomycotina exhibit from about 48% to about 66% identity to amino acids 343-940 of T. reesei Xyr1 (SEQ ID NO: 27).

TABLE 1

Xyr1 equivalent transcription factors

| Source organism | Sequence Identifier | Identity to T. reesei Xyr1 (SEQ ID NO: 27) |
|---|---|---|
| Aspergillus niger | SEQ ID NO: 25 | 46.65% |
| Aspergillus nidulans | SEQ ID NO: 28 | 46.24% |
| Aspergillus kawachii | SEQ ID NO: 29 | 47.06% |
| Aspergillus oryzae | SEQ ID NO: 30 | 46.55% |
| Aspergillus terreus | SEQ ID NO: 31 | 42.83% |
| Fusarium oxysporum | SEQ ID NO: 32 | 59.30% |
| Neurospora crassa | SEQ ID NO: 33 | 58.65% |
| Penicillum canescens | SEQ ID NO: 34 | 50.91% |
| Pyrenophora tritici-repentis | SEQ ID NO: 35 | 42.11% |

Methods to align amino acid sequences and determine sequence identity between amino acid sequences are well known and available to those of skill in the art and include BLAST (Basic Local Alignment Search Tool, see Altschul et al., J. Mol. Biol. 215:403-410, 1990) which is useful for aligning two sequences and CLUSTALW for alignment of two or more sequences. Sequence identity may also be determined by manual alignment and visual inspection.

By "equivalent DNA binding activity" it is meant the DNA binding of the Xyr1 or Xyr1 equivalent transcription factor to the GGC(T/A)$_3$-like consensus motif mediated by a $Zn_2Cys_6$ zinc binuclear cluster or zinc finger domain. This cluster is well-conserved in all members of fungal zinc binuclear cluster protein family and consists of the amino acid motif Cys Xaa(2) Cys Xaa(6) Cys Xaa(5-12) Cys Xaa(2), Cys Xaa(6-8), Cys. In addition, the DNA consensus sequence recognized by the zinc binuclear cluster in the Xyr1 or Xyr1 equivalent transcription factor may be present as a single, double or triple repeat within regulated gene promoter(s). The Xyr1 or Xyr1 equivalent transcription factor may bind to the described gene promoter sequences either as a monomer or as a protein complex in either homo- or heterodimeric forms. without wishing to be bound by theory, the Xyr1 or Xyr1 equivalent transcription factor may interact with other gene-specific and/or general transcriptional factors such as Ace1 and Ace2 proteins during DNA binding. DNA binding activity of a Xyr1 or Xyr1 equivalent transcription factor to a GGC(T/A)$_3$-like consensus motif may be measured using one or more methods known to one of skill in the art including electrophoretic mobility-shift assay (EMSA) or DNA footprinting. Such methods are described in Furukawa, et al. 2009.

For the purpose described herein, "increased expression" or "overexpression" means at least about a 50% increase in the level of transcript for a given gene in the modified host filamentous fungus as compared to the level of transcript for the same gene in the parental filamentous fungus when grown under identical conditions of medium composition, temperature, pH, cell density and age of culture.

For the purposes described herein, by the term "parental filamentous fungus", when used in the context of determining the expression level of the Xyr1 gene, it is meant a filamentous fungus that has not been genetically modified so as to increase expression of a Xyr1 or Xyr1 equivalent transcription factor, but which is otherwise identical to the modified host filamentous fungus.

Increased expression or overexpression of the Xyr1 or Xyr1 equivalent transcription factor may be achieved by methods known to those of skill in the art, including classical mutation and selection or genetic engineering. For example, a host cell may be genetically engineered for increased expressed of a Xyr1 or Xyr1 equivalent transcription factor by transformation of the host cell with a Xyr1 genetic construct.

As used herein, "genetic construct" refers to an isolated nucleic acid sequence comprising the nucleic acid elements necessary for the expression of a protein and the selection of host cells containing the genetic construct. These elements include, but are not limited to, a coding region comprising a nucleic acid sequence that encodes a protein product, and a promoter, comprising a nucleic acid sequence that directs the transcription of a coding region. As understood by one of ordinary skill in the art, these nucleic acid elements may be derived from the host cell or from a different organism, and/or be synthesized in vitro. These nucleic acid sequence elements may also be altered or engineered by replacement, substitution, addition, or elimination of one or more nucleic acids.

The practice of this invention is not constrained by the source of or any such alterations to the nucleic acid elements comprising the genetic construct A "Xyr1 genetic construct" refers to an isolated nucleic acid sequence comprising a coding region for a Xyr1 or Xyr1 equivalent transcription factor operably linked to a promoter. For example, the promoter may be derived from a gene that is highly expressed when the host cell is grown with a carbon source comprising HDC. For example, if the host filamentous fungus is *T. reesei*, the promoter nucleic acid sequence may be derived from one or more *T. reesei* genes encoding beta-xylosidase (JGI Protein ID 3264), beta-xylosidase 2 (JGI Protein ID 105276), xylanase 1 (JGI Protein ID 74223), xylanase 2 (JGI Protein ID 23246) o rxylanase 3 (JGI Protein ID 2034), or any combination thereof. Alternatively, the promoter may be derived from a gene that is constitutively expressed. An example of a constitutive promoter in *T. reesei* is that derived from the phosphoglycerate kinase (pgk) gene. However, it should be understood that the practice of the present invention is not limited by the choice of promoter in the Xyr1 genetic construct.

As used herein with respect to nucleic acid sequence, "isolated" means altered from its natural state by virtue of separating the nucleic acid sequence from some or all of the naturally-occurring nucleic acid sequences with which it is associated in nature.

As used herein, in respect of nucleic acid sequence elements, "derived from" refers to the isolation of a target nucleic acid sequence element using one or more molecular biology techniques known to those of skill in the art including, but not limited to, cloning, sub-cloning, amplification by PCR, in vitro synthesis, and the like. The term "derived from" applies to both modified and native (or wild-type) nucleic acid sequence elements. In the case of native nucleic acid sequence elements, "derived from" refers to the isolation of a target nucleic acid sequence element without the introduction of one or more insertions, deletions, or substitutions to the target nucleic acid sequence elements as it is found in nature other than those that may be necessary to add to the 5' and 3' ends of the isolated element to facilitate cloning. In the case of modified nucleic acid sequence elements, "derived from" would also include the introduction of one or more insertions, deletions or substitutions to the wild-type or native sequence.

A genetic construct may contain a selectable marker for determining transformation of a host cell. The selectable marker may be present on the Xyr1 or other genetic construct or the selectable marker may be a separate isolated nucleic acid that is co-transformed with the genetic construct. Choices of selectable markers are well known to those skilled in the art and include genes (synthetic or natural) that confer to the transformed cells the ability to utilize a metabolite that is not normally metabolized by the microbe (e.g., the *A. nidulans* amdS gene encoding acetamidase and conferring the ability to grow on acetamide as the sole nitrogen source) or antibiotic resistance (e.g., the *Escherichia coli* hph gene encoding hygromycin-beta-phosphotransferase and conferring resistance to hygromycin). If the host strain lacks a functional gene for the marker chosen, then that gene may be used as a marker. Examples of such markers include trp, pyr4, pyrG, argB, leu, and the like. The corresponding host strain would therefore have to be lacking a functional gene corresponding to the marker chosen, i.e., lacking in the expression of trp, pyr, arg, leu and the like.

A genetic construct may contain a transcriptional terminator that is functional in the host cell, as would be known to one of skill in the art. The transcriptional terminator may be positioned immediately downstream of a coding region. The practice of the invention is not constrained by the choice of transcriptional terminator that is sufficient to direct the termination of transcription by an RNA polymerase in the host cell.

The fungal cell may be modified with additional genetic constructs so as to enhance or reduce the expression and secretion of one or more homologous or heterologous proteins. For example, the fungal cell may be modified so as to over express a beta-glucosidase enzyme according to U.S. Pat. No. 6,015,703. The host cell may also be modified so as to produce an optimized blend of cellulase components and accessory components according to co-pending U.S. Publication No. US 2008/0057541 A1 and U.S. Patent Application No. 60/969,046. For example, the fungal cell may be modified with one or more genetic constructs comprising a gene encoding a cellulase enzyme operably linked to a promoter regulated by a Xyr1 transcription factor, such as a promoter from a cellulase or xylanase gene. The practice of the present invention is not limited by whether the additional genetic constructs directing the expression and secretion of the one or more homologous or heterologous proteins have been introduced previously to, simultaneously with, or subsequently to the modification that results in the overexpression of a Xyr1 or Xyr1 equivalent transcription factor.

Such genetic constructs that encode for the expression and secretion of a protein other than a Xyr1 or Xyr1 equivalent transcription factor, further comprise a secretion signal sequence. As used herein, a "secretion signal sequence" is a nucleic acid sequence encoding a peptide sequence present at the amino terminus of a secreted protein that directs entry of the protein into the endoplasmic reticulum (ER); the secretion signal may subsequently be cleaved from the mature secreted protein by a signal peptidase.

The modified host filamentous fungus used in the fermentation process of the present invention may be partially or completely deficient in the production of one or more hemicellulase enzymes such as xylanases, beta-xylosidases, arabinofuranosidases, mananases, alpha-glucuronidases, acetylxylan esterases, or a combination thereof. The modified host filamentous fungus additionally overexpresses a Xyr1 or Xyr1 equivalent transcription factor. However, it should be understood that the modified host filamentous fungus may be made partially or completely deficient in the expression of one or more hemicellulase enzymes previous to, simultaneous with, or subsequent to the modification that results in the overexpression of the Xyr1 or Xyr1 equivalent transcription factor.

By "partially or completely deficient in expressing one or more hemicellulase enzyme", it is meant that the cellulase mixture secreted by the modified host filamentous fungus exhibits from about a 50% to about a 100% decrease in the relative proportion of at least one hemicellulase component as compared to relative proportion of the same hemicellulase component in a cellulase mixture produced by a corresponding hemicellulase deficient parental filamentous fungus when grown under identical conditions of medium composition, temperature, pH, cell density and age of culture. For example, the modified host filamentous fungus may exhibit a 50%, 55%, 60%, 65%, 70%, 75%, 80%, 85%, 90%, 95% or 100% decrease in the relative proportion of one or more hemicellulase enzyme as to relative proportion of the same hemicellulase component in a cellulase mixture produced by the corresponding hemicellulase deficient parental filamentous fungus when grown under identical conditions of medium composition, temperature, pH, cell density and age of culture.

When used in the context of determining the proportion of a hemicellulase enzyme in a cellulase mixture, a "hemicellulase deficient parental filamentous fungus" is a filamentous fungus that has not been genetically modified so as to exhibit a partial or complete deficiency in expressing the same one or more hemicellulase enzymes of whose expression the modified host filamentous fungus has been made to be partially or completely deficient.

Partial or complete deficiency in the expression of one or more hemicellulase enzymes can be achieved in a number of different ways known to one of ordinary skill in the art. For example, mutations may be introduced into one or more hemicellulase genes (insertion, deletion, or both) in the modified host filamentous fungus. In a non-limiting example, the modified host filamentous fungus contains deletion of the gene encoding either xylanase 2 or beta-xylosidase 1, or a double deletion of both.

Partial or complete deficiency in the expression of one or more hemicellulase enzymes may also be achieved by modifying the expression or function of a functional hemicellulase-specific transcriptional regulator(s). In the case of positive regulators or activators, the encoding gene sequence may be deleted or altered to as to produce a regulator with reduced activity. In the case of negative regulators or repressors, the encoding gene may be overexpressed or altered so as to produce a regulator with enhanced activity. For example, the coding sequence(s) of hemicellulase-specific transcriptional regulator gene(s) may by modified by insertion, deletion or both and/or the gene(s) encoding the hemicellulase-specific transcriptional regulator may also contain amino acid substitutions which modify protein function so as to reduce or enhance its DNA-binding activity, its interaction with other transcriptional regulators, its nuclear localization and the like.

Deleting a nucleic acid sequence may be achieved by engineering a construct that includes sequences from the target nucleic acid sequence itself into the construct, but in altered form. After transformation of the construct into the expression host, recombination then occurs with the altered target nucleic acid sequence, resulting in the insertion of the altered sequence to disrupt the native nucleic acid sequence. With its sequence interrupted, the altered gene in most cases will be translated into a nonfunctional protein, or not translated at all. An example of a method that may be used to delete a target nucleic acid sequence from a host cell include, but are not limited to, methods described in U.S. Pat. No. 5,298,405, which is incorporated herein by reference.

Hemicellulase deficiency may also be achieved by chemical or physical (for example UV) mutagenesis and selection of non-hemicellulase producing cells. In addition, the hemicellulase deficient cells may be isolated as a result of naturally occurring spontaneous mutations or inherited hemicellulase gene silencing.

A genetic construct may contain additional sequences between the various nucleic acid elements as described herein. These sequences, which may be natural or synthetic, may result in the addition of one or more of the amino acids to the protein encoded by the construct. The practice of the invention is not constrained by the presence of additional DNA sequences between the various nucleic acid elements of the genetic constructs present in the host cell.

The practice of the present invention is not constrained by the method of introducing the genetic constructs into the host cell. Methods of introducing the DNA construct into a host cell are familiar to those skilled in the art and include, but are not limited to, calcium chloride treatment of bacterial cells or fungal protoplasts to weaken the cell membranes, addition of polyethylene glycol to allow for fusion of cell membranes, depolarization of cell membranes by electroporation, or shooting the DNA through the cell wall and membranes via microprojectile bombardment with a particle gun.

Culture Medium

In the fermentation process of the present invention, the culture medium comprises a carbon source, a nitrogen source (either or both inorganic and organic in nature), and other essential minerals and nutrients as known by one of skill in the art. Organic nitrogen sources such as amino acids and peptides may also be utilized as sources of carbon; however, these organic nitrogen sources are not included in the calculation of carbon source supplied to the host cell during the fermentation process.

In a first embodiment, the carbon source supplied to the fungal cells in the fermentation process of the present invention comprises hemicellulose-derived carbohydrate (HDC). As used herein, the term hemicellulose-derived carbohydrate or HDC refers to one or more oligo-, di- or mono-saccharide that may be released by the chemical or enzymatic depolymerization of hemicellulose and which can be utilized by the host microbe for growth, enzyme production or both. Non-limiting examples of HDC include xylo-oligosaccharides, arabinoxylo-oligosaccharides, D-xylose, xylobiose, L-arabinose, D-mannose D-galactose and combinations thereof. For example, the HDC contains D-xylose and/or L-arabinose. The HDC represents from about 60 wt % to about 100 wt % of the carbon source fed to the fungal cells during the fermentation process. For example, the HDC may represent 60, 65, 70, 75, 80, 85, 90, 95, 97, 98, 99 or 100 wt % or any amount therebetween, of the carbon sources fed to the fungal cells during the fermentation process. For example, the HDC may represent from about 80% to about 100% of the carbon source fed to the fungal cells during the fermentation process.

In a second embodiment, the carbon source supplied to the fungal cells in the fermentation process of the present invention comprises hemicellulose-derived sugar alcohol (HDSA), glycerol and/or glucose. As used herein, the term hemicellulose-derived sugar alcohol or HDSA refers to one or more sugar alcohols that may be derived from oligo-, di- or mono-saccharide released by the chemical or enzymatic depolymerization of hemicellulose and which can be utilized by the host microbe for growth, enzyme production or both. Non-limiting examples of HDSA include xylitol, mannitol, arabinitol, galactictol and combinations thereof. Preferably, the HDSA is xylitol or arabinitol. The HDSA represents from about 25 wt % to about 100 wt % of the carbon source fed to the fungal cells during the fermentation process. For example, the HDSA may represent 25, 30, 40, 50, 55, 60, 65, 70, 75, 80, 85, 90, 95, 97, 98, 99 or 100 wt % or any amount therebetween, of the carbon sources fed to the fungal cells during the fermentation process. For example, the HDC may represent from about 80% to about 100% of the carbon source fed to the fungal cells during the fermentation process. In addition to HDSA, the carbon source also contains about 0 wt % of a cellulase-inducing carbohydrate and from about 0 wt % to about 75 wt % glucose, glycerol or a combination thereof.

In addition to HDC or HDSA, the carbon source supplied to the fermentation process of the present invention also comprises from about 0 to about 3 wt %, or any amount therebetween, of a cellulose-inducing carbohydrate (CIC). As used herein, the term cellulose-inducing carbohydrate or CIC refers to one or more oligo- or di-saccharide that leads to the induction of cellulase production by the host cell. By induction, it is meant the switching on of the expression of one or more cellulase genes in response to the CIC. Non-limiting examples of cellulase-inducing carbohydrates include cellulose, lactose, cellobiose, sophorose, gentiobiose, and a combination thereof. Cellulase-inducing carbohydrate (CIC) may be produced by enzymatic conversion of cellulose with one or more cellulase enzymes to beta-linked glucose dimers. Alternatively, a high concentration glucose syrup can be condensed chemically or enzymatically to form mixtures of glucose dimers. For example, the condensation reaction to convert glucose to CIC may be catalyzed by dilute acid and performed at temperatures above 120-150° C., or by beta-glucosidase or cellulase enzymes at more moderate temperatures of about 40-70° C. (U.S. Publication No. US2004/0121446A1).

In addition to HDC and CIC, from about 0.1 to about 40 wt %, or any amount therebetween, of the carbon source supplied to the host cell during the fermentation process may comprise one or more of glucose, glycerol, sugar alcohols (such as xylitol or arabinitol), organic acids (such as acetic acid or glucuronic acid) or other carbon sources that can be utilized by the host cell. For example, from about 0.1, 0.2, 0.5, 0.8, 1.0, 1.5, 2.0, 2.5, 3.0, 3.5, 4.0, 4.5, 5.0, 7.0, 8.0, 10.0, 15, 20, 25, 30, 35, 40%, or any amount therebetween, of the total carbon supplied to the host cell during the fermentation process may comprise one or more of glucose, glycerol, sugar alcohols (such as xylitol or arabinitol), organic acids (such as acetic acid or glucuronic acid) or other carbon sources that can be utilized by the host cell.

One of skill in the art is aware that other nutrients, vitamins and minerals can be added to the fermentation media to improve growth and enzyme production of the host cell. These other media components may be added prior to, simultaneously with or after inoculation of the culture with the host cell.

Producing Cellulase Mixtures

Cellulase mixtures are typically produced by subjecting an actively growing fungal culture to media (solid or liquid) containing little or no glucose and a cellulase-inducing carbohydrate, as well as other nutrients required for cell growth, at temperatures and pH suitable for the host cell. In the fermentation process of the present invention, cellulase mixtures are produced by subjecting an actively growing culture of a modified host filamentous fungus overexpressing a Xyr1 to media (solid or liquid) a carbon source containing from about 60 wt % to about 100 wt % hemicellulose-derived carbohydrate and from about 0 wt % to about 3 wt % of a cellulase-inducing carbohydrate or in a medium comprising a carbon source containing from about 25 wt % to about 100 wt % of a hemicellulose-derived sugar alcohol, about 0% cellulase-inducing carbohydrate and from about 0 wt % to 75 wt % glucose, glycerol or a combination thereof Expression of cellulases may be detected at the level of transcription by techniques known to those of ordinary skill in the art, including, but not limited to, Northern blot hybridization or quantitative real time PCT (qRT-PCR; see Example 1.3). Expression of the cellulase protein may be detected by several methods known to those of skill in the art including enzyme activity assays or protein immunodetection. Non-limiting examples of activity and immunodetection methods for cellulase mixtures are provided in Example 7.

Submerged liquid fermentations of *Trichoderma* and related filamentous fungi are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. In a batch fermentation, the carbon source may be added to the fermentation medium prior to or simultaneously with inoculation.

In a fed-batch process, the culture is fed continuously or sequentially with one or more media components with the removal of the culture fluid. In a continuous process, fresh medium is supplied and culture fluid is removed continuously at volumetrically equal rates to maintain the culture at a steady growth rate. In the cases of fed-batch or continuous operations, the carbon source may also be supplied continuously or intermittently during the fermentation process. Preferably, the feed rate is between 0.2 and 2.5 g carbon/L of culture/h, or any amount therebetween. More preferably, the feed rate is between 0.4 and 1.6 g carbon/L of culture/h, or any amount therebetween.

The fermentation process of the present invention may be carried at a temperature from about 20° C. to about 35° C., or any temperature therebetween, for example from about 25° C. to about 30° C., or any temperature therebetween, or from 20, 22, 25, 26, 27, 28, 29, 30, 32, 35° C., or any temperature therebetween.

The fermentation process of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

The fermentation process of the present invention may be carried out over a period of 3-30 days, or any amount therebetween, for example between 3 and 10 days, or any amount therebetween, between 4 and 8 days, or any amount therebetween, or from 3, 4, 5, 6, 7, 8, 9, 10, 12, 14, 16, 18, 20, 22, 24, 26, 28, 30 days, or any amount therebetween.

The fermentation process of the present invention may be performed in cultures of at least 1 litre, for example from about 1 to about 400,000 liters, or any amount therebetween, for example, 10 to about 400,000 litres, or any amount therebetween, 1,000 to about 200,000 litres, or any amount therebetween, or 10,000 to about 200,000 litres, or any amount therebetween, or from about 1, 10, 50, 100, 200, 400, 600, 800, 1000, 2000, 4000, 6000, 8000 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 300,000, 400,000 litres in volume, or any amount therebetween.

The fermentation process of the present invention may be performed aerobically, in the presence of oxygen, or anaerobically, in the absence of oxygen. Preferably, the process is performed aerobically.

Following fermentation, the cellulase mixture thus produced may be used directly, or the cellulase mixture may be separated from the fungal cells, for example by filtration or centrifugation. Low molecular solutes such as unconsumed components of the fermentation medium may be removed by ultrafiltration. The cellulase mixture maybe concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase mixture to prevent growth of microbial contaminants.

The fermentation process of the present invention may produce a cellulase mixture containing at least about 2-fold more secreted protein than a corresponding process in which the carbon source contains only HDC and is performed using a fungal strain that has not been modified or selected for increased expression of a Xyr1 or Xyr1 equivalent transcription factor. For example the process described herein may produce 2.5 to about 10 fold more, or any amount therebetween, for example about 2.5, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, 10 fold more secreted protein, or any amount therebetween or more than 10 fold more secreted protein, than a corresponding process in which the carbon source contains only HDC and is performed using a fungal strain that has not been modified or selected for increased expression of a Xyr1 or Xyr1 equivalent transcription factor. Thus, the fermentation process may be characterized by having from about a 2-fold, for example from about a 5-fold, or any amount therebetween, increase in specific productivity ($q_p$) in terms of mg secreted cellulase produced/g biomass/h than a corresponding process in which the carbon source contains only HDC and is performed using a fungal strain that has not been modified or selected for increased expression of a Xyr1 or Xyr1 equivalent transcription factor. An increase in specific productivity of protein production in the presence of varying amount of HDC, cellulose inducing carbohydrate (CIC), or both HDC and CIC as described herein, is shown in Table 2.

For example, cellulase components may represent from about 40, 45, 50, 55, 60, 65, 70, 75, 80, 85, 90, 95 or 100 wt % of the total protein in the cellulase mixture, or any amount therebetween. The relative proportion of cellulase components in cellulase mixtures produced by modified host filamentous fungi using the fermentation process of the present invention are shown in Table 3.

As used herein, the term "cellulase component" or "cellulase components" includes endoglucanases (E.C. 3.2.1.4), cellobiohydrolases (E.C. 3.2.1.91), beta-glucosidase (E.C. 3.2.1.21), and mixtures thereof. The terms "cellulase component" or "cellulase components" also includes other proteins, such as swollenins, that are involved in or enhance the enzymatic degradation of cellulose. It should be understood that the practice of the present invention is not limited by the identity of the cellulase component(s) in the cellulase mixture. Cellulase components are part of a broader family of

TABLE 2

Production of protein and fungal cells from submerged liquid cultures of parental and modified filamentous fungi on various carbon sources

| | | | | | Fermentation profile | | | |
|---|---|---|---|---|---|---|---|---|
| | Strain Information and Fermentation Feed | | | | Final protein, | Final biomass, | Avg qp, | Max qp, |
| Ferm# | Strain | xyr1 | xyn2 | Fermentation Feed | g/L | g/L | mg/g/h | mg/g/h |
| 2404 | P285-6 | wt | wt | H2 | 37.44 | 14.29 | 22.42 | 41.68 |
| 3964 | P285-6 | wt | wt | | 32.42 | 13.87 | 19.46 | 43.66 |
| 3796 | P692B | xyr1+ | wt | | 30.41 | 14.14 | 20.62 | 34.97 |
| 3963 | P692B | xyr1+ | wt | | 34.31 | 13.77 | 22.98 | 45.74 |
| 3685 | P285-6 | wt | wt | 100% Xylose | 5.93 | 38.79 | 3.05 | 7.22 |
| 3951 | P285-6 | wt | wt | | 8.24 | 37.34 | 3.07 | 5.35 |
| 3684 | P692B | xyr1+ | wt | | 35.20 | 16.00 | 21.60 | 29.00 |
| 3950 | P692B | xyr1+ | wt | | 35.03 | 14.70 | 20.55 | 38.04 |
| 4254 | P692A | xyr1+ | wt | | 28.21 | 22.31 | 13.71 | 23.32 |
| 4000 | P285-6 | wt | wt | 100% Arabinose | 9.17 | 35.01 | 3.13 | 6.96 |
| 3735 | P285-6 | wt | wt | | 7.91 | 34.55 | 1.73 | 7.75 |
| 3734 | P692B | xyr1+ | wt | | 31.87 | 25.60 | 11.67 | 16.75 |
| 3980 | P692B | xyr1+ | wt | | 21.78 | 27.25 | 10.21 | 15.18 |
| 4217 | P285-6 | wt | wt | 50% glucose/ | 3.34 | 37.48 | 1.37 | 5.54 |
| 4042 | P692B | xyr1+ | wt | 25% glycerol/ | 29.11 | 23.26 | 15.38 | 26.61 |
| 4086 | P692B | xyr1+ | wt | 25% xylitol | 27.8 | 22.08 | 13.58 | 20.49 |
| 4218 | P285-6 | wt | wt | 50% glucose/ | 6.07 | 32.67 | 2.53 | 5.43 |
| 4043 | P692B | xyr1+ | wt | 25% glycerol/ | 32.65 | 19.74 | 15.84 | 23.95 |
| 4087 | P692B | xyr1+ | wt | 25% xylose | 27.31 | 25.15 | 12.78 | 23.05 |
| 4279 | RutC30 | wt | wt | H2 | 14.97 | 8.46 | 7.35 | 13.55 |
| 4280 | RutC30-R3 | xyr1+ | wt | | 27.50 | 20.35 | 12.14 | 16.79 |
| 4073 | RutC30 | wt | wt | 100% Xylose | 2.50 | 55.33 | 1.06 | 3.11 |
| 4074 | RutC30-R3 | xyr1+ | wt | | 35.13 | 31.70 | 13.44 | 21.05 |
| 4255 | RutC30-R3 | xyr1+ | wt | | 37.38 | 26.57 | 15.45 | 23.33 |
| 4258 | M2C38 | wt | wt | | 7.66 | 29.86 | 3.51 | 8.36 |
| 4101 | P491P | wt | xyn2– | | 6.11 | 40.35 | 2.39 | 6.81 |
| 4120 | P1194E | xyr1+ | xyn2– | | 25.15 | 28.11 | 10.95 | 19.74 |
| 4121 | P1194F | xyr1+ | xyn2– | | 24.13 | 27.00 | 10.55 | 19.92 |
| 4122 | P1197B | xyr1+ | xyn2– | | 22.92 | 27.51 | 9.95 | 18.54 |
| 4403 | RutC30-R3 | xyr1+ | wt | 50% glucose/ 25% glycerol/ 25% xylitol | 15.17 | 11.61 | 6.04 | 12.05 |
| 4404 | P692B | xyr1+ | wt | 99% Xylose/1% J1 | 27.13 | 7.60 | 15.72 | 29.61 |
| 4417 | P692B | xyr1+ | wt | 97% Xylose/3% J1 | 39.47 | 13.84 | 20.89 | 29.91 |

<sup>a</sup>CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates Cellulase Mixtures The fermentation process of the present invention produces a cellulase mixture. As used herein, a "cellulase mixture" is a mixture comprising cellulase components, hemicellulase components and other protein secreted by the modified host filamentous fungus during the fermentation process. The cellulase mixture produced by the fermentation process comprises from about 40 to about 100 wt % cellulase components relative to the total protein present in the cellulase mixture.

enzymes referred to as glycosyl hydrolases. Glycosyl hydrolases are divided into different families and are listed in the database for Carbohydrate-Active Enzymes (Coutinho, P. M. & Henrissat, B., 1999. This database and nomenclature are familiar to those skilled in the art. Cellulase components are most commonly found as members of glycosyl hydrolase families 1, 3, 5, 6, 7, 12, 45 or 61. As it relates to the native cellulase mixture produced by T. reesei, the term "cellulase component(s)" refers to some or all of the following: cellobiohydrolase 1 (Cel7A), cellobiohydrolase 2 (Cel6A), endoglucanase 1 (Cel7B), endoglucanase 2 (Cel5A), endoglucanase 3 (Cel12A), endoglucanase 4 (Cel61A), endoglucanase 5 (Cel45A), beta-glucosidase 1 (Cel3A) and beta-glucosidase 2 (Cel3B), CipI and Swollenin.

Enzymes involved in the degradation hemicelluloses are referred to herein as "hemicellulases" or "hemicellulase components" (reviewed in Saha, B. C. (2003). Hemicellulases include, but are not limited to, endo-xylanases (E.C. 3.2.1.8), beta-xylosidases (E.C. 3.2.1.37), alpha-arabinofuranosidases (E.C. 3.2.1.55), alpha-glucuronidases (E.C. 3.2.1.139), acetylxylan esterases (E.C. 3.1.1.72), ferulic acid esterases (E.C. 3.1.1.73), beta-mannanases (E.C. 3.2.1.78), and beta-mannosidases (3.2.1.15). Xylans are the most abundant hemicelluloses. The term "xylanases" or "xylanase components" as used herein refers to enzymes that have endo-xylanase, exo-xylanase or beta-xylosidase activity. Xylanases may belong to glycosyl hydrolase families 3, 5, 10 and 11. As it relates to the native cellulase mixture produced by *T. reesei*, the term "xylanase" or "xylanase components" refers to some or all of the following enzymes from *Trichoderma reesei*: beta-xylosidase 1 (Bxl1), beta-xylosidase 2 (Bxl2), xylanase 1 (Xyn1), xylanase 2 (Xyn2), xylanase 3 (Xyn3) and xylanase 4 (Xyn4).

TABLE 3

Composition of cellulase mixtures secreted from submerged liquid cultures of parental (and modified host filamentous fungi on various carbon sources.

| | Strain Information and Fermentation Feed | | | | Composition of Secreted Enzyme (wt % total protein) | | | Relative |
|---|---|---|---|---|---|---|---|---|
| Ferm# | Strain | xyr1 | xyn2 | Carbon Source | Cellulase [a] | Xylanase [b] | Beta-xylosidase [c] | Activity [d] |
| 2404 | P285-6 | wt | wt | 65% glucose + | 69.4 | — | Nd | 1.00 ± 0.02 |
| 3964 | P285-6 | wt | wt | 35% CIC | 71.9 | — | Nd | 0.98 ± 0.03 |
| 3796 | P692B | xyr1+ | wt | | 80.6 | — | Nd | 1.09 ± 0.03 |
| 3963 | P692B | xyr1+ | wt | | 64.8 | — | Nd | 1.05 ± 0.03 |
| 3685 | P285-6 | wt | wt | 100% xylose | 14.3 | 25.4 | 31.9 | 0.12 ± 0.02 |
| 3951 | P285-6 | wt | wt | | 11.8 | 27.4 | 34.0 | 0.07 ± 0.03 |
| 3684 | P692B | xyr1+ | wt | | 54.4 | 21.3 | 1.8 | 0.55 ± 0.02 |
| 3950 | P692B | xyr1+ | wt | | 49.4 | 23.9 | 1.6 | 0.68 ± 0.04 |
| 4254 | P692A | xyr1+ | wt | | 46.6 | 18.4 | 1.9 | 0.39 ± 0.03 |
| 4000 | P285-6 | wt | wt | 100% arabinose | 20.6 | 27.2 | 12.3 | 0.21 ± 0.03 |
| 3735 | P285-6 | wt | wt | | 28.3 | 35.6 | 10.6 | 0.23 ± 0.03 |
| 3734 | P692B | xyr1+ | wt | | 47.9 | 14.4 | 5.8 | 0.46 ± 0.03 |
| 3980 | P692B | xyr1+ | wt | | 40.6 | 23.5 | 2.6 | 0.57 ± 0.04 |
| 4217 | P285-6 | wt | wt | 25% xylitol/ | 58.8 | 5.6 | 3.1 | 0.43 ± 0.03 |
| 4042 | P692B | xyr1+ | wt | 50% glucose/ | 64.8 | 4.1 | 0.4 | 0.74 ± 0.06 |
| 4086 | P692B | xyr1+ | wt | 25% glycerol | 64.1 | 4.7 | 0.7 | 0.71 ± 0.03 |
| 4218 | P285-6 | wt | wt | 25% xylose/ | 29.3 | 30.5 | 20.7 | 0.21 ± 0.04 |
| 4043 | P692B | xyr1+ | wt | 50% glucose/ | 45.7 | 16.3 | 2.1 | 0.44 ± 0.07 |
| 4087 | P692B | xyr1+ | wt | 25% glycerol | 39.8 | 13.1 | 4.5 | 0.40 ± 0.03 |
| 4279 | RutC30 | wt | wt | 65% glucose + | 86.6 | 1.4 | Nd | 1.00 ± 0.08 |
| 4280 | RutC30-R3 | xyr1+ | wt | 35% CIC | 85.5 | — | Nd | 1.12 ± 0.08 |
| 4073 | RutC30 | wt | wt | 100% xylose | 18.5 | 13.7 | 20.1 | 0.20 ± 0.06 |
| 4074 | RutC30-R3 | xyr1+ | wt | | 52.9 | 6.4 | 1.7 | 1.36 ± 0.08 |
| 4255 | RutC30-R3 | xyr1+ | wt | | 71.5 | 6.4 | 1.1 | 0.99 ± 0.04 |
| 4258 | M2C38 | wt | wt | | 47.5 | 21.5 | 7.7 | 0.41 ± 0.06 |
| 4101 | P491P | wt | xyn2− | | 29.5 | 14.6 | 20.0 | 0.38 ± 0.05 |
| 4120 | P1194E | xyr1+ | xyn2− | | 62.6 | 10.9 | 4.0 | 0.84 ± 0.06 |
| 4121 | P1194F | xyr1+ | xyn2− | | 58.6 | 10.2 | 4.5 | 0.78 ± 0.05 |
| 4122 | P1197B | xyr1+ | xyn2− | | 59.0 | 11.0 | 4.1 | 0.74 ± 0.06 |
| 4403 | RutC30-R3 | xyr1+ | wt | 25% xylitol/ 50% glucose/ 25% glycerol | 82.3 | 1.1 | — | 1.22 ± 0.05 |

[a] CIC for these fermentations was inducing cocktail comprising, as a function of total carbohydrate, 56% gentiobiose, 14% sophorose, 6% cellobiose, 10% trehalose, 6% maltotriose, 4% glucose and 14% other carbohydrates

Figure 12:
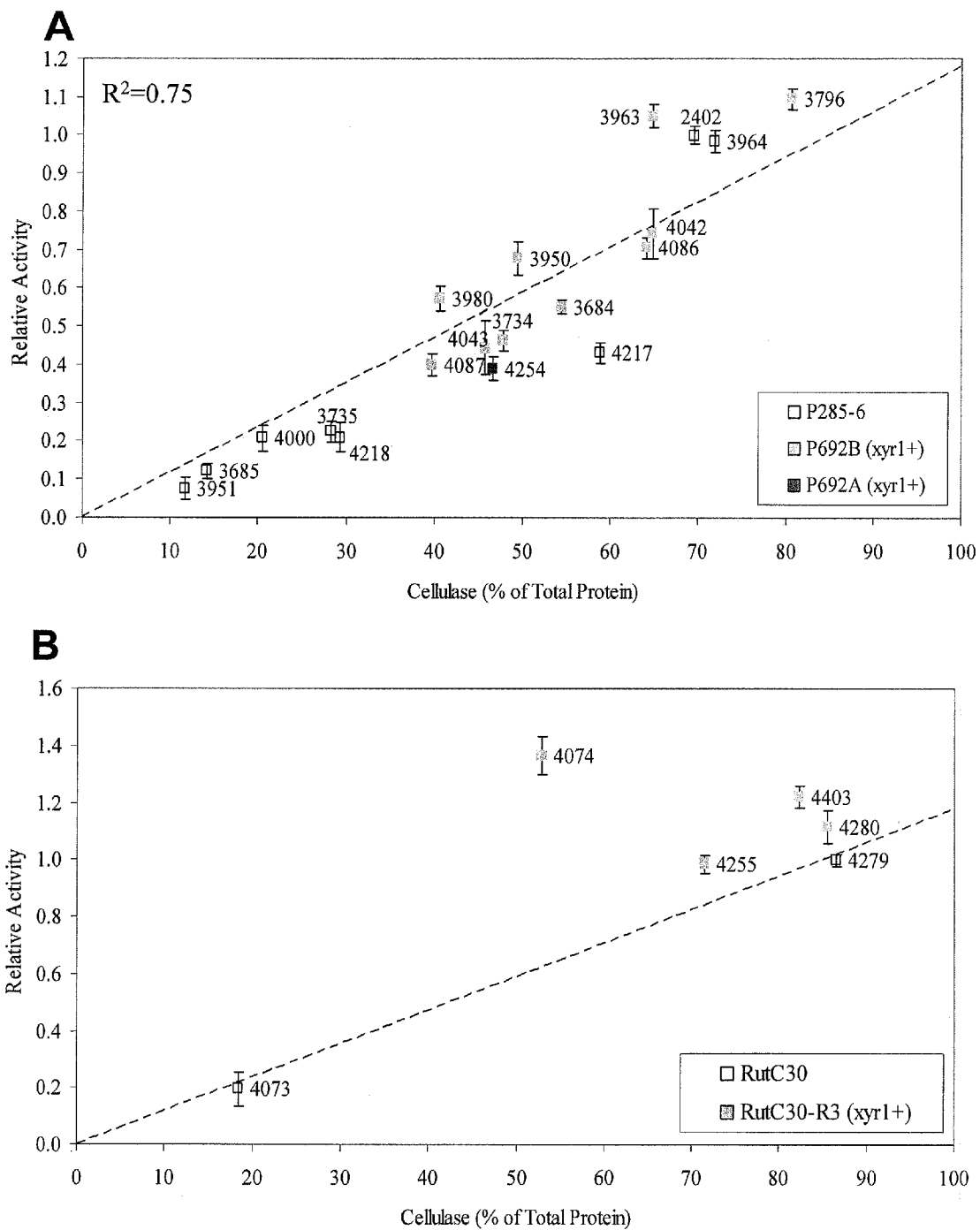
FIG. 12. (A) shows the correlation between the relative cellulose hydrolysis activity vs. the relative proportion of cellulase components (Cel7A+Cel6A+Cel7B) of the cellulase mixtures produced by P285-6, P692B (xyr1+) and P692A (xyr1+) in fermentations using 100% xylose, 100% arabinose, 25 wt % xylose/50 wt % glucose/25% glycerol or 25% xylitol/50% glucose/25% glycerol as the carbon source. The dotted line is a linear regression analysis of all relative activity vs. cellulase component percentage for P285-6, P692B, and P692A cellulase mixtures. The r-square value derived from the linear regression was 0.75. (B) shows the correlation between the relative cellulose hydrolysis activity and vs. the relative proportion of cellulase components (Cel7A+Cel6A+Cel7B+Cel5A) in cellulase mixtures produced from RutC30 and RutC30-R3 (xyr1+). The dotted line is a linear regression analysis of all relative activity vs. cellulase components percentage for RutC30 and RutC30-R3 cellulase mixtures.

[b] Ratio is based on results of ELISA determinations as described in Example 5.3. Ratio is the sum of the concentrations of the Cel7A, Cel7B, Cel6A and Cel5A cellulases to the sum of the concentration of the xyn1 and xyn2 xylanases, as shown in FIG. 12.

[c] Relative hydrolysis activity on a pretreated lignocellulosic substrate as described in Example 5.4.

Hydrolysis of Cellulosic Substrates

The cellulase mixture produced using the fermentation process of the present invention is useful for the hydrolysis of cellulase or a cellulosic substrate. By the term "cellulosic substrate", it is meant any substrate derived from plant biomass and comprising cellulose, including, but not limited to, pre-treated lignocellulosic feedstocks for the production of ethanol or other high value products, animal feeds, forestry waste products, such as pulp and wood chips, and textiles. The activity of the cellulase mixtures produced by the fermentation process of the present invention on pretreated lignocellulosic feedstock is presented in Table 3.

The cellulase enzyme produced by the fermentation process of the present invention may be used for the enzymatic hydrolysis of a "pretreated lignocellulosic feedstock". A pretreated lignocellulosic feedstock is a material of plant origin that, prior to pretreatment, contains at least 20% cellulose (dry wt), more preferably greater than about 30% cellulose, even more preferably greater than 40% cellulose, and at least 10% lignin (dry wt), more typically at least 12% (dry wt) and that has been subjected to physical and/or chemical processes to make the fiber more accessible and/or receptive to the actions of cellulolytic enzymes. Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, 4,600,590, Weil et al., 1997, Appl. Biochem. Biotechnol. 681: 21-40, and Öhgren, K., et al., 2005, Appl. Biochem. Biotechnol. Spring (121-124): 1055-1067; which are incorporated herein by reference).

For example, the cellulosic substrate may be incubated with the cellulase enzyme produced using the methods described herein, at a concentration of from about 1 to about 200 g cellulose per L of reaction mixture, or any amount there between, for example from about 1, 5, 10, 15, 20, 25, 30, 40, 50, 60, 70, 80, 90, 100, 120, 140, 160, 180, 200, or any amount therebetween, and with a cellulase dosage of from about 0.1 to about 100 mg protein per g cellulose, or any amount therebetween, for example from about 0.1, 0.5, 1.0, 2.0, 5.0, 10, 20, 30, 40, 50, 60, 70, 80, 90, 100 mg protein/g cellulose, or any amount therebetween. The reaction mixture may be incubated for from about 4 hours to about 120 hours, or any amount therebetween, at a temperature from about 30° to about 60° C., or any temperature therebetween, for example from about 30, 35, 40, 45, 50, 55, 60° C. or any temperature therebetween, and at a pH from about 3.5 to about 7.0, or any pH therebetween, for example a pH of about 3.5, 4.0, 4.5, 5.0, 5.5, 6.0, 6.5, 7.0 or any pH therebetween. Following incubation, the reaction products, including hemicellulose-derived carbohydrates, cellulase-inducing carbohydrates, glucose, and/or oligosaccharides can be used for further processing, for example as a substrate for producing ethanol, butanol, sugar alcohols, lactic acid, acetic acid, or the end products may be concentrated and purified using standard methods as known in the art.

In summary, the present invention provides highly productive fermentation processes that produce cellulase enzymes with low hemicellulase content useful for the hydrolysis of cellulosic substrates.

The above description is not intended to limit the claimed invention in any manner. Furthermore, the discussed combination of features might not be absolutely necessary for the inventive solution.

EXAMPLES

Example 1

Host Strains for Cloning and Expression of Xyr1 Transcription Factor

Example 1.1

Host *Trichoderma* Strains for the Overexpression of Xyr1 Transcription Factor

The host *Trichoderma reesei* strains used for the overexpression of xyr1 transcription factor are RutC30, P285-6aux and P491P6.

Strain RutC30 (ATCC #56765) was isolated as a high cellulase producing derivative of progenitor strain QM6A (Montenecourt and Eveleigh, 1979). Cellulase hyper-producing strains were generated from RutC30 by random mutation and/or selection. Strain M2C38 was isolated based on its ability to produce larger clearing zones than RutC30 on minimal media agar containing 1% acid swollen cellulose and 4 g $L^{-1}$ 2-deoxyglucose. Next, M2C38 was subjected to further random mutagenesis and strain BTR213 strain isolated by selection on lactose media containing 0.2 µg/mL carbendazim.

Strain P285-6aux is a derivative of strain BTR213 containing a deletion in the gene encoding endoglucanases 2 and also lacking the ability to grow on media lacking uridine. Deletion of the endoglucanases 2 gene was achieved by transformation of strain BTR213 with the p^EG2-hph-TV3 vector shown in FIG. 1. The coding region of the cel5a gene in p^EG2-hph-TV3 has been replaced by a hygromycin-resistance cassette in which the hygromycin phosphotransferase gene (hph) is operatively linked to the promoter of the *T. reesei* pgk gene and the transcriptional terminator of the *T. reesei* cellobiohydrolases 1 gene (as described in U.S. Pat. No. 6,015,703). The hygromycin-resistance cassette is flanked by approximately 2.8 kb and 2.4 kb of the endoglucanse 2 gene at the 5' and 3' ends, respectively, to enable homologous recombination within the endoglucanases 2 locus in the *T. reesei* genome. Strain BTR213 was transformed with p^EG2-hph-TV3, that had been linearized by digestion with XbaI restriction endonuclease, using PEG-mediated protoplast transformation method as described in Example 4. Transformants were selected on PDA media containing 20 U/mL of hygromycin. Deletion of the endoglucanase 2 (cel5a) gene in strain P285-6 was confirmed by PCR using primers specific for cel5a and hph genes as shown in FIG. 1B. A pyr4 auxotroph of strain P285-6 (strain P285-Eaux), deficient in uracil production, was isolated based on the ability to grow on minimal media agar supplemented with 5 mM uridine and 0.15% (w/v) of 5-fluoro-orotic acid.

Strain P491P6 is a derivative of strain M2C38 containing a deletion in the xylanase 2 gene and also lacking the ability to grow on media lacking uridine. Deletion of the xylanase 2 gene was achieved by transformation of strain M2C38aux5, a pyr4 auxotroph of M2C38 selected for the ability to grow on minimal media agar containing 5 mM uridine and 0.15% (w/v) 5-fluoro-orotic acid, with the pXBG2-pyr4-DR vector shown in FIG. 2. The coding region of the xylanase 2 gene in pXBG2-pyr4-DR has been replaced by a large insert comprising the *T. reesei* cel3a gene (encoding beta-glucosidase I) into which the *N. crassa* pyr4 gene flanked by Direct Repeats has been inserted. The direct repeat sequences were amplified by PCR using tetracycline gene as a template (671 bp-990 bp) and following primers: DR1-F GCGTGCTGCTAGCGC- TATATGC (SEQ ID NO: 28), DR1-R GGCCTGGTACCAT-ACCCACG (SEQ ID NO: 29), DR2-F GCGTGCTGGTAC-CGCTATATGC (SEQ ID NO: 30) and DR2-R GGCCTGCTAGCATACCCACG (SEQ ID NO: 31). The cel3A-pyr4 direct repeat cassette in pXBG2-pyr4-DR is flanked by approximately 2.1 kb and 1.9 kb of the xylanase 2 gene at the 5' and 3' ends, respectively, to enable homologous recombination within the xylanase 2 locus in the *T. reesei* genome. Strain M2C38aux5 was transformed with pXBG2-pyr4-DR that had been linearized with Cla 1 restriction enzyme using PEG-mediated protoplast transformation method as described in Example 4. Transformants were selected on minimal medium agar as described in Example 4. All stable transformants were screened for deletion of the xylanase 2 gene by PCR amplication from genomic DNA using primers complementary to the xylanase 2 coding (data not shown). To verify the inability to produce xylanase 2 protein, all transformants were grown in *Trichoderma* microculture media with xylose as described in Example 5.1. The total secreted protein (10 μg) was separated on 12% SDS-PAGE, transferred to PVDF membrane and immunoblotted using antibodies raised against xylanase 2. The absence of xyn2 specific band in the total secreted protein samples of some transformant strains confirmed successful deletion of xyn2 gene (FIG. 2B). A pyr4 auxotroph of strain P491P (strain P491P6) deficient in uracil production was isolated based on the ability to grow on minimal media agar supplemented with 5 mM uridine and 0.15% (w/v) of 5-fluoro-orotic acid Example 2

Enzyme Production and Expression Levels of Transcriptional Regulators, Xyr1 and Ace1, in *Trichoderma* Fermentations on Different Feeds

*T. reesei* strain P59G was used for the assessment of protein, biomass production, $q_p$, and the expression levels of cbh1 (cellobiohydrolase 1), xyr1 (xylanase regulator 1) and ace1 (activator of cellulase 1) grown in fed-batch fermentation on different carbon sources. Strain P59G is a genetically modified strain of strain BTR213 (described in Example 1) that produces and secretes high levels of the beta-glucosidase encoded by *T. reesei* bgl1 as described in U.S. Pat. No. 6,015,703.

Example 2.1

Fermentations on Pentose Sugars with CIC

*Trichoderma* spores from frozen (−80° C.) 15% glycerol stocks of strain P59G were inoculated onto standard 85 mm Petri plates containing potato dextrose agar (PDA). These plates were incubated at 28° C. for 3-5 days to achieve a confluent growth of fresh green spores. To prepare the inoculum for fermentation testing, spores from a single PDA plate were transferred to 2 L, baffled Erlenmeyer flask containing 750 mL of liquid Berkley media (pH 5.5) supplemented with 5.1 g/L of corn steep liquor powder and 10 g/L glucose. Flasks were incubated at 28° C. for 3 days using an orbital agitator (Model G-52 New Brunswick Scientific Co.) running at 100 rpm.

| Berkley Media for Flasks | |
|---|---|
| Component | g/L |
| $(NH_4)_2SO_4$ | 10.4 |
| $KH_2PO_4$ | 2.0 |
| $MgSO_4 \cdot 7H_2O$ | 0.31 |
| $CaCl_2 \cdot 2H_2O$ | 0.53 |
| Dry Corn Steep Liquor | 5.1 |
| Glucose | 10 |
| Trace elements* | 1 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The contents of an inoculum flask were transferred to a 14 L pilot scale fermentation vessel (Model MF114 New Brunswick Scientific Co.) set up with 10 L of Initial Pilot Media (pH 5.5). The vessel was run in batch mode until glucose in the media was depleted. At this point, the carbon source was added, on a continuous basis, from a stock that was 35.5% w/v of solids dissolved in water. Peristaltic pumps were used to deliver the carbon source at a feed at a rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis. The total fermentation time is typically between 96-144 hours.

| Initial Media for Fed-Batch Fermentations | |
|---|---|
| Component | g/L |
| $(NH_4)_2SO_4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.

The biomass content of the culture broth was determined using aliquots of 5-10 mL that had been weighed, vacuum filtered through glass microfiber filters, and oven dried at 100° C. for 4 to 24 hours. The concentration of biomass was determined according to the equation below.

Biomass(g/L)=dry filter paper and cake (g)−filter mass (g)×broth density (g/mL)×1000 (mL/L)/wet sample mass (g)

The protein concentration of culture filtrate was determined using the Bradford assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration. The specific productivity, $q_p$, was expressed as mg protein produced per gram of biomass per hour of fermentation.

*Trichoderma reesei* P59G strain fermentation profiles on various carbon sources are shown in FIG. 1. As expected, the amount of total protein produced during 164 hrs on a cellulase-inducing cocktail (CIC) is significantly higher than that produced in fermentations on either xylose or arabinose with 2% cellobiose. In contrast, the production of biomass was significantly higher on pentose sugars and resulted in low specific productivity over the course of fermentation (Table 4). The production of cellulase on hemicellulose derived carbohydrate (HDC) can be improved by additions of 8-15% of CIC to the feed (Table 4).

TABLE 4

Protein and biomass production by
*T. reesei* P59G on different feed type.

| Strain | Carbon source | Protein, g/L | Biomass, g/L | Average $q_p$, mg/g/L | Max $q_p$, mg/g/L |
|---|---|---|---|---|---|
| P59G | 65% Glucose/35% CIC[a] | 36.95 | 18.49 | 21.74 | 41.77 |
| P59G | 98% Xylose + 2% cellobiose[b] | 15.84 | 35.65 | 6.47 | 11.16 |
| P59G | 98% Arabinose + 2% cellbiose[b] | 10.71 | 32.94 | 4.44 | 11.01 |

[a]average from five fermentations
[b]average from two fermentations

Example 2.2

Expression Levels of Xyr1, Ace1 and Cel7a on Different Carbon Sources

Biomass samples were obtained from the above fermentations at the time point of 72 hrs after cellulase induction. The fermentation samples were filtered through GF/A microfiber paper, washed with sterile water and frozen in liquid nitrogen. Frozen mycelia was crushed by grinding in liquid nitrogen and total RNA was extracted using the procedure outlined in Strategene RNA Isolation Kit (VWR Cat. # CA99900-134). RNA was quantified using a conversion of $OD_{260\ nm}=1.0$ representing a concentration of 40 µg/mL. First strand cDNA was prepared using exactly 10 µg of total RNA from each transformant sample. RNA was mixed with 1.5 µL of 100 µM AncT primer (Invtrogen), 2 µL of 25 mM dNTP (each dNTP 6.25 mM) and made up to 25 µL with RNase and DNAse free water from GIBCO. The RNA mixture was heated at 65° C. for 5 minutes and then quick cooled in an ice bath for 2 minutes. To this mixture, 8 µL of 5× first strand Buffer (Invitrogen), 4 µL of 0.1M DTT (Invtrogen) and 1 µL of RNasein (Invitrogen) were added. The tubes were mixed and incubated at 42° C. for 2 minutes. Following this, 2 µL of SuperScriptII (Invitrogen) was added. The synthesis reaction was continued at 42° C. for 60 minutes for all samples. First strand cDNA was stored at −20° C.

The expression levels of genes encoding transcriptional regulators xyr1 and ace1 and their target cbh1 gene were determined by quantitative real-time PCR (qRT-PCR) using the Strategene MX3000P qRT-PCR system. All qRT-PCR reagents, except for the amplicon-specific primers, were purchased from Stratagene and used according to the manufacturer's instructions. Measurement of transcript levels was determined using the standard curve method. Standard curves were constructed for a constitutively expressed reference gene encoding nuclear transport factor 2 (Ntf-2) and for each of the xyr1, ace1 and cel7a amplicons using the primers indicated in Table 5 (SEQ ID 1 to 8). For generation of standard curves, equal aliquots of all collected cDNA samples were pooled, diluted 1:10, 1:100 and 1:1000 in sterile water and used for qRT-PCR as follows. To determine the relative transcript level of each gene cDNA, diluted samples were further diluted 1:20 and 2 µL aliquoted in triplicate into a 96-well qRT-PCR array micro-well plate. To each well, 18 µL of SYBR Green Master mix containing: 2×Brilliant SYBRGreen (10 µL), 1/500 dilution (0.75 µL) of ROX reference dye, 10 pmol containing equal amount of forward and reverse primers (1 µL) and 6.25 µL of GIBCO water were added. The PCR profile consisted of the following steps: I) 1 cycle of 15 min at 25° C., 10 min at 95° C.; II) 40 cycles of 30 sec at 95° C.; 20 sec at 55° C.; 20 sec at 72° C.; III) 1 cycle of 1 min at 95° C.; 30 sec at 55° C.; 30 sec at 95° C. Analysis of the data was performed as described in the Stratagene MX3000P manual for converting the fractional cycle at which exponential produced is reliably detected (Ct) to copy number. Standard curves were plotted for each gene to measure the copy number. These values were then normalized to the reference gene Ntf-2. The final value is the relative expression level of the target gene in relation to reference gene.

TABLE 5

List of primers used for qRT-PCR:

| SEQ ID | Primer name | Primer sequence |
|---|---|---|
| 1 | Ntf2F | ACAGAGTTGGCATTGTAGACAGCG |
| 2 | Ntf2R | CGAGTAAAGCACACAAACCGCCAA |
| 3 | Xyr1F | AGCCAGATTCTCGAGTTTGACCCT |
| 4 | Xyr1R | GCAAGCTTCGTGTGCCCTAACAAT |
| 5 | Ace1F | AGAAGGAAATGGACCGCCACATCA |
| 6 | Ace1R | AGTTCGACTCACGCTTCGACTTGT |
| 7 | Cel7aQ1F | TACTCTGGCAACGAAGCTCAACGAT |
| 8 | Cel7aQ1R | GCCACAGCATGTTGGCGTAGTAA |

Figure 3:
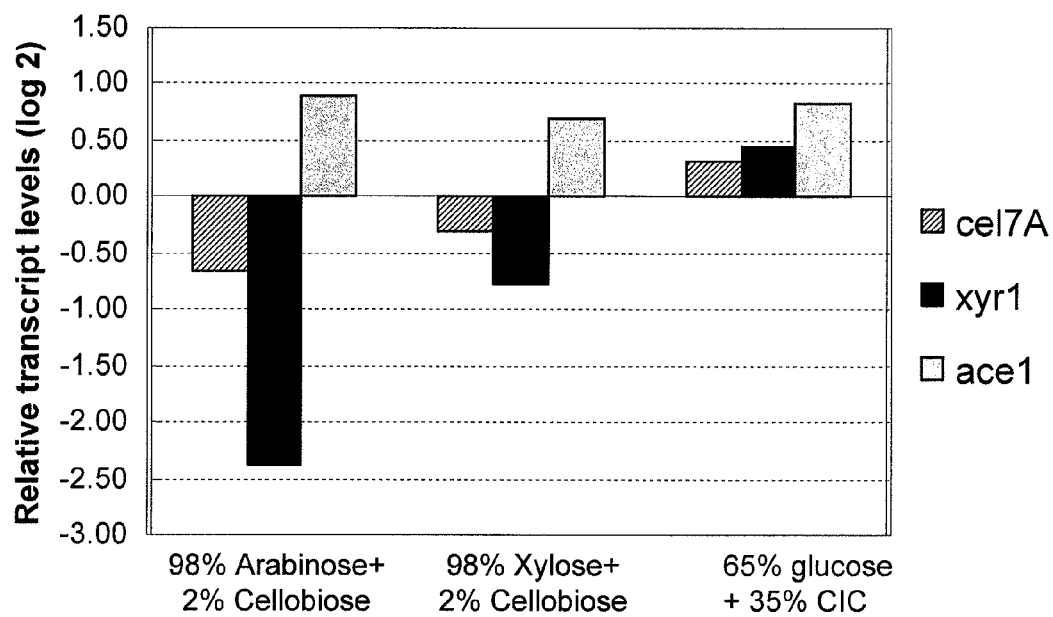
FIG. 3. Relative transcript levels of cel7a (stripped bars), xyr1 (black bars) and ace1 (grey bars) genes. The biomass samples for total RNA isolation were collected at 42 h of T. reesei strain P59G fermentation time when grown on 100% arabinose, 98% xylose+2% cellobiose, or 65% glucose+35% cellulase-inducing cocktail (CIC) as the carbon source. The relative transcript levels were assessed by real time qRT-PCR and normalized to the transcription levels of the Ntf2 gene.

The expression levels of cbh1 gene on 98% xylose+2% cellobiose or 98% arabinase+2% cellobiose are lower than that on 65% glucose+35% CIC (FIG. 3). This correlates with protein production profiles (Table 4) and the expression levels of transcriptional activator Xyr1 encoding gene (FIG. 3). In contrast, the transcript levels of the negative transcriptional regulator ace1 are independent of carbon source supplied to the fermentation (FIG. 3). Without wishing to be bound by theory, it is possible that the lower levels of positive transcriptional regulator Xyr1 is the rate limiting factor which results in lower cellulase and overall protein production on HDC.

Example 3

Cloning of *Trichoderma reesei* Xyr1 Gene

Example 3.1

*Trichoderma reesei* Genomic DNA Isolation and Amplification of Xyr1

For genomic DNA isolation, *T. reesei* spores collected from a Potato Dextrose Agar (PDA) plate were inoculated in 50 mL of Potato Dextrose Broth (PDB) (Difco). The cultures were shaken at 200 rpm for 2-3 days at 28° C. The mycelium was filtered onto a glass fiber circles (GFA) (Fisher Cat. #09-804-424) and washed with cold, deionized water. The fungal cakes were frozen in liquid nitrogen and crushed into a powder with a pre-chilled mortar and pestle; 0.5 g of powdered biomass was resuspended in 5 mL of buffer containing 100 mM Tris, 50 mM EDTA, pH 7.5 and 1% sodium dodecyl sulphate (SDS). The lysate was centrifuged (5000 g for 20 mM at 4° C.) to pellet cell debris. The supernatant was extracted with 1 volume of TE buffer (10 mM Tris, 1 mM EDTA, pH 8.0) saturated phenol followed by extraction with 1 volume of buffer-saturated phenol:chloroform:isoamyl alcohol (25:24:1). Genomic DNA was precipitated from the solution by adding 0.1 volumes of 3 M sodium acetate, pH 5.2 and 2.5 volumes of cold 95% ethanol. After incubating for at least 1 h at −20° C., the DNA was pelleted by centrifugation (5000 g for 20 mM at 4° C.), rinsed with 10 mL 70% ethanol, air-dried and resuspended in 1 mL of TE buffer. The RNA was digested by the addition of Ribonuclease A (Sigma-Aldrich) (final concentration of 0.1 mg/mL) and incubation at 37° C. for 1 hour. Ribonuclease was removed by extracting with 1 volume of buffer-saturated phenol and 1 volume of buffer-saturated phenol:chloroform:isoamyl alcohol (25:24:1). The DNA was precipitated with 0.1 volumes of 3 M sodium acetate, pH 5.2 and 2.5 volumes of cold 95% ethanol, pelleted by centrifugation, rinsed with 70% ethanol, air-dried and resuspended in 50 µL of TE buffer. The concentration of DNA was determined by measuring the absorbance of the solution at 260 nm (p. C1 in Sambrook et al., 1989).

A DNA fragment comprising the xyr1 coding sequence and native terminator (SEQ ID NO: 23) was amplified from *T. reesei* genomic DNA using Platinum® Taq DNA polymerase (Invitrogen) and following primers: forward —CH25 CATATGTTGTCCAATCCTCTCCG (SEQ ID NO: 9) and reverse —CH26 GCGGCCGCGGTACCTACAGCCAT-GCTCATCGTGC (SEQ ID NO: 10). Restriction sites for NdeI and KpnI-NotI were added at the 5' and 3' ends of the xyr1 coding sequence and native terminator fragment, respectively. The PCR was performed according to the enzyme manufacturer's protocol with a primer annealing temperature of 60° C. and 4 min extension time for 30 cycles. The PCR reaction products were then run on 1% agarose TAE gel and a 3.5 Kb amplicon was gel extracted using Wizard SV Gel and PCR Clean-up System (Promega).

Example 3.2

Construction of the Plasmids

The PCR product containing the xyr1 coding region (SEQ ID NO: 24) was ligated into the pGEM®-T Easy Vector (Promega) generating pGEM-xyr1-t. The inducible beta-xylosidase 1 promoter (Pbxl1, SEQ ID NO: 26) was amplified from *T. reesei* genomic DNA using Platinum® Taq DNA polymerase (Invitrogen) and the following primers: forward —CH27 5'-GGTACCCAATTGAGAGCTTGTCTGCCT-TGATTACCATCC-3' (SEQ ID NO:13) and reverse —CH25'-AAGCTTGCGGCCGCCATATGCGTCCG-GCTGTCCTTCAATGG-3' (SEQ ID NO:14). These primers also added KpnI and NdeI-NotI-HindIII restriction sites were introduced at the 5' and 3' ends, respectively, of the amplified promoter fragments. The PCR reaction was performed according to the enzyme manufacturer's recommendations with a primer annealing temperature of 51.5° C. and 2.5 min extension time for 30 cycles. The 1.5 kb Pbxl PCR product of was purified using the Wizard SV Gel and PCR clean-up System (Promega) and cloned into the pGEM®-T Easy Vector (Promega) resulting in the generation of vector pGEM-Pbxl1. After digestion of this vector with KpnI and HindIII restriction enzymes, the Pbxl1 promoter fragment was gel extracted using the Wizard SV Gel and PCR clean-up System (Promega) and cloned into the corresponding sites of pUC119 vector generating pUC119-Pbxl1 plasmid. The pGEM-xyr1-t plasmid was digested with NdeI and KpnI restriction enzymes, the xyr1 fragment was separated by agarose gel eletrophoresis and gel extracted using Wizard SV Gel and PCR Clean-up System (Promega). The fragment was cloned into corresponding sites of pUC119-Pbxl1 plasmid generating pUC119-Pbxl1-xyr1-t plasmid.

Figure 4:
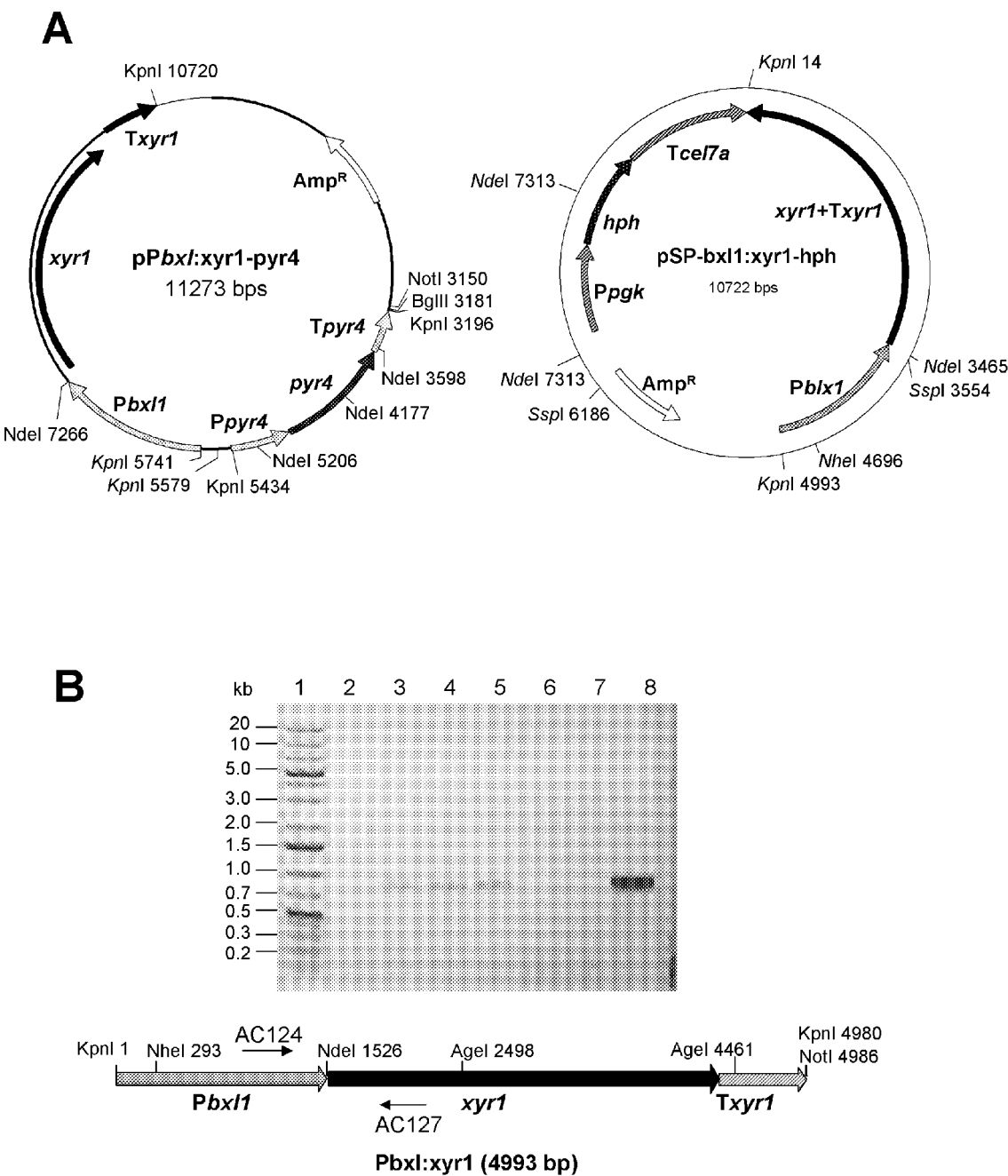
FIG. 4. A—Transformations vectors used to generate T. reesei transformants overexpressing xyr1. B—PCR amplification of chimeric xyr1 gene fragment from genomic DNA isolated from modified host filamentous fungal strains containing Pbxl:xyr1 expression cassettes and their parental filamentous fungal strains. Maps of the Xyr1 expression cassette are shown on the bottom of each panel. The primers used for PCR amplification (AC124 and AC127) are indicated by arrows. The DNA ladder was loaded in lane 1 and the size of each marker is indicated on the left. PCR products were amplified from the following templates: genomic DNA isolated from parental P285-6aux (lane 2) and modified host filamentous fungal strains P692A (lane 3), P692B (lane 4), 693A (lane 5), 693B (lane 6), water as a negative control (lane 7) and pPbxl:xyr1-pyr4 vector as a positive control (lane 8).

The selectable marker cassette conferring resistance to hygromycin was isolated from pHPT136 (described in U.S. Pat. No. 6,015,703) with XhoI and BglII restriction enzymes. The Ppgk-hph-Tcbh1 fragment was gel purified and ligated into XhoI and BamHI sites of pSP72 vector generating pSP-hph vector. The pUC119-Pbxl-xyr1-t was digested with the KpnI restriction enzyme and ~5.0 kb fragment containing xyr1 expression cassette was gel purified and ligated into KpnI site of pSP-hph vector to generate the pSP-bxl:xyr1-hph *T. reesei* transformation vector (FIG. 4A).

A pPbxl:xyr1-pyr4 *T. reesei* transformation vector was generated as follow. Plasmid pNcBgl-NSN(r)* (described in U.S. Pat. No. 7,456,005) containing the *Neurospora crassa* pyr4 gene was partially digested with KpnI restriction enzyme. The 6.2 kb linearized plasmid was electrophoretically separated in 1% agarose gel and purified using Wizard SV Gel and PCR Clean-up System (Promega). The Pbxl-xyr1-t fragment was isolated after complete digestion of pUC119-Pbxl-xyr1-t with KpnI restriction enzyme and gel purification as described above. The 5.0 kb xyr1 expression cassette was ligated into linearized pNclBgl-NSN(r)* generating final transformation vector pPbxl:xyr1-pyr4 (FIG. 4A).

Example 4

Generation of Modified Host Filamentous Fungus Overexpressing Xyr1 Transcription Factor The pPbxl-xyr1-pyr4 transformation vector was introduced into *T. reesei* strains P285-6aux and P491P6 and the pPS-bxl:xyr1-hph transformation vector was introduced into the RutC30 wild type strain using PEG-mediated protoplast transformation method. About 5×10$^6$ spores of selected strain spores were plated onto sterile cellophane placed on PDA supplemented with 5 mM uridine and incubated for 20 hours at 30° C. Cellophane discs with mycelia were transferred to 10 mL of a protoplast preparation solution containing 7.5 g/L Driselase and 4 g/L beta-glucanase (InterSpex Products Inc., Cat. #0465-1 and 0439-2, respectively) in 50 mM potassium phosphate buffer, pH 6.5 containing 0.6 M ammonium sulfate (Buffer P). The mycelia were digested for 5 hours at 28° C. with gentle agitation at 60 rpm. Protoplasts were collected by centrifugation at 1000-1500×g for 10 min at room temperature and washed with 5 mL of Buffer P. The pellet was resuspended in 1 mL of STC buffer (1.2 M sorbitol, 10 mM CaCl$_2$, 10 mM Tris-HCL, pH 7.5), separated from undigested mycelia by filtration through sterile No. 60 MIRACLOTH™ and collected into a sterile microcentrifuge tube. For transformation, 0.1 mL of protoplast suspension (approximately 5×10$^6$ protoplasts) was combined with 10 µg of linearized vector DNA, and 25 µL of PEG solution (25% PEG 4000, 50 mM CaCl$_2$, 10 mM Tris-HCl, pH 7.5). Protoplasts with DNA were incubated on ice for 30 min then 1 mL of PEG solution was added and the mixture incubated for 5 min at room temperature. Transformation mix was diluted with 2 mL of 1.2 M sorbitol in PEG solution.

Four 0.75 mL aliquots of the transformation mix with pPbxl-xyr1-pyr4 plasmid and protoplasts of strain P285-6aux or P491P6 were added into 25 mL of molten MMSS agar media (see below) cooled to about 47-50° C. and the protoplast suspensions were poured over MM agar (see below). Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA (Difco) and incubated at 30° C. for sporulation and subsequent genetic analysis.

Four 0.75 mL aliquots of the transformation mix with RutC30 protoplasts and pSP-bxl:xyr1-hph plasmid were added into 25 mL of PDA media cooled to about 47-50° C. and the protoplast suspensions were poured into 150 mm diameter Petri dishes. After 5 h incubation at 30° C., 25 mL of overlay media scontaining 80 U/mL of hygromycin was added. Plates were incubated at 30° C. until colony growth was visible. Transformants were transferred to individual plates containing PDA agar with 40 U/mL of hygromycin for secondary selection. Isolated stable transformants were transferred to PDA media and allowed to sporulate. Spores were collected and plated at high dilution on PDA with 40 U/mL of hygromycin to isolate homokaryon transformants, which were then plated onto PDA (Difco) and incubated at 30° C. for sporulation and subsequent genetic analysis.

| Minimal medium (MM) agar: | |
|---|---|
| Component* | Amount for 1 L of medium |
| $KH_2PO_4$ | 10 g |
| $(NH_4)_2SO_4$ | 6 g |
| $Na_3Citrate-2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |
| 20% Glucose f.s. | 50 ml |
| 1 M $MgSO4 \cdot 7H_2O$ f.s. | 4 mL |
| | pH to 5.5 |

*MMSS agar contains the same components as MM agar plus 1.2 M sorbitol, 4 mM $MgSO_4$, 1 g/L YNB (Yeast Nitrogen Base w/o Amino Acids from DIFCO Cat. No. 291940) and 0.12 g/L amino acids (-Ura DO Supplement from CLONTECH Cat. No. 8601-1).

Example 5

Genetic Characterization of Modified Host Filamentous Fungi

Example 5.1

Confirmation of Vector Integration into *T. reesei* Genome

The presence or absence of Pbxl:xyr1 expression cassette in isolated modified host filamentous fungi was assessed by PCR on isolated genomic DNA samples using specific primers as described below. For genomic DNA extraction mitotically stable transformants were sporulated on Potato Dextrose Agar. Spores were collected by overlaying the PDA plates with 1 mL of Potato Dextrose broth (PDB) medium and germinated by incubation at 30° C. for 24-36 h without shaking. Mycelia were centrifuged at 10,000 rpm in a microfuge and supernatant discarded. Pellets were resuspended in 0.25 mL of RNA lysing buffer (Stratagene RNA isolation kit Cat #400800) and equal volume of glass beads was added to each cell suspension. Microcentrifuge tubes were vortexed at maximum speed for 3 min to shear the mycelia. An equal volume of phenol:chloroform:isoamyl alcohol was added and the microcentrifuge tubes vortexed for 30 sec. Finally, 0.4 mL of TE buffer, pH 7.5 was added and the microcentrifuge tubes vortexed for 30 sec. The aqueous phase was separated by microcentrifugation at 13,000 rpm for 10 min and transferred to fresh tubes. The genomic DNA was precipitated by adding 1/10 volume of 3M sodium acetate (pH 5.2) and 2.5 volumes of 100% ethanol. DNA was pelleted by centrifugation at 13,000 rpm for 10 min. Pellers were washed with 70% ethanol. dried at room temperature and then dissolved in 30-40 µL of sterile water containing RNaseA (0.005 mg/mL). One microliter of genomic DNA was used in following PCR reactions.

PCR analysis of the genomic DNA isolated from putative modified host filamentous fungi was used to confirm the integration of the Pbx:xyr1 expression cassette. The PCR was performed using primers AC124 (Pbxl forward) TTGAGCG-CAGCATCACTGTGTAGA (SEQ ID NO: 17) and AC127 (xyr1 reverse), AACGGATCTGCGTCTGTGTCTGAT SEQ ID NO: 18 were used. GoTaq DNA polymerase (Promega) with an annealing temperature of 55° C. 1.5 min of extension time for 30 amplification cycles. Positive transformants were identified by amplification of a 1 kb PCR products containing Pbx:xyr1 expression cassettes from genomic DNA. No 1 kb PCR products were detected for parent strains P285-6aux (FIG. 4B), RutC30 and P491P6 (data not shown) indicating the absence of recombinant DNA Strains P692B, P692A, RutC30-R3, P1194E, P1194F, P1197B were identified as positive modified host filamentous fungi and selected for further analysis.

Example 5.2

Expression Levels of Xyr1 and (Hemi)Cellulase Genes

To determine transcription levels of xyr1 and selected (hemi)cellulase genes, the total RNA was isolated from mycelia of modified host filamentous fungi and parental strains grown in the Liquid Growth medium.

| Liquid growth medium: | |
|---|---|
| Component | Final concentration |
| Glucose | 10 g/L |
| Xylose | 10 g/L |
| Cellobiose | 2.5 g/L |
| Ammonium Sulphate | 6 g/L |
| 3xNa-Citratedihydrate | 3 g/L |
| $KH_2PO_4$ | 10 g/L |
| $MgSO_4 \cdot 7H_2O$ | 4 mM |
| $CaCl_2 \cdot 2H_2O$ | 2 mg/L |
| $ZnSO4 \cdot 7H_2O$ | 1.4 mg/L |
| $FeSO_4 \cdot 7H_2O$ | 5 mg/L |
| $MnSO_4 \cdot 7H_2O$ | 1.6 mg/L |

Culture tubes containing 5 mL of the Liquid Growth medium were inoculated with spores of modified host filamentous fungi and shaken at 30° C. for 4 days. The biomass was filtered through GF/A microfiber paper, washed with sterile water and frozen in liquid nitrogen. The isolation of RNA and qRT-PCR reactions were performed as described in Example 2.2. The primer pairs used for assessment of transcription levels of xyr1, cel7a, cel7b, xyn1, xyn2 and bxl1 genes are listed in Table 6.

TABLE 6

Primers used for qRT-PCR analysis of modified host filamentous fungi overexpressing Xyr1 transcription factor and parental filamentous fungi.

| SEQ ID NO | Primer name | Primer sequence |
|---|---|---|
| 1 | Ntf2F | ACAGAGTTGGCATTGTAGACAGCG |
| 2 | Ntf2R | CGAGTAAAGCACACAAACCGCCAA |
| 3 | Xyr1F | AGCCAGATTCTCGAGTTTGACCCT |
| 4 | Xyr1R | GCAAGCTTCGTGTGCCCTAACAAT |
| 7 | Cel7aQ1F | TACTCTGGCAACGAAGCTCAACGAT |
| 8 | Cel7aQ1R | GCCACAGCATGTTGGCGTAGTAA |
| 11 | Cel7bF | ATCACCCGCAAGTACCAGCAAA |
| 12 | Cel7bR | CTGGCTGTTGTCGTTCCAAATGCT |
| 15 | Xyn1F | TCATCAACTTCTCGGGCAGCTACA |
| 16 | Xyn1R | AGGTGCCAAAGTTCTCGACGATGT |
| 19 | Xyn2F | ACGGCTACTTCTACTCGTACTGGA |
| 20 | Xyn2R | TGTAGCTGCCCGAGAAGTTGATGA |
| 21 | Bxl1F | TATACGGCCATGCTGTTTGTTCGC |
| 22 | Bxl1R | TGGAAGAGTGACCAGGCTTGATGT |

Figure 5:
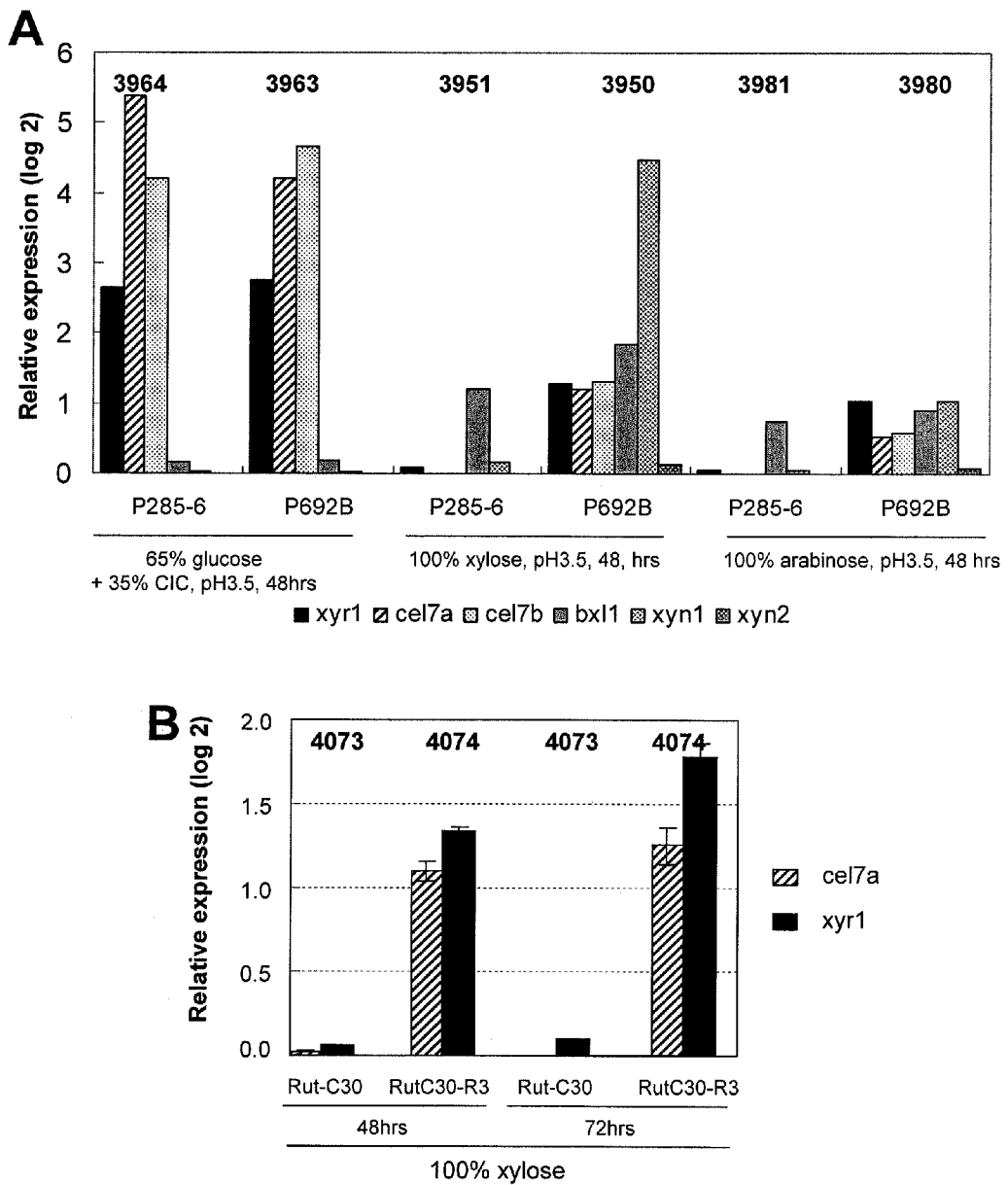
FIG. 5. A—The relative expression levels of xyr1, cel7a, cel7b, xyn1, xyn2, bxl1 genes in parental filamentous fungi (T. reesei P285-6) and modified host filamentous fungus overexpressing xyr1 (T. reesei strain P692) (.B—The relative expression levels of xyr1 and cel7a in parental filamentous fungi (T. reesei strain RutC30) and modified host filamentous fungi overexpressing xyr1 (T. reesei strain RutC30-R3) after 48 and 72 hrs from induction of cellulase expression. The biomass samples for total RNA isolation were prepared as described in Example 4.2. The relative transcription levels were assessed by real time qRT-PCR and normalized to the transcription levels of the Ntf2 gene. Fermentation run numbers are indicated on top of the bars.

All modified host filamentous fungi tested containing Pbxl: xyr1 expression cassette showed at least 2-fold increase in xyr1 transcript levels when grown on a carbon source comprising glucose, HDC (xylose) and CIC (cellobiose) relative to xyr1 transcript levels in the corresponding parental filamentous fungi grown with the same carbon source. For example, the modified host filamentous fungi, strains P692B and RutC30-R3, produced at least 2-fold higher levels of xyr1 transcript when grown on 100% xylose and 100% arabinose as compared to its parental filamentous fungi, strains P285-6 and RutC30 (FIGS. 5A and B). This resulted in significant increase in cel7a, cel7b and xyn1 transcript levels in the Xyr1 overexpression strains relative to those in the corresponding parental strain when the fermentation carbon source was 100% HDC (xylose or arabinose). The lowest effect of xyr1 overexpression was observed on the transcript levels of bxl1 and xyn1.

Example 6

Effect of Xyr1 Overexpression on Cellulase Production by Modified Host Filamentous Fungi Different types of carbon sources (e.g. glucose+CIC, 100% xylose, 100% arabinose and a blend of 50 wt % glycerol, 25 wt % glucose and 25 wt % xylitol) were used in 14 L fermentations. All fermentations and the assessment of the $q_p$, biomass and protein production were performed as described in Example 2.1. Highly productive *T. reesei* strains on glucose+CIC usually produce 30-45 g/L of total protein during 160-180 hrs in 14 L pilot scale fermentation. The maximum $q_p$ is reached at about 40-60 hrs of fermentation time and declines at the end of fermentation. Parental strains, P285-6, P491P and RutC30, showed usual fermentation performance indicators on glucose+CIC (Table 2) suggesting that the introduction of the additional copy of xyr1 gene under control of bxl1 promoter did not significantly affect cellulase gene expression under these. However, since the extra copy of xyr1 in P692B is expressed under the control of the bxl1 promoter, and the bxl1 gene is poorly expressed during fermentation on glucose+CIC as a feed, it is possible that the expression levels of xyr1 transcription factor did not increase significantly and, thus, it was not sufficient to increase cellulase production.

The maximum $q_p$ and the amount of total protein (in g/L) produced by the modified host filamentous fungi, strains P692B, P692A, RutC30-R3, P1197 B, P1194E and P1194F, during the fermentations on 100% xylose increased about 4- and 3-fold compared to those of the corresponding parental filamentous fungi, strains P285-6, RutC30 and P491P, respectively (Table 2). Moreover, the modified host filamentous fungi accumulated significantly less biomass in fermentations with 100% xylose as carbon source than their corresponding parental filamentous fungi (Table 2).

Figure 10:
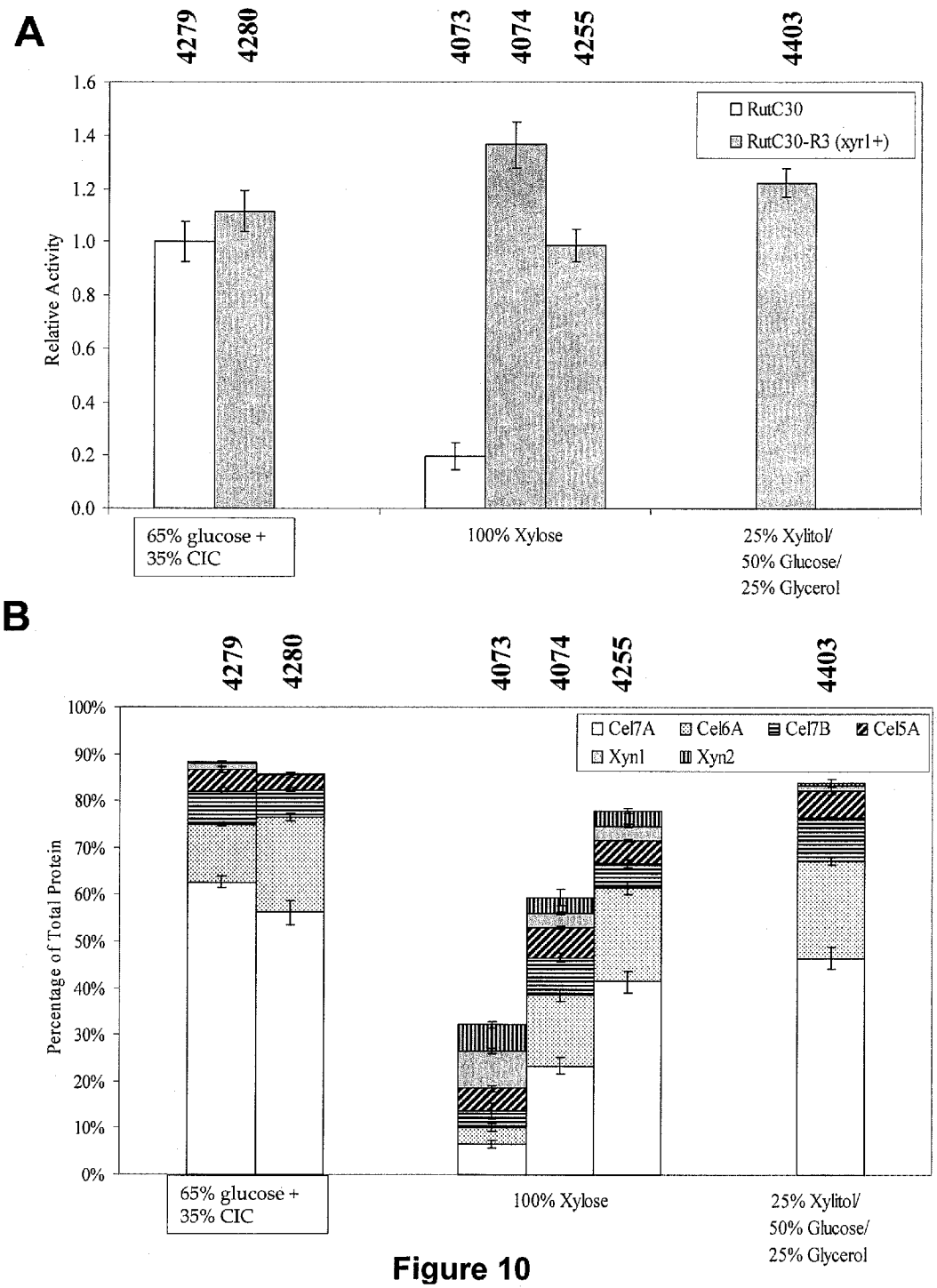
FIG. 10. (A) shows the relative cellulose hydrolysis activity of the cellulase mixtures secreted by parental filamentous fungal strain RutC30 and modified host filamentous fungal strains RutC30-R3 (xyr1+). Cellulase mixtures are grouped based on the carbon source used for the fermentation of each of these strains. Reference numbers for the fermentations are shown along the top of the graph. (B) shows the relative abundance (in wt % of total secreted protein) of individual cellulase and xylanase components Cel7A, Cel6A, Cel7B, Cel5A, Xyn1 and Xyn2 in the cellulase mixtures produced by parental (RutC30) and modified host (RutC30-R3) filamentous fungi grown on 100% xylose or 25% xylitol/50% glucose/25% glycerol.

Similar benefits of increased $q_p$ and protein yield were observed when the modified host filamentous fungi, strains P692A and RutC30-R3, were grown on other HDC (100% arabinose or a blend with 50 wt % glycerol/25 wt % glucose and 25 wt % xylitol) as carbon source over their respective parental filamentous fungus, strains P285-6 and RutC30 (Table 2). In some instances, as when arabinose was used as the carbon soured, the fermentation process with modified host filamentous fungus (strain P692A) produced more, not less, biomass than the process with the corresponding parental filamentous fungus (strain P285-6) in addition to achieving higher protein yields (FIG. 10). This manifests in a higher average $q_p$, indicating that the overexpression of xyr1 activates not only cellulase gene expression in arabinose-fed cultures, but also an overall more effective metabolism of arabinose.

Example 7

Analysis of Cellulase and Hemicellulase Components in Cellulase Mixtures Produced by Modified Host Filamentous Fungi Overexpressing Xyr1

Example 7.1

Determining the Relative Proportions of Cellulase and Hemicellulase Components Cellulase Mixtures Produced in 14 L Fed-Batch Fermentations The relative concentrations (in wt % of total secreted protein) of four cellulase components (Cel7A, Cel6A, Cel7B, Cel5A) and the two xylanase components, (Xyn1 and Xyn2) were determined by ELISA. Culture filtrates from 14 L fermentations and purified component standards were diluted to 0.01-10 μg/mL in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 hr at room temperature. Blocked microtitre wells were washed with PBS/Tween. Rabbit polyclonal antisera specific for Cel7A, Cel6A, Cel7B, Cel5A, Xyn1 and Xyn2 were diluted in PBS/BSA, added to separate microtitre plates and incubated for 2 hr at room temperature. Plates were washed and incubated with a goat anti-rabbit antibody coupled to horseradish peroxidase (Sigma #A6154), diluted 1/2000 in PBS/BSA, for 1 hr at room temperature. After washing, tetramethylbenzidine was added to each plate and incubated for 30 min at room temperature. The absorbance at 360 nm was measured in each well and converted into protein concentration using the Cel7A, Cel6A, Cel7B, Cel5A, Xyn1 and Xyn2 standard curves. The concentration of each component was expressed as the mass percent of the component as a fraction of total secreted protein. In one manner of analyzing these results, the concentrations of Cel7A, Cel6A, Cel7B and Cel5A were summed in each respective enzyme and collectively referred to as Cellulase in Table 3. Similarly, the concentrations of Xyn1 and Xyn2 were summed in each respective enzyme and collectively referred to as Xylanase in Table 3. The use of these terms does not imply that there are not other secreted proteins, which were not tested for here by ELISA, that could also be considered cellulase or xylanase.

Figure 9:
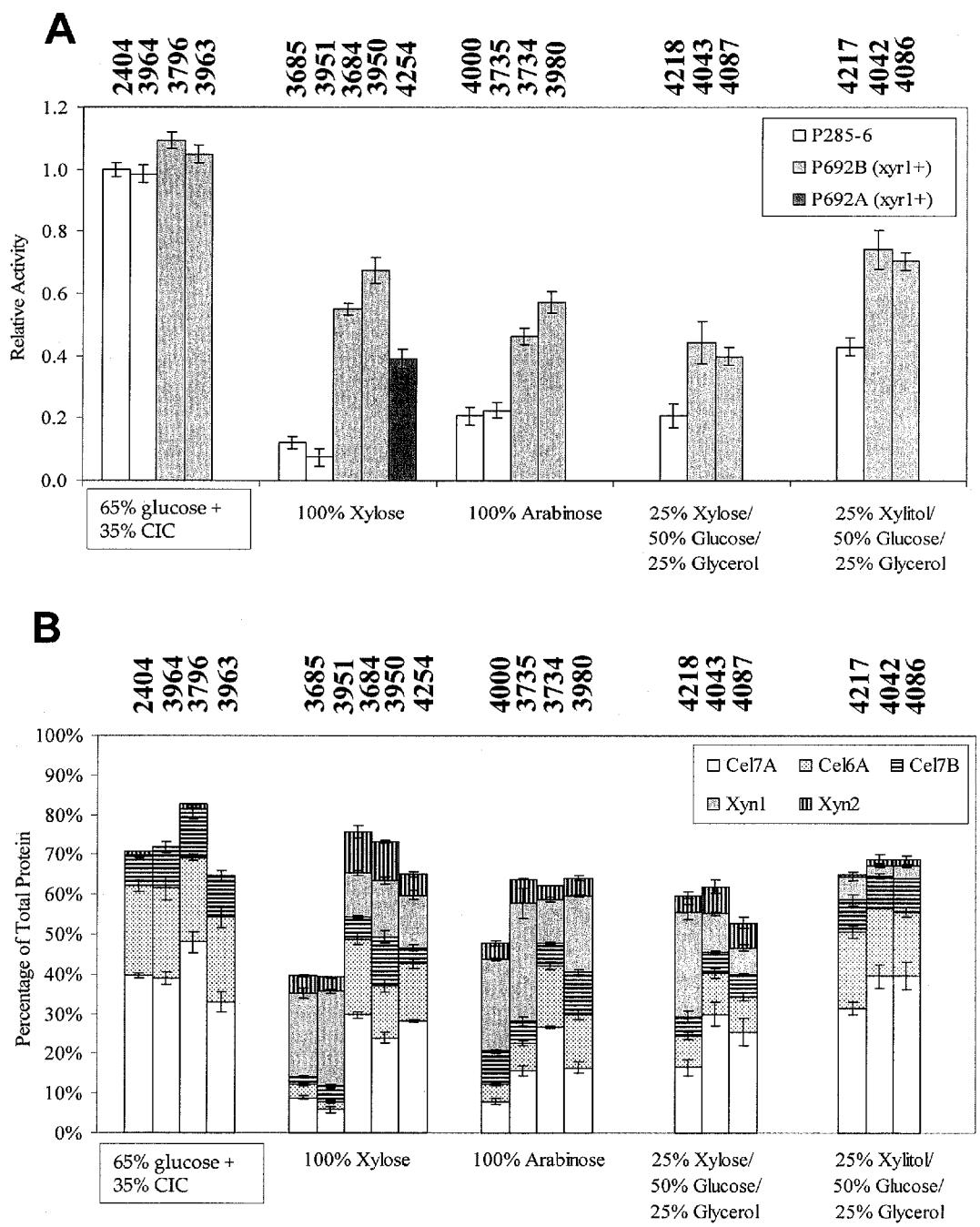
FIG. 9 (A) shows the relative cellulose hydrolysis activity of the cellulase mixtures secreted by parental filamentous fungal strain P285-6 and modified host filamentous fungal strains P692B (xyr1+) and P692A (xyr1+). Cellulase mixtures are grouped based on the carbon source used for the fermentation of each of these strains. Reference numbers for the fermentations are shown along the top of the graph. (B) shows the relative abundance (in wt % of total secreted protein) of individual cellulase and xylanase components Cel7A, Cel6A, Cel7B, Xyn1 and Xyn2 in the cellulase mixtures produced by parental (strain P285-6) and modified host (strains P692B and P692A) filamentous fungi grown on 100% xylose, 100% arabinose, 25% xylose/50% glucose/25% glycerol or 25% xylitol/50% glucose/25% glycerol.
Figure 11:
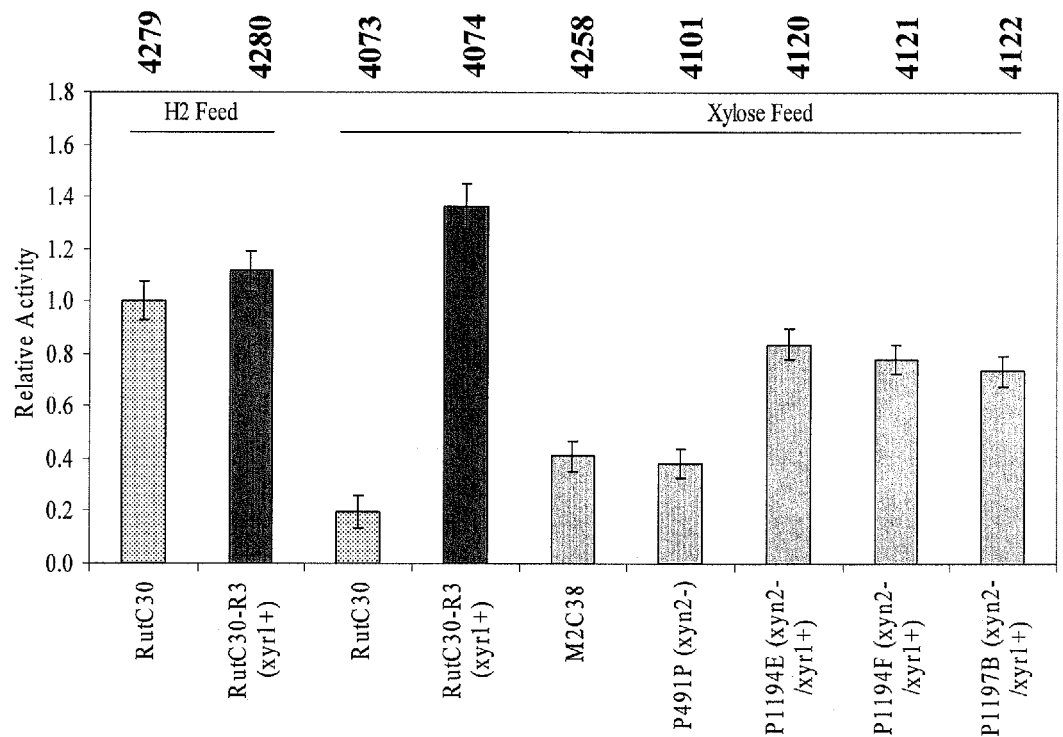
FIG. 11. shows the relative cellulose hydrolysis activity of the cellulase mixtures secreted by parental filamentous fungi strain RutC30, M2C38 and P491P and modified host filamentous fungal stains RutC30-R3, P1194E, P1194F and P1197B (xyr1) when grown on a carbon source comprising 100% xylose or 35% CIC+65% glucose. Reference numbers for the fermentations are shown along the top of the graph.

The ELISA results are presented in FIGS. 9B, 10B and 11B. These results show the relative proportion (in wt % of total secreted protein) of Cel7A, Cel6A, Cel7B, Cel5A, Xyn1 and Xyn2 in the cellulase mixture produced in fermentation processes using modified host or parental filamentous fungi with carbon source comprising HDC or CIC. The relative proportion of representative cellulase (Cel7A+Cel6A+Cel7B+Cel5A) and representative xylanase (Xyn1+Xyn2) in wt % of total secreted protein are shown in Table 3.

The relative proportion of cellulase components produced by the parental filamentous fungi, strains P285-6 and RutC30, during in a fermentation process where the carbon source comprised only HDC were 3- to 5-fold lower when compared to that produced in a fermentation process where the carbon source comprised glucose+CIC (FIGS. 9B and 10B and Table 3). In particular, the proportion of xylanase (Xyn1+Xyn2) increased from about 2 wt % of total secreted protein on glucose+CIC up to about 35 wt % on HDC (FIGS. 9B, 10B and Table 3).

The overexpression of xyr1 in the modified host filamentous fungi (strains P692B and RutC30-R3) resulted in 1.5- to 3-fold increase in the production of cellulase components (Cel7A, Cel6A, and Cel7B) in fermentations with 100% xylose or arabinose over the production of cellulase components by the corresponding parental filamentous fungis (strain P285-6 and RutC30) on the same carbon sources (FIGS. 9B and 10B and Table 3). Furthermore, the relative proportion of cellulase components in the cellulase mixture produced by modified host filamentous fungi that overexpress xyr1 (trains P692B and RutC30-R3) decreased less markedly, and the proportion of xylanase increased less markedly when the carbon source supplied to the fermentation process was 100% arabinose or xylose as compared to the cellulase mixture produced by the same strains in a fermentation process using glucose+CIC as the carbon source (FIGS. 9B and 10B and Table 3).

Fermentations on pure sugar and glycerol mix as a carbon source revealed that the production of hemicellulase significantly decreased when 50% glucose/25% glycerol/25% xylitol was used as a carbon source compared to that produced on 50% glucose/25% glycerol/25% xylose as a carbon source (Table 3, FIG. 9B).

Example 7.2

Beta-Xylosidase Content in Cellulase Mixtures Produced by Modified Host and Parental Filamentous Fungi The relative concentration of beta-xylosidase was calculated using Agilent Bioanalyzer 2100 using Protein Kit 230 as described in manufactures protocol. The beta-xylosidase, in wt % of total protein, produced in each fermentation is indicated in Table 3. As expected all parental filamentous fungi (strains P285-6, RutC30 and P491P) produced cellulase mixtures with a high relative proportion of beta-xylosidase in fermentation processes using HDC as a carbon source. Modified host filamentous fungi overexpressing xyr1 (strain P692B, RutC30-R3, P1194E, P1194F and P1197B) produced cellulase mixtures with up to 15-fold lower relative proportions of beta-xylosidase proportions in fermentation processed using the same HDC as carbon sources (Table 3). However, the relative proportion of Cel74A (xyloglucanase) in these cellulase mixtures (produced by the modified host filamentous fungi) increased up to 12 wt % of total protein while this protein was not detected in cellulase mixtures produced by the corresponding parental filamentous fungi grown on all types of carbon sources tested (data not shown).

Modified host filamentous fungi (strains P692B and RutC30-R3), when grown in fermentation processes in which the carbon source was 50 wt % glycerol/25 wt % glucose/25 wt % xylitol, produced cellulase mixtures with further reduced relative proportions of beta-xylosidase compared to fermentation processes in which the carbon source was 100% xylose or 50 wt % glycerol/25 wt % glucose/25 wt % xylose (Table 3).

Example 8

The Cellulose Hydrolysis Activity of Cellulase Mixtures Produced by Parental and Modified Host Filamentous Fungi The cellulose hydrolysis activity of cellulase mixtures produced by modified host filamentous funi overexpressing xyr1 and corresponding parental filamentous in fermentation processes using different carbon sources was assessed as described in U.S. patent application Ser. No. 11/846,653. The cellulase mixture produced from each fermentation process was tested in a 0.25 mL mixed cellulose hydrolysis assay. The cellulase mixtures were diluted in citrate buffer containing 0.5% sodium benzoate, complemented with a beta-glucosidase preparation from *Aspergillus niger* and incubated with acid pretreated wheat straw. The pretreatment was carried out as per Foody, U.S. Pat. No. 4,461,648. Incubation was at 50° C. for 24 hr and the target cellulose conversion level was greater than 70%. The activity of the cellulase mixtures was calculated by determining the amount of enzyme required to reach the target cellulose conversion level. The activity associated with cellulase mixtures produced by fermentations of parental modified host filamentous fungi (strains P285-6, P692A and P692B) were normalized to the cellulose hydrolysis activity of cellulase mixtures produced by the parental filamentous fungi (strain P285-6) using glucose+CIC as carbon source (fermentation number 2404). Similarly, the activity associated with cellulase mixtures produced by fermentations of parental and modified host filamentous fungi (strains RutC30, RutC30-R3, M2C38, P491P, P1194E, P1194F and P1197B) were normalized to the cellulose hydrolysis activity of cellulase mixtures produced by the parental filamentous fungi (strain RutC30) using glucose+CIC as carbon source (ferrmentation number 4279). These results are referred to as 'Relative Activity' in FIGS. 9A, 11A and 12A and in Table 3.

A small increase in activity of the cellulase mixture produced by P692B (fermentation numbers 3796 and 3963) was observed, relative to the activity of the P285-6 cellulase mixture, when glucose+CIC was used as the carbon source for fermentation (FIG. 9a and Table 3). This likely reflects a slight improvement in cellulase composition in respect of total secreted protein as discussed in Example 7.1.

As a result of the significantly increased proportion of cellulase components in the cellulase mixture protein produced by strain P692B in fermentation processes using 100% xylose or arabinose, the cellulose hydrolysis activity increased by 4- and 2-fold respectively compared to that of cellulase mixture produced by the parental strain P285-6 in a similar fermentation process (FIG. 9A and Table 3).

Similarly, the improved cellulase composition produced by strain P692B in a fermentation process in which the carbon source comprised xylitol rather than xylose correlates with up to 2-fold increase in cellulose hydrolyzing activity of the cellulase mixture produced by this modified host filamentous fungus as compared to that of the cellulase mixture produced by the parental filamentous fungus (strain P285-6) in similar fermentation processes. (Table 3 and FIG. 9A).

The deletion of xylanase 2 in P491P strain did not change the relative proportion of cellulase components in the cellulase mixtures compared to that in the cellulase mixtures produced by the its parent strain M2-C38. This is likely due to the low fermentation pH at which mainly xylanase 1 is expressed. However, as observed with P692B and RutC30-C3 modified host filamentous fungi, the overexpression of Xyr1 possibly results in loss of pH dependent expression and both xylanases are produced in similar abundance. Further, the deletion of xyn2 in the presence of Xyr1 overexpression resulted in about 3-fold increase in the proportion of cellulase components in the cellulase mixture and thus, improved cellulase activity (Table 3).

Further, the absence of significant difference in the proportion of cellulase components in the cellulase mixtures produced by strains M2-C38 and P491P strains was reflected in similar cellulase hydrolytic activity. The overexpression of Xyr1 in the presence of xyn2 deletion increased cellulase activity by about 2-fold in the cellulase mixtures produced by the modified host filamentous fungal strains P1194E, P1194F and P1197B transformants compared to that of the cellulase mixtures produced by parental strains M2-C38 and P491P.

REFERENCES

Aro, N, Ilmen, M, Saloheimo, A, Penttila, M (2003) Appl. Environ. Microbiol. 69: 56-65.

Aro, N, Pakula, T, Penttila, M (2005) FEMS Microbiol. Reviews, 29:719-739.

Bailey, M J, Buchert, J, Viikari, L, (1993) Appl. Microbiol. Biotechnol, 40: 224-229.

Brunner, K, Lichtenauer, A M, Kratochwill, K, Delic, M, Mach, R L, (2007) Curr Genet. 52:213-220.

Calero-Nieto, F, Di Pietro, A, Roncero, M I, Hera, C, (2007) Molecular Plant-Microbe Interactions. 20:977-985.

Coutinho, P. M. & Henrissat, B., 1999, "Carbohydrate-active enzymes: an integrated database approach." In *Recent Advances in Carbohydrate Bioengineering*, H. J. Gilbert, G. Davies, B. Henrissat and B. Svensson eds., The Royal Society of Chemistry, Cambridge, pp. 3-12

De Vries, R P, and Visser, J (2001) Mocrobiol. Mol. Biol. Reviews, 65(4): 497-522.

Furukawa, T, Shida, Y, Kitagami, N, Mori, K, Kato, M, Kobayashi, T, Okada, H, Ogasawara, W, Morikawa Y (2009) Fungal Genet Biol 46 (8): 564-574

Hasper, A A, Trindale, L M, van der Veen, D, van Ooyen, A J, de Graaff, L H (2004) Microbiology 150: 1367-1375.

Hasper, A A, Visser, J, de Graaff, L H (2000) Mol. Microbiol. 36: 193-200.

Ilmen, M, Saloheimo, A, Onnela, M-L, Penttila, M (1997) Appl. Environ. Microbiol. 63: 1298-1306.

Lai, E, Teodoro, T, Volchuk, A, (2007) Physiology 22:193-201.

Ling, M, Qin, Y, Li, N, Liang, Z (2009) Biotechnol Letters 31: 227-231

Mach, R L and Zeilinger, S (2003) Appl. Microbiol. Biotechnol. 60: 515-522.

MacPherson, S, Larochelle, M, Turcotte, B (2006) Microbiol. Mol. Biol. Reviews 70: 583-604.

Margeot, A., et al., 2007, poster presentation at Physiology of Yeast and Filamentous Fungi, Espoo, Finland.

Margolles-Clark, E, Ihnen, M, Penttila, M (1997) J. Biotechnol. 57: 167-179.

Martinez, D. et al. (2008) Nature Biotech. 26: 553-560.

Marui, J, Kitamoto, N, Kato, M, Kabayashi, T, Tsukagoshi, N, (2002) FEBS Letters. 528:279-282.

Nagendran, S, Hallen-Adams, H E, Paper, J M, Aslam, N, Walton, J D, (2009) Fungal Genet. Biol. 46:427-435.

Pakula, T M, Laxell, M, Huuskonen, A, Uusitalo J, Saloheimo, M, Penttila, M, (2003) J. Biol. Chem. 278:45011-45020.

Phalip, V, Delalande, F, Carapito, C, Goubet, F, Hatsch, D, Leize-Wagner, E, Dupree, P, Dorsselaer, A V, Jeltsch, J M, (2005) Curr. Genet. 48:366-379.

Rao, U, Marui, J, Kato, M, Kobayashi, T, Tsukagoshi, N, (2002) Biotechnol. Letters. 24:1089-1096.

Rauscher, R, Wurleitner, E, Wacenovsky C, Aro, N, Stricker, A R, Zeilinger, S, Kubicek, C P, Penttila, M, Mach, R L (2006) Ekaryotic Cell 5:447-456.

Saha, B. C. (2003) Hemicellulose Bioconversion. *Journal of Industrial Microbiology and Biotechnology*. 30: 279-291

Strauss, J, Mach, R L, Zeilinger, S, Harder, G, Stoffler, G, Wolschek, M, Kubicek, C P, (1995) FEBS Letters 376: 103-107.

Stricker, A R, Grosstessner-Hain, K, Wurleitner, E, Mach R L (2006) Eukaryotic Cell 5: 2128-2137.

Stricker, A R, Trefflinger, P, Aro, N, Penttila, M, Mach, R L, (2007) Fungal Genet. Biol. 45:436-445.

Stricker, A R, Mach, R L, deGraaff, L H (2008) Appl Microbiol Biotechnol 78: 211-220

Tamayo, E N, Villanueva, A, Hasper, A A, de Graaff, L H, Ramon, D, Orejas, M, (2008) Fungal Genet. Biol. 45:984-993.

Xiong, H, Turunen, O, Pastinen, O, Leisola, M, von Weymarn, N (2004) Appl. Microbiol. Biotech. 64: 353-358.

Zeilinger, S., Mach, R. L., Schindler, M., Herzog, P., and Kubicek, C. P., (1996) J. Biol. Chem. 271: 25624-25629;

Zhang, K, and Kaufman, R J, (2004) J. Biol. Chem. 279: 25935-25938.

The invention claimed is:

1. A fed-batch or continuous fermentation process for the production of a cellulase mixture, said process comprising:
   a) providing a modified host filamentous fungus that overexpresses a Xyr1 transcription factor, said Xyr1 transcription factor being a protein (i) having an amino acid sequence exhibiting from about 90% to about 100% identity to SEQ ID NO: 27 (ii) containing a class III zinc binuclear cluster with a conserved amino acid motif $(CX_2CX_6CX_{5-12}CX_2CX_{6-8}C)$ at the N-terminal part of the protein, and (iii) exhibiting DNA binding activity specific to a consensus sequence $GGC(T/A)_3$-like motif within cellulase and/or hemicellulase promoter sequences; and
   b) culturing the modified host filamentous fungus of step a) in a medium comprising a carbon source, wherein the carbon source contains from about 60 wt % to about 100 wt % of a hemicellulose-derived carbohydrate selected from the group consisting of xylo-oligosaccharides, arabinoxylo-oligosaccharides, D-xylose, xylobiose, L-arabinose, and combinations thereof, and about 0 wt % of a cellulase-inducing carbohydrate selected from the group consisting of cellulose, lactose, cellobiose, sophorose, gentiobiose and a combination thereof, to produce a cellulase mixture;
   wherein the fermentation process produces at least 10 g/L of the cellulase mixture, cellulase components represent at least 40 wt % of the total protein in the cellulase mixture, and the cellulase mixture exhibits at least 1.7-fold higher cellulase activity than a cellulase mixture produced by a parental filamentous fungus that does not overexpress the Xyr1 transcription factor when cultured in the same medium.

2. The fermentation process of claim 1, wherein the Xyr1 protein comprises the amino acid sequence of SEQ ID NO:27.

3. The fermentation process of claim 1, wherein the modified host filamentous fungus is partially or completely deficient in expressing one or more hemicellulase enzyme.

4. The fermentation process of claim 3, wherein the one or more hemicellulase enzyme is selected from the group consisting of a xylanase, a beta-xylosidase, an alpha-arabinofuranosidase, a beta-mannanase, an alpha-glucuronidase, a acetyl xylan esterase and a combination thereof.

5. The fermentation process of claim 4, wherein the one or more hemicellulase enzyme is selected from the group consisting of a xylanase, a beta-xylosidase and a combination thereof.

6. A fermentation process for the production of a cellulase mixture, said process comprising:
   a) genetically modifying a host filamentous fungus to overexpress a Xyr1 transcription factor, said Xyl transcription factor being a protein (i) having an amino acid sequence exhibiting from about 90% to about 100% identity to SEQ ID NO: 27 (ii) containing a class III zinc binuclear cluster with a conserved amino acid motif $(CX_2CX_6CX_{5-12}CX_2CX_{6-8}C)$ at the N-terminal part of the protein, and (iii) exhibiting DNA binding activity specific to a consensus sequence $GGC(T/A)_3$-like motif within cellulase and/or hemicellulase promoter sequences; and
   b) culturing the host filamentous fungus of step a) in a medium comprising a carbon source, wherein the carbon source contains from about 60 wt % to about 100 wt % of a hemicellulose-derived carbohydrate selected from the group consisting of xylo-oligosaccharides, arabinoxylo-oligosaccharides, D-xylose, xylobiose, L-arabinose, and combinations thereof, and about 0 wt % of a cellulase-inducing carbohydrate selected from the group consisting of cellulose, lactose, cellobiose, sophorose, gentiobiose and a combination thereof, to produce a cellulase mixture;
   wherein the fermentation process produces at least 10 g/L of the cellulase mixture, and wherein cellulase components represent at least 40 wt % of the total protein in the cellulase mixture and the cellulase mixture exhibits at least 1.7-fold higher cellulase activity than a cellulase mixture produced by a parental filamentous fungus that does not overexpress the Xyr1 transcription factor when cultured in the same medium.

7. The fermentation process of claim 6, wherein the step of genetically modifying comprises
   a) transforming the host filamentous fungus with a Xyr1 genetic construct in which a nucleic acid sequence encoding the Xyr1 transcription factor is operatively linked to a promoter nucleic acid sequence; and
   b) selecting those transformants from step a) containing the Xyr1 genetic construct.

8. The fermentation process of claim 6, wherein the Xyr1 protein comprises the amino acid sequence of SEQ ID NO:27.

9. The fermentation process of claim 7, wherein the promoter nucleic acid sequence is native or heterologous to the host filamentous fungus.

10. The fermentation process of claim 7, wherein the promoter nucleic acid sequence is derived from a gene whose expression is induced during growth of the host filamentous fungus on a carbon source comprising hemicellulose derived carbohydrates.

11. The fermentation process of claim 10, wherein the promoter nucleic acid sequence is derived from a gene selected from the group consisting of *T. reesei* bxl1, *T. reesei* xln1 and *T. reesei* xln2.

12. The fermentation process of claim 7, wherein the promoter nucleic acid sequence is from a gene whose expression is constitutive during growth of the host filamentous fungus.

13. The fermentation process of claim 6, wherein the step of genetically modifying further comprises modifying one or more gene in said host filamentous fungus encoding a hemicellulase enzyme selected from the group consisting of xylanases, beta-xylosidases, alpha-arabinofuranosidases, beta-mannanases, alpha-glucuronidases, acetylxylan esterase and a combination thereof, so that said host filamentous fungus is partially or completely deficient in expressing the one or more hemicellulase enzyme.

14. The fermentation process of claim 13, wherein said one or more hemicellulase enzyme is selected from the group consisting of a xylanase and a beta-xylosidase.

15. The fermentation process of claim 1, wherein the process is characterized by having at least about a 2-fold increase in specific productivity ($q_p$) relative to an equivalent process utilizing a parental filamentous fungus that does not overexpress Xyr1.

16. The fermentation process of claim 6, wherein the process is characterized by having at least about a 2-fold increase in specific productivity ($q_p$) relative to an equivalent process utilizing a parental filamentous fungus that does not overexpress Xyr1.

17. The fermentation process of claim 1, wherein the host filamentous fungus is a species of *Trichoderma, Hypocrea, Aspergillus, Humicola, Fusarium, Penicillium, Neurospora, Phanerochaete, Agaricus, Chaetomium*, or *Magnaporthe*.

18. The fermentation process of claim 17, wherein the host filamentous fungus is *Trichoderma reesei* or *Hypocrea jecorina*.

19. The fermentation process of claim 6, wherein the host filamentous fungus is a species of *Trichoderma, Hypocrea, Aspergillus, Humicola, Fusarium, Penicillium, Neurospora, Phanerochaete, Agaricus, Chaetomium,* or *Magnaporthe*.

20. The fermentation process of claim 19, wherein the host filamentous fungus is *Trichoderma reesei* or *Hypocrea jecorina*.

21. The fermentation process of claim 1, wherein the medium comprises one or more additional carbon sources.

22. The fermentation process of claim 21, wherein the one or more additional carbon source is glycerol, one or more sugar alcohols or an organic acid.

23. The fermentation process of claim 22, wherein the one or more additional carbon source comprises xylitol.

24. The fermentation process of claim 6, wherein the medium comprises one or more additional carbon sources.

25. The fermentation process of claim 24, wherein the one or more additional carbon source is glycerol, one or more sugar alcohols or an organic acid.

26. The fermentation process of claim 25, wherein the one or more additional carbon source comprises xylitol.

27. The fermentation process of claim 1, wherein the step of culturing is conducted at a temperature of from about 20° C. to about 35° C. and a pH of from about 3.0 to about 6.5.

28. The fermentation process of claim 6, wherein the step of culturing is conducted at a temperature of from about 20° C. to about 35° C. and a pH of from about 3.0 to about 6.5.

29. The fermentation process of claim 1, wherein the process is fed-batch.

30. The fermentation process of claim 6, wherein the process is fed-batch.

31. The fermentation process of claim 1, wherein the process is continuous.

32. The fermentation process of claim 6, wherein the process is continuous.

33. The fermentation process of claim 1, wherein the process is conducted aerobically.

34. The fermentation process of claim 6, wherein the process is conducted aerobically.

35. The fermentation process of claim 1, wherein the carbon source contains 0 wt % cellulase-inducing carbohydrate.

36. The fermentation process of claim 6, wherein the carbon source contains 0 wt % cellulase-inducing carbohydrate.

37. A process for the hydrolyzing a cellulose substrate comprising contacting said substrate with a cellulase mixture produced by the fermentation process of claim 1.

38. The process of claim 37, wherein the cellulose substrate is a pretreated lignocellulosic feedstock.

39. A process for the hydrolyzing a cellulose substrate comprising contacting said substrate with a cellulase mixture produced by the fermentation process of claim 6.

40. The process of claim 39, wherein the cellulose substrate is a pretreated lignocellulosic feedstock.

41. A fermentation process for the production of a cellulase mixture, said process comprising:
  a. providing a modified host filamentous fungus that overexpresses a Xyr1 transcription factor, said Xyr1 transcription factor being a protein (i) having an amino acid sequence exhibiting from about 90% to about 100% identity to SEQ ID NO: 27, (ii) containing a class III zinc binuclear cluster with a conserved amino acid motif $(CX_2CX_6CX_{5-12}CX_2CX_{6-8}C)$ at the N-terminal part of the protein, and (iii) exhibiting DNA binding activity specific to a consensus sequence $GGC(T/A)_3$-like motif within cellulase and/or hemicellulase promoter sequences; and
  b. culturing the modified host filamentous fungus of step a) in a medium comprising a carbon source, wherein the carbon source contains from about 25 wt % to about 100 wt % of a hemicellulose-derived sugar alcohol, about 0 wt % of a cellulase-inducing carbohydrate and from about 0 wt % to about 75 wt % glucose, glycerol or a combination thereof, to produce a cellulase mixture;
  wherein the fermentation process produces at least 10 g/L of the cellulase mixture, cellulase components represent at least 40 wt % of the total protein in the cellulase mixture, and the cellulase mixture exhibits at least 1.7-fold higher cellulase activity than a cellulase mixture produced by a parental filamentous fungus that does not overexpress the Xyr1 transcription factor when cultured in the same medium.

42. The fermentation process of claim 41, wherein the hemicellulose-derived sugar alcohol is xylitol.

43. The fermentation process of claim 42, wherein the carbon source contains from about 0 wt % to about 25 wt % glycerol and from about 0 wt % to about 50 wt % glucose.

44. The fermentation process of claim 1, wherein said Xyr1 transcription factor has an amino acid sequence exhibiting from about 95% to about 100% identity to SEQ ID NO:27.

45. The fermentation process of claim 6, wherein said Xyr1 transcription factor has an amino acid sequence exhibiting from about 95% to about 100% identity to SEQ ID NO:27.

46. The fermentation process of claim 41, wherein said Xyr1 transcription factor has an amino acid sequence exhibiting from about 95% to about 100% identity to SEQ ID NO:27.

* * * * *

UNITED STATES PATENT AND TRADEMARK OFFICE
CERTIFICATE OF CORRECTION

PATENT NO. : 8,323,931 B2
APPLICATION NO. : 12/611486
DATED : December 4, 2012
INVENTOR(S) : Loreta Gudynaite-Savitch et al.

It is certified that error appears in the above-identified patent and that said Letters Patent is hereby corrected as shown below:

ON TITLE PAGE (56) OTHER PUBLICATIONS

Under Ahmed et al., "Trichoderma harzianum" should read --*Trichoderma harzianum*--;
Under Brunner et al., "Fusarium graminearum"," should read
    --*Fusarium graminearum*",--;
Under Calero-Nieto et al., "Fusarium oxysporum" should read --*Fusarium oxysporum*--;
Under Furukawa et al., "Trichoderma reesei"," should read --*Trichoderma reesei*",--;
Under Ilmen et al., "Trichoderma reesei"," should read --*Trichoderma reesei*",--;
"Margolles-Clark et al.," should read --¶ Margolles-Clark et al.,--.

ON TITLE PAGE (57) ABSTRACT

Line 3, "a" should read --an--.

ON TITLE PAGE 2 (56) OTHER PUBLICATIONS

Under Rauscher et al., "Hypocrea jecorina"," should read --*Hypocrea jecorina*",--;
Under Stricker et al., "Xyrl, "Hypocrea jecorina"," should read
    --*Hypocrea jecorina*",--; and
Under Stricker et al., "Role of Ace2, "Hypocrea jecorina"," should read
    --*Hypocrea jecorina*",--.

In the Specifications:

COLUMN 1

Line 53, "2009)" should read --2009).--.

Signed and Sealed this
Twenty-first Day of May, 2013

Teresa Stanek Rea
*Acting Director of the United States Patent and Trademark Office*

COLUMN 2

Line 37, "examples," should read --example,--;
Line 43, "knock out" should read --knockout--; and
Line 65, "et al," should read --et al.,--.

COLUMN 3

Line 1, "et al," should read --et al.,--;
Line 4, "et al," should read --et al.,--;
Line 38, "et al," should read --et al.,--;
Line 57, "applications" should read --applications.--; and
Line 63, "CIC" should read --CIC.--.

COLUMN 4

Line 10, "(need to define)" should be deleted;
Line 11, "(check)" should be deleted;
Line 22, "cost effective." should read --cost-effective.--;
Line 24, "mixtures" should read --mixture--; and
Line 66, "form" should read --from--.

COLUMN 5

Line 2, "a" should read --an--;
Line 31, "a" should read --an--; and
Line 33, "a" (both occurrences) should read --an--.

COLUMN 6

Line 14, "Xyrl" should read --Xyrl.--; and
Line 24, "overexpreses" should read --overexpresses--.

COLUMN 7

Line 8, "(stripped" should read --(striped--.

COLUMN 8

Line 65, "*crassa*" should read --*crassa,*--.

COLUMN 9

Lines 14-15, "Add a sentence or two about the domain structure and where the various domains start and stop" should be deleted;
Line 18, "a" (both occurrences) should read --an--;
Line 19, "a" should read --an--; and
Line 27, "a" should read --an--.

COLUMN 10

Line 24, "without" should read --Without--;
Line 28, "a" (first occurrence) should read --an--; and
Line 53, "expressed" should read --expression--.

COLUMN 11

Line 3, "construct" should read --construct.--;
Line 4, "A" should read --An--;
Line 5, "a" (second occurrence) should read --an--;
Line 14, "o rxylanase" should read --or xylanase--; and
Line 38, "it is" should read --they are--.

COLUMN 12

Line 8, "over express" should read --overexpress--;
Line 16, "a" (first occurrence) should read --an--;
Line 22, "a" should read --an--;
Line 25, "a" (second occurrence) should read --an--; and
Line 39, "a" should read --an--.

COLUMN 13

Line 43, "include, but are" should read --includes, but is--.

COLUMN 15

Line 47, "thereof" should read --thereof.--.

COLUMN 16

Line 12, "carried" should read --carried out--;
Line 30, "litre," should read --liter,--;
Line 32, "litres," should read --liters,--;
Line 33, "litres," should read --liters,--;

CERTIFICATE OF CORRECTION (continued)
U.S. Pat. No. 8,323,931 B2

Line 34, "litres," should read --liters,--;
Line 39, "litres," should read --liters,--; and
Line 62, "a" should read --an--.

COLUMN 17

Line 5, "a" should read --an--; and
Line 13, "a" should read --an--.

COLUMN 19

Line 5, "Swollenin." should read --swollenin.--.

COLUMN 20

Table 3, "(and" should read --and--; and
Footnote "a", "carbohydrates" should read --carbohydrates.--.

COLUMN 22

Line 39, "endoglucanse" should read --endoglucanase--; and
Line 50, "P285-Eaux)," should read --P285-6aux),--.

COLUMN 23

Line 15, "amplication" should read --amplification--; and
Line 30, "acid" should read --acid.--.

COLUMN 24

Line 12, "$ZnSO_4 \cdot 7H_{20}0$." should read --$ZnSO_4 \cdot 7H_2O$.--;
Line 21, "at a" (second occurrence) should be deleted; and
Line 57, "Colour" should read --Color--.

COLUMN 25

Line 21, "2% cellbiose[b]" should read --2% cellobiose[b] --.

COLUMN 26

Line 14, "produced" should read --production--; and
Line 48, "is" should read --are--.

COLUMN 27

Line 12, "20mM" should read --20 min--;
Line 51, "–CH27    5'" should read --CH27 5'– --; and
Line 60, "of" should be deleted.

COLUMN 28

Line 20, "follow." should read --follows.--; and
Line 40, "wild type" should read --wild-type--.

COLUMN 29

Line 15, "scontaining" should read --containing--; and
Line 39, "1M MgSO4•7H$_2$O f.s." should read --1M MgSO$_4$•7H$_2$O f.s.--.

COLUMN 30

Line 54, "ZnSO4•7H$_2$O." should read --ZnSO$_4$•7H$_2$O.--.

COLUMN 33

Line 25, "in" should be deleted;
Line 26, "HDC were" should read --HDC, was--;
Line 38, "fungis" should read --fungi--;
Line 43, "(trains" should read --(strains--; and
Line 65, "manufactures" should read --manufacturer's--.

COLUMN 34

Line 32, "funi" should read --fungi--; and
Line 33, "filamentous" should read --filamentous fungi--.

COLUMN 35

Line 19, "the" (first occurrence) should be deleted; and
Line 56, "Mocrobiol." should read --Microbiol.--.

In the Claims:

COLUMN 99

Line 5, "a" should read --an--;
Line 43, "a" (second occurrence) should read --an--; and
Line 52, "a" should read --an--.

COLUMN 100

Line 15, "comprises" should read --comprises:--; and
Line 16, "a" should read --an--.

COLUMN 101

Line 47, "the" should be deleted.

COLUMN 102

Line 1, "the" should be deleted; and
Line 9, "a" should read --an--.

SEQUENCE LISTING

<160> NUMBER OF SEQ ID NOS: 35

<210> SEQ ID NO 1
<211> LENGTH: 24
<212> TYPE: DNA

-continued

```
<213> ORGANISM: Artificial sequence
<220> FEATURE:
<223> OTHER INFORMATION: Ntf2 qPCR primer forward
<220> FEATURE:
<221> NAME/KEY: Ntf2F
<222> LOCATION: (1)..(24)
<223> OTHER INFORMATION: Ntf2 qPCR primer forward
<220> FEATURE:
<221> NAME/KEY: Ntf2F
<222> LOCATION: (1)..(24)

<400> SEQUENCE: 1
acagagttgg cattgtagac agcg                                          24

<210> SEQ ID NO 2
<211> LENGTH: 24
<212> TYPE: DNA
<213> ORGANISM: Artificial sequence
<220> FEATURE:
<223> OTHER INFORMATION: Ntf2 qPCR primer reverse
<220> FEATURE:
<221> NAME/KEY: Ntf2R
<222> LOCATION: (1)..(24)

<400> SEQUENCE: 2
cgagtaaagc acacaaaccg ccaa                                          24

<210> SEQ ID NO 3
<211> LENGTH: 24
<212> TYPE: DNA
<213> ORGANISM: Artificial sequence
<220> FEATURE:
<223> OTHER INFORMATION: xyr1 qPCR primer forward
<220> FEATURE:
<221> NAME/KEY: xyr1F
<222> LOCATION: (1)..(24)

<400> SEQUENCE: 3
agccagattc tcgagtttga ccct                                          24

<210> SEQ ID NO 4
<211> LENGTH: 24
<212> TYPE: DNA
<213> ORGANISM: Artificial sequence
<220> FEATURE:
<223> OTHER INFORMATION: xyr1 qPCR primer reverse
<220> FEATURE:
<221> NAME/KEY: xyr1R
<222> LOCATION: (1)..(24)

<400> SEQUENCE: 4
gcaagcttcg tgtgccctaa caat                                          24

<210> SEQ ID NO 5
<211> LENGTH: 24
<212> TYPE: DNA
<213> ORGANISM: Artificial sequence
<220> FEATURE:
<223> OTHER INFORMATION: Ace1 qPCR primer forward
<220> FEATURE:
<221> NAME/KEY: Ace1F
<222> LOCATION: (1)..(24)

<400> SEQUENCE: 5
agaaggaaat ggaccgccac atca                                          24

<210> SEQ ID NO 6
<211> LENGTH: 24
<212> TYPE: DNA
<213> ORGANISM: Artificial sequence
```

```
<220> FEATURE:
<223> OTHER INFORMATION: Ace1 qPCR primer reverse
<220> FEATURE:
<221> NAME/KEY: Ace2
<222> LOCATION: (1)..(24)

<400> SEQUENCE: 6
agttcgactc acgcttcgac ttgt                                         24

<210> SEQ ID NO 7
<211> LENGTH: 23
<212> TYPE: DNA
<213> ORGANISM: Artificial sequence
<220> FEATURE:
<223> OTHER INFORMATION: Cbh1 qPCR primer forward
<220> FEATURE:
<221> NAME/KEY: Cbh1Q1F
<222> LOCATION: (1)..(23)

<400> SEQUENCE: 7
gccacagcat gttggcgtag taa                                          23

<210> SEQ ID NO 8
<211> LENGTH: 23
<212> TYPE: DNA
<213> ORGANISM: Artificial sequence
<220> FEATURE:
<223> OTHER INFORMATION: cbh1 qPCR primer reverse
<220> FEATURE:
<221> NAME/KEY: Cbh1Q1R
<222> LOCATION: (1)..(23)

<400> SEQUENCE: 8
gccacagcat gttggcgtag taa                                          23

<210> SEQ ID NO 9
<211> LENGTH: 34
<212> TYPE: DNA
<213> ORGANISM: Artificial sequence
<220> FEATURE:
<223> OTHER INFORMATION: Xyr1 amplification primer forward
<220> FEATURE:
<221> NAME/KEY: xyr1F-CH25
<222> LOCATION: (1)..(34)

<400> SEQUENCE: 9
gcggccgcgg tacctacagc catgctcatc gtgc                              34

<210> SEQ ID NO 10
<211> LENGTH: 34
<212> TYPE: DNA
<213> ORGANISM: Artificial sequence
<220> FEATURE:
<223> OTHER INFORMATION: xyr1 amplification primer reverse
<220> FEATURE:
<221> NAME/KEY: xyr1R-CH26
<222> LOCATION: (1)..(34)

<400> SEQUENCE: 10
gcggccgcgg tacctacagc catgctcatc gtgc                              34

<210> SEQ ID NO 11
<211> LENGTH: 22
<212> TYPE: DNA
<213> ORGANISM: Artificial sequence
<220> FEATURE:
<223> OTHER INFORMATION: cel7b qPCR primer forward
<220> FEATURE:
<221> NAME/KEY: cel7bF
<222> LOCATION: (1)..(22)
```

```
<400> SEQUENCE: 11
atcacccgca agtaccagca aa                                              22

<210> SEQ ID NO 12
<211> LENGTH: 24
<212> TYPE: DNA
<213> ORGANISM: Artificial sequence
<220> FEATURE:
<223> OTHER INFORMATION: cel7b qPCR primer reverse
<220> FEATURE:
<221> NAME/KEY: cel7bR
<222> LOCATION: (1)..(24)

<400> SEQUENCE: 12
ctggctgttg tcgttccaaa tgct                                            24

<210> SEQ ID NO 13
<211> LENGTH: 39
<212> TYPE: DNA
<213> ORGANISM: Artificial sequence
<220> FEATURE:
<223> OTHER INFORMATION: Pbxl1 amplification primer forward
<220> FEATURE:
<221> NAME/KEY: Pbxl1
<222> LOCATION: (1)..(39)

<400> SEQUENCE: 13
ggtacccaat tgagagcttg tctgccttga ttaccatcc                            39

<210> SEQ ID NO 14
<211> LENGTH: 39
<212> TYPE: DNA
<213> ORGANISM: Artificial sequence
<220> FEATURE:
<223> OTHER INFORMATION: Pbxl1 amplification primer reverse
<220> FEATURE:
<221> NAME/KEY: Pbxl1R
<222> LOCATION: (1)..(39)

<400> SEQUENCE: 14
ggtacccaat tgagagcttg tctgccttga ttaccatcc                            39

<210> SEQ ID NO 15
<211> LENGTH: 24
<212> TYPE: DNA
<213> ORGANISM: Artificial sequence
<220> FEATURE:
<223> OTHER INFORMATION: xyn1 qPCR primer forward
<220> FEATURE:
<221> NAME/KEY: xyn1F
<222> LOCATION: (1)..(24)

<400> SEQUENCE: 15
tcatcaactt ctcgggcagc taca                                            24

<210> SEQ ID NO 16
<211> LENGTH: 24
<212> TYPE: DNA
<213> ORGANISM: Artificial sequence
<220> FEATURE:
<223> OTHER INFORMATION: xyn1 qPCR primer reverse
<220> FEATURE:
<221> NAME/KEY: xyn1R
<222> LOCATION: (1)..(24)

<400> SEQUENCE: 16
aggtgccaaa gttctcgacg atgt                                            24
```

```
<210> SEQ ID NO 17
<211> LENGTH: 24
<212> TYPE: DNA
<213> ORGANISM: Artificial sequence
<220> FEATURE:
<223> OTHER INFORMATION: bxl-xyr1 primer forward
<220> FEATURE:
<221> NAME/KEY: bxl-xyr1F
<222> LOCATION: (1)..(24)

<400> SEQUENCE: 17
ttgagcgcag catcactgtg taga                                              24

<210> SEQ ID NO 18
<211> LENGTH: 24
<212> TYPE: DNA
<213> ORGANISM: Artificial sequence
<220> FEATURE:
<223> OTHER INFORMATION: bxl-xyr1 primer reverse
<220> FEATURE:
<221> NAME/KEY: bxl-xyr1R
<222> LOCATION: (1)..(24)

<400> SEQUENCE: 18
aacggatctg cgtctgtgtc tgat                                              24

<210> SEQ ID NO 19
<211> LENGTH: 24
<212> TYPE: DNA
<213> ORGANISM: Artificial sequence
<220> FEATURE:
<223> OTHER INFORMATION: xyn2 qPCR primer forward
<220> FEATURE:
<221> NAME/KEY: xyn2F
<222> LOCATION: (1)..(24)

<400> SEQUENCE: 19
acggctactt ctactcgtac tgga                                              24

<210> SEQ ID NO 20
<211> LENGTH: 24
<212> TYPE: DNA
<213> ORGANISM: Artificial sequence
<220> FEATURE:
<223> OTHER INFORMATION: xyn2 qPCR primer reverse
<220> FEATURE:
<221> NAME/KEY: xyn2R
<222> LOCATION: (1)..(24)

<400> SEQUENCE: 20
tgtagctgcc cgagaagttg atga                                              24

<210> SEQ ID NO 21
<211> LENGTH: 24
<212> TYPE: DNA
<213> ORGANISM: Artificial sequence
<220> FEATURE:
<223> OTHER INFORMATION: bxl1 qPCR primer forward
<220> FEATURE:
<221> NAME/KEY: Bxl1F
<222> LOCATION: (1)..(24)

<400> SEQUENCE: 21
tatacggcca tgctgtttgt tcgc                                              24

<210> SEQ ID NO 22
<211> LENGTH: 24
<212> TYPE: DNA
<213> ORGANISM: Artificial sequence
```

```
<220> FEATURE:
<223> OTHER INFORMATION: bxl1 qPCR primer reverse
<220> FEATURE:
<221> NAME/KEY: bxl1R
<222> LOCATION: (1)..(24)

<400> SEQUENCE: 22
tggaagagtg accaggcttg atgt                                             24

<210> SEQ ID NO 23
<211> LENGTH: 3451
<212> TYPE: DNA
<213> ORGANISM: Trichoderma reesei
<220> FEATURE:
<221> NAME/KEY: xyr1
<222> LOCATION: (1)..(3448)
<220> FEATURE:
<221> NAME/KEY: xyr1
<222> LOCATION: (1)..(3451)

<400> SEQUENCE: 23
atgttgtcca atcctctccg tcgctattct gcctaccccg acatctcctc ggcgtcattt      60
gacccgaact accatggctc acagtcgcat ctccactcga tcaacgtcaa cacattcggc     120
aacagccacc cctatcccat gcagcacctc gcacagcatg cggagctttc gagttcacgc     180
atgataaggg ccagtccggt gcagccaaag cagcgccagg gctctcttat tgctgccagg     240
aagaattcaa cgggtactgc tgggcccatt cggcggagga tcagtcgcgc ttgtgaccag     300
tgcaaccagc ttcgtaccaa gtgcgatggc ttacacccat gtgcccattg tataggtatg     360
tcccttttcc tctacacagt gatgctgcgc tcaagcacat gtactgatcg atcttgttta     420
gaattcggcc ttggatgcga atatgtccga gagagaaaga agcgtggcaa agcttcgcgc     480
aaggatattg ctgcccagca agccgcggcg gctgcagcac aacactccgg ccaggtccag     540
gatggtccag aggatcaaca tcgcaaactc tcacgccagc aaagcgaatc ttcgcgtggc     600
agcgctgagc ttgcccagcc tgcccacgac ccgcctcatg ccacattga gggctctgtc     660 agctccttca gcgacaatgg ccttcccag catgctgcca tgggcggcat ggatggcctg     720
gaagatcacc atggccacgt cggagttgat cctgccctgg ccgaactca gctggaagcg     780 tcatcagcaa tgggcctggg cgcatacggt gaagtccacc ccggctatga gagccccggc     840
atgaatggcc atgtgatggt gccccgtcg tatgggcgcg agaccaccat ggccgggtat     900
tccggtatct cgtatgctgc gcaagccccg agtccggcta cgtatagcag cgacggtaac     960
tttcgactca ccgtcacat ccatgattac ccgctggcaa atgggagctc gccctcatgg    1020
ggagtctcgc tggcctcgcc ttcgaaccag ttccagcttc agctctcgca gcccatcttc    1080
aagcaaagcg atttgcgata tcctgtgctt gagcctctgc tgcctcacct gggaaacatc    1140
ctccccgtgt ctttggcgtg cgatctgatt gacctgtact tctcctcgtc ttcatcagca    1200
cagatgcacc caatgtcccc atacgttctg gccttcgtct tccggaagcg ctccttcttg    1260 cacccacga acccacgaag gtgccagccc gcgctgcttg cgagcatgct gtgggtggcg    1320
gcacagacta gcgaagcgtc cttcttgacg agcctgccgt cggcgaggag caaggtctgc    1380
cagaagctgc tcgagctgac cgttgggctt cttcagcccc tgatccacac cggcaccaac    1440
agcccgtctc ccaagactag ccccgtcgtc ggtgctgctg ccctgggagt tcttggggtg    1500
gccatgccgg gctcgctgaa catggattca ctggccggcg aaacgggtgc ttttggggcc    1560
atagggagcc ttgacgacgt catcacctat gtgcacctcg ccacggtcgt ctcggccagc    1620
gagtacaagg gcgccagcct gcggtggtgg ggtgcggcat ggtctctcgc cagagagctc    1680
```

```
aagcttggcc gtgagctgcc gcctggcaat ccacctgcca accaggagga cggcgagggc    1740
cttagcgaag acgtggatga gcacgacttg aacagaaaca acactcgctt cgtgacggaa    1800
gaggagcgcg aagagcgacg gcgagcatgg tggctcgttt acatcgtcga caggcacctg    1860
gcgctctgct acaaccgccc cttgtttctt ctggacagcg agtgcagcga cttgtaccac    1920
ccgatggacg acatcaagtg gcaggcaggc aaatttcgca gccacgatgc agggaactcc    1980
agcatcaaca tcgatagctc catgacggac gagtttggcg atagtccccg gcggctcgc     2040
ggcgcacact acgagtgccg cggtcgtagc attttTggct acttcttgtc cttgatgaca    2100
atcctgggcg agattgtcga tgtccaccat gctaaaagcc accccggtt cggcgttgga     2160
ttccgctccg cgcgggattg ggacgagcag gttgctgaaa tcacccgaca cctggacatg    2220
tatgaggaga gcctcaagag gttcgtggcc aagtatctgc cattgtcctc aaaggacaag    2280
gagcagcatg agatgcgcga cagtggagcg gtaacagaca tgcaatctcc actctcggtg    2340
cggaccaacg cgtccagccg catgacggag agcgagatcc aggccagcat cgtggtggct    2400
tacagcaccc atgtgatgca tgtcctccac atcctccttg cggataagtg ggatcccatc    2460
aaccttctag acgacgacga cttgtggatc tcgtcggaag gattcgtgac ggcgacgagc    2520
cacgcggtat cggctgccga agctattagc cagattctcg agtttgaccc tggcctggag    2580
tttatgccat tcttctacgg cgtctatctc ctgcagggtt ccttcctcct cctgctcatc    2640
gccgacaagc tgcaggccga agcgtctcca agcgtcatca aggcttgcga gaccattgtt    2700
agggcacacg aagcttgcgt tgtgacgctg agcacagagt atcaggtaag ccctatcagt    2760
tcaaacgtct atcttgctgt gaatcaaaga ctgacttgga catcagcgca actttagcaa    2820
ggttatgcga agcgcgctgg ctctgattcg gggccgtgtg ccggaagatt tagctgagca    2880
gcagcagcga cgacgcgagc ttcttgcact ataccgatgg actggtaacg gaaccggtct    2940
ggccctctaa ggaggccact caatcgtatg acgttggatt ggggactac acaaacgaa     3000
ggcgaccaac atagggggcc gcctctgctg cgatatttca acattgtggc aaatatgaat    3060
atccttttca tttgtcggca agggtgtgtt ttggtttga tttgttcacg gtgttggagg     3120
ctatcttaat actttgggat gtcttgaaga atggtctagg tgggctgagg cgccgggcaa    3180
ggctggtagg atcatgagcg actttatggt tatgacgaaa aagatatccc cttgattatg    3240
tgtacggcag gcactggctc ggacgacatg ttttgtatat tggttgggac tgcgggaatc    3300
tctttgtcgc gatgatgggt tgggctatgt tcggttttga ggatacgatg tcaaattgct    3360
gtatgcctag gtaatatgaa actttatga agagaaacaa aagtgacttg ttgcaaaggt    3420
agcttccaag tgcacgatga gcatggctgt a                                   3451
```

<210> SEQ ID NO 24
<211> LENGTH: 2817
<212> TYPE: DNA
<213> ORGANISM: Trichoderma reesei
<220> FEATURE:
<221> NAME/KEY: xyr1cds
<222> LOCATION: (1)..(2817)

<400> SEQUENCE: 24

```
atgttgtcca atcctctccg tcgctattct gcctaccccg catctcctc ggcgtcattt       60
gacccgaact accatggctc acagtcgcat ctccactcga tcaacgtcaa cacattcggc     120
aacagccacc cctatcccat gcagcacctc gcacagcatg cggagctttc gagttcacgc     180
atgataaggg ccagtccggt gcagccaaag cagcgccagg gctctcttat tgctgccagg     240
aagaattcaa cgggtactgc tgggcccatt cggcggagga tcagtcgcgc ttgtgaccag    300
```

```
tgcaaccagc ttcgtaccaa gtgcgatggc ttacacccat gtgcccattg tataggtatg    360 tccctttcc tctacacagt gatgctgcgc tcaagcacat gtactgatcg atcttgttta    420
gaattcggcc ttggatgcga atatgtccga gagagaaaga agcgtggcaa agcttcgcgc    480
aaggatattg ctgcccagca agccgcggcg gctgcagcac aacactccgg ccaggtccag    540
gatggtccag aggatcaaca tcgcaaactc tcacgccagc aaagcgaatc ttcgcgtggc    600
agcgctgagc ttgcccagcc tgcccacgac ccgcctcatg gccacattga gggctctgtc    660
agctccttca gcgacaatgg cctttcccag catgctgcca tgggcggcat ggatggcctg    720
gaagatcacc atggccacgt cggagttgat cctgccctgg gccgaactca gctggaagcg    780
tcatcagcaa tgggcctggg cgcatacggt gaagtccacc ccggctatga gagcccggc    840 atgaatggcc atgtgatggt gccccgtcg tatggcgcgc agaccaccat ggccgggtat    900
tccggtatct cgtatgctgc gcaagcccg agtccggcta cgtatagcag cgacggtaac    960
tttcgactca ccggtcacat ccatgattac ccgctggcaa atgggagctc gccctcatgg    1020
ggagtctcgc tggcctcgcc ttcgaaccag ttccagcttc agctctcgca gcccatcttc    1080
aagcaaagcg atttgcgata tcctgtgctt gagcctctgc tgcctcacct gggaaacatc    1140
ctccccgtgt ctttggcgtg cgatctgatt gacctgtact tctcctcgtc ttcatcagca    1200
cagatgcacc caatgtcccc atacgttctg gccttcgtct tccggaagcg ctccttcttg    1260
caccccacga acccacgaag gtgccagccc gcgctgcttg cgagcatgct gtgggtggcg    1320
gcacagacta gcgaagcgtc cttcttgacg agcctgccgt cggcgaggag caaggtctgc    1380
cagaagctgc tcgagctgac cgttgggctt cttcagcccc tgatccacac cggcaccaac    1440
agcccgtctc ccaagactag ccccgtcgtc ggtgctgctg ccctgggagt tcttggggtg    1500
gccatgccgg gctcgctgaa catggattca ctggccggcg aaacgggtgc ttttggggcc    1560
atagggagcc ttgacgacgt catcacctat gtgcacctcg ccacggtcgt ctcggccagc    1620
gagtacaagg gcgccagcct gcggtggtgg ggtgcggcat ggtctctcgc cagagagctc    1680
aagcttggcc gtgagctgcc gcctggcaat ccacctgcca accaggagga cggcgagggc    1740
cttagcgaag acgtggatga gcacgacttg aacagaaaca acactcgctt cgtgacggaa    1800
gaggagcgcg aagagcgacg gcgagcatgg tggctcgttt acatcgtcga caggcacctg    1860
gcgctctgct acaaccgccc cttgtttctt ctggacagcg agtgcagcga cttgtaccac    1920
ccgatggacg acatcaagtg gcaggcaggc aaatttcgca gccacgatgc agggaactcc    1980
agcatcaaca tcgatagctc catgacggac gagtttggcg atagtccccg gcggctcgc    2040 ggcgcacact acgagtgccg cggtcgtagc attttggct acttcttgtc cttgatgaca    2100
atcctgggcg agattgtcga tgtccaccat gctaaaagcc accccggtt cggcgttgga    2160 ttccgctccg cgcgggattg ggacgagcag gttgctgaaa tcacccgaca cctggacatg    2220
tatgaggaga gcctcaagag gttcgtggcc aagtatctgc cattgtcctc aaaggacaag    2280
gagcagcatg agatgcgcga cagtggagcg gtaacagaca tgcaatctcc actctcggtg    2340
cggaccaacg cgtccagccg catgacggag agcgagatcc aggccagcat cgtggtggct    2400
tacagcaccc atgtgatgca tgtcctccac atcctccttg cggataagtg ggatcccatc    2460
aaccttctag acgacgacga cttgtggatc tcgtcggaag gattcgtgac ggcgacgagc    2520 cacgcgggtat cggctgccga agctattagc cagattctcg agtttgaccc tggcctggag    2580
tttatgccat tcttctacgg cgtctatctc ctgcagggtt ccttcctcct cctgctcatc    2640
gccgacaagc tgcaggccga agcgtctcca agcgtcatca aggcttgcga gaccattgtt    2700
```

```
agggcacacg aagcttgcgt tgtgacgctg agcacagagt atcaggtaag ccctatcagt    2760
tcaaacgtct atcttgctgt gaatcaaaga ctgacttgga catcagcgca actttag      2817
```

<210> SEQ ID NO 25
<211> LENGTH: 875
<212> TYPE: PRT
<213> ORGANISM: Aspergillus niger
<220> FEATURE:
<221> NAME/KEY: XlnRAniger
<222> LOCATION: (1)..(875)

<400> SEQUENCE: 25

```
Met Ser His Thr Lys Asp Gln Pro Pro Phe Asp Asn Glu Lys Asn Gln
1               5                   10                  15

Ser Thr Gly Ser Gly Phe Arg Asp Ala Leu Gln Arg Asp Pro Leu Val
            20                  25                  30

Glu Ala Arg Ser Ala Val Arg Lys Thr Ser Ser Ser Ala Pro Val Arg
        35                  40                  45

Arg Arg Ile Ser Arg Ala Cys Asp Gln Cys Asn Gln Leu Arg Thr Lys
    50                  55                  60

Cys Asp Gly Gln His Pro Cys Ala His Cys Ile Glu Phe Gly Leu Thr
65                  70                  75                  80

Cys Glu Tyr Ala Arg Glu Arg Lys Lys Arg Gly Lys Ala Ser Lys Lys
                85                  90                  95

Asp Leu Ala Ala Ala Ala Ala Ala Thr Gln Gly Ser Asn Gly His
            100                 105                 110

Ser Gly Gln Ala Asn Ala Ser Leu Met Gly Glu Arg Thr Ser Glu Asp
        115                 120                 125

Ser Arg Pro Gly Gln Asp Val Asn Gly Thr Tyr Asp Ser Ala Phe Glu
    130                 135                 140

Ser His His Leu Ser Ser Gln Pro Ser His Met Gln His Ala Ser Thr
145                 150                 155                 160

Ala Gly Ile Ser Gly Leu His Glu Ser Gln Thr Ala Pro Ser His Ser
                165                 170                 175

Gln Ser Ser Leu Gly Thr Thr Ile Asp Ala Met His Leu Asn His Phe
            180                 185                 190

Asn Thr Met Asn Asp Ser Gly Arg Pro Ala Met Ser Ile Ser Asp Leu
        195                 200                 205

Arg Ser Leu Pro Pro Ser Val Leu Pro Pro Gln Gly Leu Ser Ser Gly
    210                 215                 220

Tyr Asn Ala Ser Ala Phe Ala Leu Val Asn Pro Gln Glu Pro Gly Ser
225                 230                 235                 240

Pro Ala Asn Gln Phe Arg Leu Gly Ser Ser Ala Glu Asn Pro Thr Ala
                245                 250                 255

Pro Phe Leu Gly Leu Ser Pro Gly Gln Ser Pro Gly Trp Leu Pro
            260                 265                 270

Leu Pro Ser Pro Ser Pro Ala Asn Phe Pro Ser Phe Ser Leu His Pro
        275                 280                 285

Phe Ser Ser Thr Leu Arg Tyr Pro Val Leu Gln Pro Val Leu Pro His
    290                 295                 300

Ile Ala Ser Ile Ile Pro Gln Ser Leu Ala Cys Asp Leu Leu Asp Val
305                 310                 315                 320

Tyr Phe Thr Ser Ser Ser Ser His Leu Ser Pro Leu Ser Pro Tyr
                325                 330                 335

Val Val Gly Tyr Ile Phe Arg Lys Gln Ser Phe Leu His Pro Thr Lys
```

```
                    340                 345                 350
Pro Arg Ile Cys Ser Pro Gly Leu Leu Ala Ser Met Leu Trp Val Ala
            355                 360                 365
Ala Gln Thr Ser Glu Ala Ala Phe Leu Thr Ser Pro Pro Ser Ala Arg
            370                 375                 380
Gly Arg Val Cys Gln Lys Leu Leu Glu Leu Thr Ile Gly Leu Leu Arg
385                 390                 395                 400
Pro Leu Val His Gly Pro Ala Thr Gly Glu Ala Ser Pro Asn Tyr Ala
                405                 410                 415
Ala Asn Met Val Ile Asn Gly Val Ala Leu Gly Gly Phe Gly Val Ser
            420                 425                 430
Met Asp Gln Leu Gly Ala Gln Ser Ser Ala Thr Gly Ala Val Asp Asp
            435                 440                 445
Val Ala Thr Tyr Val His Leu Ala Thr Val Val Ser Ala Ser Glu Tyr
        450                 455                 460
Lys Ala Ala Ser Met Arg Trp Trp Thr Ala Ala Trp Ser Leu Ala Arg
465                 470                 475                 480
Glu Leu Lys Leu Gly Arg Glu Leu Pro Pro Asn Val Ser His Ala Arg
                485                 490                 495
Gln Asp Gly Glu Arg Asp Gly Asp Glu Ala Asp Lys Arg His Pro
                500                 505                 510
Pro Thr Leu Ile Thr Ser Leu Gly His Gly Ser Gly Ser Ser Gly Ile
            515                 520                 525
Asn Val Thr Glu Glu Arg Glu Glu Arg Arg Leu Trp Trp Leu
            530                 535                 540
Leu Tyr Ala Thr Asp Arg His Leu Ala Leu Cys Tyr Asn Arg Pro Leu
545                 550                 555                 560
Thr Leu Leu Asp Lys Glu Cys Gly Gly Leu Leu Gln Pro Met Asn Asp
                565                 570                 575
Asp Leu Trp Gln Val Gly Asp Phe Ala Ala Ala Tyr Arg Gln Val
            580                 585                 590
Gly Pro Pro Val Glu Cys Thr Gly His Ser Met Tyr Gly Tyr Phe Leu
            595                 600                 605
Pro Leu Met Thr Ile Leu Gly Gly Ile Val Asp Leu His His Ala Glu
        610                 615                 620
Asn His Pro Arg Phe Gly Leu Ala Phe Arg Asn Ser Pro Glu Trp Glu
625                 630                 635                 640
Arg Gln Val Leu Asp Val Thr Arg Gln Leu Asp Thr Tyr Gly Arg Ser
                645                 650                 655
Leu Lys Glu Phe Glu Ala Arg Tyr Thr Ser Asn Leu Thr Leu Gly Ala
            660                 665                 670
Thr Asp Asn Glu Pro Val Val Glu Gly Ala His Leu Asp His Thr Ser
        675                 680                 685
Pro Ser Gly Arg Ser Ser Thr Val Gly Ser Arg Val Ser Glu Ser
            690                 695                 700
Ile Val His Thr Arg Met Val Ala Tyr Gly Thr His Ile Met His
705                 710                 715                 720
Val Leu His Ile Leu Leu Ala Gly Lys Trp Asp Pro Val Asn Leu Leu
                725                 730                 735
Glu Asp His Asp Leu Trp Ile Ser Ser Glu Ser Phe Val Ser Ala Met
                740                 745                 750
Ser His Ala Val Gly Ala Ala Glu Ala Ala Ala Glu Ile Leu Glu Tyr
            755                 760                 765
```

```
Asp Pro Asp Leu Ser Phe Met Pro Phe Phe Phe Gly Ile Tyr Leu Leu
        770                 775                 780

Gln Gly Ser Phe Leu Leu Leu Ala Ala Asp Lys Leu Gln Gly Asp
785                 790                 795                 800

Ala Ser Pro Ser Val Val Arg Ala Cys Glu Thr Ile Val Arg Ala His
                805                 810                 815

Glu Ala Cys Val Val Thr Leu Asn Thr Glu Tyr Gln Arg Thr Phe Arg
                820                 825                 830

Lys Val Met Arg Ser Ala Leu Ala Gln Val Arg Gly Arg Ile Pro Glu
                835                 840                 845

Asp Phe Gly Glu Gln Gln Gln Arg Arg Arg Glu Val Leu Ala Leu Tyr
        850                 855                 860

Arg Trp Ser Gly Asp Gly Ser Gly Leu Ala Leu
865                 870                 875

<210> SEQ ID NO 26
<211> LENGTH: 1519
<212> TYPE: DNA
<213> ORGANISM: Trichoderma reesei
<220> FEATURE:
<221> NAME/KEY: Pbxl1
<222> LOCATION: (1)..(1519)

<400> SEQUENCE: 26
caattgagag cttgtctgcc ttgattacca tccattccat tggaggtagt agtaaaggat     60 ctgggttttcc tggggaacat acggcaccca aagtgctggc tgcaaggagg attgttccgt    120
cttggtataa tgttgagaaa tgtttcagcc agcgaatgaa cgcaagtgtg gctatttggg    180
ctaattgctt gcacctctgt cgaggcttgt aggcctagcc atgcgttaga tgcaggtaag    240
ctcatatcct gcaattcgtg gactctatgt gcggcgtata tatgcagcta gcaagatacc    300
ggggaacacc gggaaagcat cacactcgaa gccaaacctc agctcgcccg ccaaacactg    360
catcctcagc tacagcgcct aggttgatcg tcgtttcgtc gctcgggatg ctaccagcta    420
taccttagag taacgcgagc agggtgcatt gtatgataca ctggcacgtt tcccccacc    480 cgttcaaact tcttgactcc aattgagctg ttgagatcga aagagatggc ggtagactga    540
caacatggct ataaacgcac cctcaatttc gttgtgatat atgcattgtc aaccccaatc    600
tgaggttcag gtttggcttc cttcgagttc tccaagttct ctgaatcgta tgtccgcatt    660
cattggtatc gaagtttgtg attaatctcg agaatgtgca tacttcagtc acctcaacat    720
acacggaatc cagcctcttc atgaggaatc cttactcctt catacccaa gtgcccgggc    780 agataattgt acccattcac aaatgaactt agactgtact ccgcacttct ttcaggctcc    840
tctctcctca cgatgcccca atgcttgcca ctccacaagg tacatgtagt aatctgcagt    900
tactcccccg cttttgccta cttagccggc aagaatgaga tgcaagtttg ttcctgtcgg    960
gagtattggc taaatggaaa cacaagtaga agaagagaaa cagaaaaggt ccaataccgg   1020
ctattcacaa cggatctgcg tctgtgtctg atagaactag taaaagtcgg cagtatccgc   1080
tgtcatcaag atcatatact aaaacgtaag ctaaacgcaa tggcttggaa aaggggattg   1140
agacagaaga tacaccaacg accacccctg ttagtgacag agatggcagt cattcgacta   1200
gcggctggca attggtgtcc gccttgtatt caggctaaat atctcgaggt gccgggaaat   1260
catggtgagg aggagttggc atgtgtggag ccgtgatgca ggtcggacca caccaagaag   1320
ctggggtagc atttccgtcc cgtatggggt taacatgggg taacatgctg gaattgcaaa   1380
tgatgcatgg gggaagaatg caacatcgtc atcgtcatac cgctcaattt aaatattggg   1440
```

```
cttttccggg gatcagatgg aagaaggcaa cagagagaga gacaaggaag accgtgagcc    1500
attgaaggac agccggacg                                                 1519
```

<210> SEQ ID NO 27
<211> LENGTH: 941
<212> TYPE: PRT
<213> ORGANISM: Trichoderma reesei
<220> FEATURE:
<221> NAME/KEY: Xyr1Treesei
<222> LOCATION: (1)..(941)

<400> SEQUENCE: 27

```
Tyr Met Leu Ser Asn Pro Leu Arg Arg Tyr Ser Ala Tyr Pro Asp Ile
1               5                   10                  15

Ser Ser Ala Ser Phe Asp Pro Asn Tyr His Gly Ser Gln Ser His Leu
            20                  25                  30

His Ser Ile Asn Val Asn Thr Phe Gly Asn Ser His Pro Tyr Pro Met
        35                  40                  45

Gln His Leu Ala Gln His Ala Glu Leu Ser Ser Ser Arg Met Ile Arg
    50                  55                  60

Ala Ser Pro Val Gln Pro Lys Gln Arg Gln Gly Ser Leu Ile Ala Ala
65                  70                  75                  80

Arg Lys Asn Ser Thr Gly Thr Ala Gly Pro Ile Arg Arg Arg Ile Ser
                85                  90                  95

Arg Ala Cys Asp Gln Cys Asn Gln Leu Arg Thr Lys Cys Asp Gly Leu
            100                 105                 110

His Pro Cys Ala His Cys Ile Glu Phe Gly Leu Gly Cys Glu Tyr Val
        115                 120                 125

Arg Glu Arg Lys Lys Arg Gly Lys Ala Ser Arg Lys Asp Ile Ala Ala
    130                 135                 140

Gln Gln Ala Ala Ala Ala Ala Gln His Ser Gly Gln Val Gln Asp
145                 150                 155                 160

Gly Pro Glu Asp Gln His Arg Lys Leu Ser Arg Gln Ser Glu Ser
                165                 170                 175

Ser Arg Gly Ser Ala Glu Leu Ala Gln Pro Ala His Asp Pro Pro His
            180                 185                 190

Gly His Ile Glu Gly Ser Val Ser Ser Phe Ser Asp Asn Gly Leu Ser
        195                 200                 205

Gln His Ala Ala Met Gly Gly Met Asp Gly Leu Glu Asp His His Gly
    210                 215                 220

His Val Gly Val Asp Pro Ala Leu Gly Arg Thr Gln Leu Glu Ala Ser
225                 230                 235                 240

Ser Ala Met Gly Leu Gly Ala Tyr Gly Glu Val His Pro Gly Tyr Glu
                245                 250                 255

Ser Pro Gly Met Asn Gly His Val Met Val Pro Ser Tyr Gly Ala
            260                 265                 270

Gln Thr Thr Met Ala Gly Tyr Ser Gly Ile Ser Tyr Ala Ala Gln Ala
        275                 280                 285

Pro Ser Pro Ala Thr Tyr Ser Asp Gly Asn Phe Arg Leu Thr Gly
    290                 295                 300

His Ile His Asp Tyr Pro Leu Ala Asn Gly Ser Ser Pro Ser Trp Gly
305                 310                 315                 320

Val Ser Leu Ala Ser Pro Ser Asn Gln Phe Gln Leu Gln Leu Ser Gln
                325                 330                 335

Pro Ile Phe Lys Gln Ser Asp Leu Arg Tyr Pro Val Leu Glu Pro Leu
            340                 345                 350
```

```
Leu Pro His Leu Gly Asn Ile Leu Pro Val Ser Leu Ala Cys Asp Leu
        355                 360                 365

Ile Asp Leu Tyr Phe Ser Ser Ser Ser Ala Gln Met His Pro Met
370                 375                 380

Ser Pro Tyr Val Leu Gly Phe Val Phe Arg Lys Arg Ser Phe Leu His
385                 390                 395                 400

Pro Thr Asn Pro Arg Arg Cys Gln Pro Ala Leu Leu Ala Ser Met Leu
                405                 410                 415

Trp Val Ala Ala Gln Thr Ser Glu Ala Ser Phe Leu Thr Ser Leu Pro
                420                 425                 430

Ser Ala Arg Ser Lys Val Cys Gln Lys Leu Leu Glu Leu Thr Val Gly
            435                 440                 445

Leu Leu Gln Pro Leu Ile His Thr Gly Thr Asn Ser Pro Ser Pro Lys
        450                 455                 460

Thr Ser Pro Val Val Gly Ala Ala Leu Gly Val Leu Gly Val Ala
465                 470                 475                 480

Met Pro Gly Ser Leu Asn Met Asp Ser Leu Ala Gly Glu Thr Gly Ala
                485                 490                 495

Phe Gly Ala Ile Gly Ser Leu Asp Asp Val Ile Thr Tyr Val His Leu
                500                 505                 510

Ala Thr Val Val Ser Ala Ser Glu Tyr Lys Gly Ala Ser Leu Arg Trp
            515                 520                 525

Trp Gly Ala Ala Trp Ser Leu Ala Arg Glu Leu Lys Leu Gly Arg Glu
        530                 535                 540

Leu Pro Pro Gly Asn Pro Ala Asn Gln Glu Asp Gly Glu Gly Leu
545                 550                 555                 560

Ser Glu Asp Val Asp Glu His Asp Leu Asn Arg Asn Asn Thr Arg Phe
                565                 570                 575

Val Thr Glu Glu Glu Arg Glu Val Arg Arg Arg Ala Trp Trp Leu Val
                580                 585                 590

Tyr Ile Val Asp Arg His Leu Ala Leu Cys Tyr Asn Arg Pro Leu Phe
            595                 600                 605

Leu Leu Asp Ser Glu Cys Ser Asp Leu Tyr His Pro Met Asp Asp Ile
        610                 615                 620

Lys Trp Gln Ala Gly Lys Phe Arg Ser His Asp Ala Gly Asn Ser Ser
625                 630                 635                 640

Ile Asn Ile Asp Ser Ser Met Thr Asp Glu Phe Gly Asp Ser Pro Arg
                645                 650                 655

Ala Ala Arg Gly Ala His Tyr Glu Cys Arg Gly Arg Ser Ile Phe Gly
                660                 665                 670

Tyr Phe Leu Ser Leu Met Thr Ile Leu Gly Glu Ile Val Asp Val His
            675                 680                 685

His Ala Lys Ser His Pro Arg Phe Gly Val Gly Phe Arg Ser Ala Arg
        690                 695                 700

Asp Trp Asp Glu Gln Val Ala Glu Ile Thr Arg His Leu Asp Met Tyr
705                 710                 715                 720

Glu Glu Ser Leu Lys Arg Phe Val Ala Lys His Leu Pro Leu Ser Ser
                725                 730                 735

Lys Asp Lys Glu Gln His Glu Met His Asp Ser Gly Ala Val Thr Asp
                740                 745                 750

Met Gln Ser Pro Leu Ser Val Arg Thr Asn Ala Ser Ser Arg Met Thr
            755                 760                 765

Glu Ser Glu Ile Gln Ala Ser Ile Val Val Ala Tyr Ser Thr His Val
```

```
                770              775             780
Met His Val Leu His Ile Leu Ala Asp Lys Trp Asp Pro Ile Asn
785                 790                 795                 800

Leu Leu Asp Asp Asp Leu Trp Ile Ser Ser Glu Gly Phe Val Thr
                805                 810                 815

Ala Thr Ser His Ala Val Ser Ala Glu Ala Ile Ser Gln Ile Leu
                820                 825                 830

Glu Phe Asp Pro Gly Leu Glu Phe Met Pro Phe Phe Tyr Gly Val Tyr
                835                 840                 845

Leu Leu Gln Gly Ser Phe Leu Leu Leu Ile Ala Asp Lys Leu Gln
                850                 855                 860

Ala Glu Ala Ser Pro Ser Val Ile Lys Ala Cys Glu Thr Ile Val Arg
865                 870                 875                 880

Ala His Glu Ala Cys Val Val Thr Leu Ser Thr Glu Tyr Gln Arg Asn
                    885                 890                 895

Phe Ser Lys Val Met Arg Ser Ala Leu Ala Leu Ile Arg Gly Arg Val
                900                 905                 910

Pro Glu Asp Leu Ala Glu Gln Gln Gln Arg Arg Arg Glu Leu Leu Ala
                915                 920                 925

Leu Tyr Arg Trp Thr Gly Asn Gly Thr Gly Leu Ala Leu
                930                 935                 940
```

<210> SEQ ID NO 28
<211> LENGTH: 875
<212> TYPE: PRT
<213> ORGANISM: Aspergillus nidulans
<220> FEATURE:
<221> NAME/KEY: XlnRAnidulans
<222> LOCATION: (1)..(875)

<400> SEQUENCE: 28

```
Met Ser Gln Ser Gln Ser Gln Thr Ile Gly Leu Asp Thr Leu Ala Glu
1               5                   10                  15

Gly Ser Gln Tyr Val Leu Glu Gln Leu Gln Leu Ser Arg Glu Gly Gly
                20                  25                  30

Asn Ser Glu Asn Asn Ser Thr Phe Lys Pro Ser Ser Val Arg Asp Ser
            35                  40                  45

Leu Ala Glu Ala Arg Ser Met Ile Arg Lys Asn Ser Ser Ala Pro
    50                  55                  60

Val Arg Arg Arg Ile Ser Arg Ala Cys Asp Gln Cys Asn Gln Leu Arg
65              70                  75                  80

Thr Lys Cys Asp Gly Gln Asn Pro Cys Ala His Cys Ile Glu Phe Gly
                85                  90                  95

Leu Thr Cys Glu Tyr Ala Arg Glu Arg Lys Lys Arg Gly Lys Ala Ser
                100                 105                 110

Lys Lys Asp Ile Ala Ala Ala Ala Ala Ala Gly His Gln Gly Gly
                115                 120                 125

Met Gly Asn Arg Ser Pro Thr Asp Arg Arg Leu Ser Gln Glu Pro Gly
130                 135                 140

Gly Arg Tyr Asp Ser Val Leu Glu Ala Ser Arg Val Gln Ser His Leu
145                 150                 155                 160

Pro Ala Asn Gly Leu Ser Ser Ile His Asn Thr Gln Ala Ala His Ser
                165                 170                 175

Gln Pro Pro Leu Gly Ser Ala Leu Asp Ala Leu His Leu Asn His Phe
                180                 185                 190

Thr Gln Leu Asn Glu Ser Gly Arg Ser Gln Met Pro Val Ser Asp Leu
```

-continued

```
                195                 200                 205
Arg Ser Leu Gln Ile Leu His Asn Asn Pro Arg Ser Pro Ser Ala Leu
210                     215                 220
Pro His Gly Leu Asn Ala Tyr Asn Asp Asn Thr Phe Ser Leu Leu Asn
225                 230                     235                 240
Ser Gln Glu Pro Asn Thr Thr Ser Leu Asn His Phe Arg Leu Gly Asn
                245                     250                 255
Ser Thr Asp Asn Pro Ser Ala Gln Phe Leu Gly Leu Ser Pro Pro Ala
            260                 265                 270
Gln Ser Pro Gly Trp Leu Pro Leu Pro Ser Pro Ser Pro Ala Asn Phe
        275                 280                 285
Pro Ser Phe Pro Met Ala Pro Phe Ser Gly Thr Ser Leu Arg Tyr Pro
290                 295                 300
Val Leu Gln Pro Val Leu Pro His Ile Ala Ser Ile Ile Pro Gln Ser
305                 310                 315                 320
Leu Ala Cys Asp Leu Leu Asp Leu Tyr Phe Thr Ser Ser Ser Ser Ser
                325                 330                 335
His Leu Ser Pro Gln Ser Pro Tyr Val Val Gly Tyr Ile Phe Arg Lys
            340                 345                 350
Gln Ser Phe Leu His Pro Thr Lys Pro Arg Val Cys Ser Pro Gly Leu
        355                 360                 365
Leu Ala Ser Met Leu Trp Val Gly Ala Gln Thr Ser Asp Ala Pro Phe
370                 375                 380
Leu Thr Ser Pro Pro Ser Ala Arg Gly Arg Val Cys Gln Lys Leu Leu
385                 390                 395                 400
Glu Leu Thr Ile Gly Leu Leu Arg Pro Leu Ile His Gly Pro Ala Leu
                405                 410                 415
Gly Glu Ala Ser Pro Asn Tyr Ala Ala Asn Met Val Ile Asn Gly Val
            420                 425                 430
Ala Leu Gly Gly Phe Gly Val Ser Met Asp Gln Leu Gly Ala Gln Ser
        435                 440                 445
Thr Ala Thr Gly Ala Val Asp Asp Val Ala Thr Tyr Val His Leu Ala
450                 455                 460
Thr Val Val Ser Ala Ser Glu Tyr Lys Ala Ala Ser Met Arg Trp Trp
465                 470                 475                 480
Thr Ala Ala Trp Ser Leu Ala Arg Glu Leu Lys Leu Gly Arg Glu Leu
                485                 490                 495
Pro Pro Asn Ala Ser Gln Pro Gly Gln Asp Gly Glu Arg Glu Asn Glu
            500                 505                 510
Gly Asp Asn Pro Ser Lys Arg Asn Gln Ser Leu His Gly Gly Asn Ser
        515                 520                 525
Asn Val Asn Val Thr Glu Glu Glu Arg Glu Glu Arg Arg Arg Leu Trp
530                 535                 540
Trp Leu Leu Tyr Ala Thr Asp Arg His Leu Ala Leu Cys Tyr Asn Arg
545                 550                 555                 560
Pro Leu Thr Leu Leu Asp Lys Glu Cys Ser Gln Leu Leu Gln Pro Met
                565                 570                 575
Asn Asp Asp Leu Trp Gln Ala Gly Asp Phe Pro Ala Ala Thr Tyr Arg
            580                 585                 590
Ala Val Gly Pro Pro Ile Glu Cys Thr Ala Thr Gly Met Phe Gly Tyr
        595                 600                 605
Phe Leu Pro Leu Met Thr Ile Leu Gly Gly Ile Asp Leu Gln Gln
610                 615                 620
```

```
Ala Arg Glu His Pro Arg Tyr Gly Leu Thr Phe Arg Ser Gly Pro Asp
625                 630                 635                 640

Leu Asp Gln Tyr Ile Met Ala Ile Thr Gln Gln Leu Asp Ala Tyr Gly
            645                 650                 655

Gln Ser Leu Lys Asp Phe Glu Ala Arg Tyr Ile Asn Ser Leu Ala Leu
                660                 665                 670

Ala Glu Asn Glu Pro Pro Glu Asn Pro His Ile Asp His Leu Ser Pro
            675                 680                 685

Ser Gly Arg Ser Ser Ser Thr Val Gly Ser Arg Val Asn Glu Ser Ile
690                 695                 700

Val His Thr Lys Met Val Val Ala Tyr Gly Thr His Ile Met His Val
705                 710                 715                 720

Leu Tyr Val Leu Leu Ala Gly Lys Trp Asp Pro Ile Asn Leu Leu Glu
                725                 730                 735

Asp His Asp Met Trp Ile Ser Ser Glu Ser Phe Leu Ala Ala Met Ser
            740                 745                 750

His Ala Val Gly Ala Ala Glu Ala Ala Ala Asp Ile Leu Glu Tyr Asp
                755                 760                 765

Pro Asp Leu Ser Phe Met Pro Phe Phe Phe Gly Ile Tyr Leu Leu Gln
770                 775                 780

Gly Ser Phe Leu Leu Leu Ala Ala Asp Lys Leu Gln Gly Asp Ala
785                 790                 795                 800

Asn Pro Ser Val Val Arg Ala Cys Glu Thr Ile Val Arg Ala His Glu
                805                 810                 815

Ala Cys Val Val Thr Leu Asn Thr Glu Tyr Gln Arg Thr Phe Arg Lys
            820                 825                 830

Val Met Arg Ser Ala Leu Ala Gln Val Arg Gly Arg Val Pro Asp Asp
                835                 840                 845

Phe Gly Glu Gln Gln Gln Arg Arg Arg Glu Val Leu Ser Leu Tyr Arg
850                 855                 860

Trp Thr Gly Asp Gly Thr Gly Leu Ala Leu Ser
865                 870                 875

<210> SEQ ID NO 29
<211> LENGTH: 875
<212> TYPE: PRT
<213> ORGANISM: Aspergillus kawachii
<220> FEATURE:
<221> NAME/KEY: XlnRAkawachii
<222> LOCATION: (1)..(875)

<400> SEQUENCE: 29

Met Ser His Ala Lys Asp Gln Pro Leu Phe Asp Asp Glu Arg Asn Gln
1               5                   10                  15

Ser Ala Gly Ser Gly Phe Lys Asn Thr Leu Gln Arg Asp Pro Leu Val
                20                  25                  30

Glu Ala Arg Ser Ala Ile Arg Lys Asn Ser Ser Ala Pro Val Arg
            35                  40                  45

Arg Arg Ile Ser Arg Ala Cys Asp Gln Cys Asn Gln Leu Arg Thr Lys
        50                  55                  60

Cys Asp Gly Gln His Pro Cys Ala His Cys Ile Glu Phe Gly Leu Thr
65                  70                  75                  80

Cys Glu Tyr Ala Arg Glu Arg Lys Lys Arg Gly Lys Ala Ser Lys Lys
                85                  90                  95

Asp Leu Ala Ala Ala Ala Ala Ala Thr His Gly Ser Asn Gly His
            100                 105                 110
```

```
Ser Gly Gln Ala Asn Ala Ser Leu Met Ala Glu Arg Thr Ser Glu Asp
        115                 120                 125

Ser Arg Pro Ala Gln Asp Val Asn Gly Arg Tyr Asp Ser Thr Phe Glu
    130                 135                 140

Ser His Ile Ser Ser Gln Pro Ser His Met Gln His Ala Asn Asn
145                 150                 155                 160

Ala Gly Ile Ser Gly Leu His Asp Ser Gln Thr Ala Pro Ser His Ser
                165                 170                 175

Gln Pro Ser Leu Gly Thr Thr Ile Asp Ala Met His Leu Gly His Phe
            180                 185                 190

Asn Thr Leu Asn Asp Ser Gly Arg Pro Ala Met Ser Met Ser Asp Leu
        195                 200                 205

Arg Ser Leu Pro Pro Ser Val Leu Pro Gln Gly Leu Ser Ser Gly
    210                 215                 220

Tyr Asn Ala Ser Ala Phe Ala Leu Val Asn Pro Gln Glu Pro Gly Ser
225                 230                 235                 240

Pro Ala Asn Gln Phe Arg Leu Gly Ser Ser Ala Glu Asn Pro Thr Ala
                245                 250                 255

Pro Phe Leu Gly Leu Ser Pro Gly Gln Ser Pro Gly Trp Leu Pro
            260                 265                 270

Leu Pro Ser Pro Ser Pro Ala Asn Phe Pro Ser Phe Ser Leu His Pro
        275                 280                 285

Phe Ser Ser Thr Leu Arg Tyr Pro Val Leu Gln Pro Val Leu Pro His
290                 295                 300

Ile Ala Ser Ile Ile Pro Gln Ser Leu Ala Cys Asp Leu Leu Asp Val
305                 310                 315                 320

Tyr Phe His Ser Ser Pro Ser His Leu Ser Pro Ser Ser Pro Tyr
                325                 330                 335

Val Val Gly Tyr Ile Phe Arg Lys Gln Ser Phe Leu His Pro Thr Lys
                340                 345                 350

Pro Arg Leu Cys Ser Ser Gly Leu Leu Ala Ser Met Leu Trp Val Ala
        355                 360                 365

Ala Gln Thr Ser Glu Ala Pro Phe Leu Thr Ser Pro Ser Ala Arg
    370                 375                 380

Gly Arg Val Cys Gln Lys Leu Leu Glu Leu Thr Ile Gly Leu Leu Arg
385                 390                 395                 400

Pro Leu Val His Gly Pro Ala Thr Gly Glu Ala Ser Pro Asn Tyr Ala
                405                 410                 415

Ala Asn Met Val Ile Asn Gly Val Ala Leu Gly Gly Phe Gly Val Ser
                420                 425                 430

Met Asp Gln Leu Gly Ala Gln Ser Ser Ala Thr Gly Ala Val Asp Asp
        435                 440                 445

Val Ala Thr Tyr Val His Leu Ala Thr Val Val Ser Ala Ser Glu Tyr
    450                 455                 460

Lys Ala Ala Ser Met Arg Trp Trp Thr Ala Ala Trp Ser Leu Ala Arg
465                 470                 475                 480

Glu Leu Lys Leu Gly Arg Glu Leu Pro Pro Asn Val Ser His Ala Arg
                485                 490                 495

Gln Asp Gly Glu Arg Asp Gly Asp Glu Ala Asp Arg Arg His Pro
            500                 505                 510

Pro Thr Leu Ile Thr Ser Leu Gly His Gly Pro Gly Ser Ser Gly Ile
        515                 520                 525

Asn Val Thr Glu Glu Glu Arg Glu Glu Arg Arg Arg Leu Trp Trp Leu
    530                 535                 540
```

```
Leu Tyr Ala Thr Asp Arg His Leu Ala Leu Cys Tyr Asn Arg Pro Leu
545                 550                 555                 560

Thr Leu Leu Asp Lys Glu Cys Gly Gly Leu Leu Gln Pro Met Asn Asp
            565                 570                 575

Asp Leu Trp Gln Val Gly Asp Phe Ala Ala Ala Tyr Arg Gln Val
        580                 585                 590

Gly Pro Pro Val Glu Cys Thr Gly His Ser Met Tyr Gly Tyr Phe Leu
        595                 600                 605

Pro Leu Met Thr Ile Leu Gly Gly Ile Val Asp Leu His His Ala Glu
        610                 615                 620

Asn His Pro Arg Phe Gly Leu Ala Phe Arg Asn Ser Pro Glu Trp Glu
625                 630                 635                 640

Arg Gln Val Gln Asp Val Thr Arg Gln Leu Asp Thr Tyr Gly Arg Ser
            645                 650                 655

Leu Lys Glu Phe Glu Ala Arg Tyr Thr Ser Asn Leu Thr Leu Gly Thr
            660                 665                 670

Ala Glu Asn Glu Pro Ala Val Glu Gly Ala His Leu Asp His Thr Ser
        675                 680                 685

Pro Ser Gly Arg Ser Ser Thr Val Gly Ser Arg Val Ser Gly Ser
        690                 695                 700

Ile Met His Thr Arg Met Val Ala Tyr Gly Thr His Ile Met His
705                 710                 715                 720

Val Leu His Ile Leu Leu Ala Gly Lys Trp Asp Pro Val Asn Leu Leu
            725                 730                 735

Glu Asp His Asp Leu Trp Ile Ser Ser Glu Ser Phe Val Ser Ala Met
            740                 745                 750

Ser His Ala Val Gly Ala Ala Glu Ala Ala Glu Ile Leu Glu His
        755                 760                 765

Asp Pro Asp Leu Ser Phe Met Pro Phe Phe Gly Ile Tyr Leu Leu
        770                 775                 780

Gln Gly Ser Phe Leu Leu Leu Ala Ala Asp Lys Leu Gln Gly Asp
785                 790                 795                 800

Ala Ser Pro Ser Val Val Arg Ala Cys Glu Thr Ile Val Arg Ala His
            805                 810                 815

Glu Ala Cys Val Val Thr Leu Asn Thr Glu Tyr Gln Arg Thr Phe Arg
            820                 825                 830

Lys Val Met Arg Ser Ala Leu Ala Gln Val Arg Gly Arg Ile Pro Glu
            835                 840                 845

Asp Phe Gly Glu Gln Gln Gln Arg Arg Arg Glu Val Leu Ala Leu Tyr
            850                 855                 860

Arg Trp Ser Gly Asp Gly Ser Gly Leu Ala Leu
865                 870                 875

<210> SEQ ID NO 30
<211> LENGTH: 971
<212> TYPE: PRT
<213> ORGANISM: Aspergillus oryzae
<220> FEATURE:
<221> NAME/KEY: AoXlnR
<222> LOCATION: (1)..(971)

<400> SEQUENCE: 30

Met Ser Thr Thr Ser Ile Gln His Phe Thr Ser Ser Phe Ser Pro Phe
1               5                   10                  15

Ser Ser Gly Thr Gln Pro Val Gly Met Ala Gln Ser Gln Thr Val Gly
            20                  25                  30
```

```
Leu Asp Thr Leu Ala Glu Gly Ser Gln Tyr Ala Leu Glu Gln Leu Gln
         35                  40                  45
Leu Ser Arg Glu Ala Asn Gly Ala Ser Ala Val Asp Gly Gly Val Pro
 50                  55                  60
Asn Pro Leu Arg Ser Ser Ile Ser Lys Pro Gln Gly Gln Gln Leu Tyr
 65                  70                  75                  80
Ser Asp Glu Ser Ser Ala Gln His Thr Gln Asn Ala Thr Thr Gly Phe
                 85                  90                  95
Arg Asn Leu Pro Gln Arg Asp Gln Leu Ala Glu Ala Arg Ser Thr Ile
                100                 105                 110
Arg Lys Ser Ser Asn Ser Gly Pro Val Arg Arg Ile Ser Arg Ala
             115                 120                 125
Cys Asp Gln Cys Asn Gln Leu Arg Thr Lys Cys Asp Gly Gln Asn Pro
130                 135                 140
Cys Ala His Cys Ile Glu Phe Gly Leu Thr Cys Glu Tyr Ala Arg Glu
145                 150                 155                 160
Arg Lys Lys Arg Gly Lys Ala Ser Lys Lys Asp Leu Ala Ala Ala
             165                 170                 175
Ala Ala Val Ala Asn Asn Gly Thr Ala Pro Thr Ser Asn Gly Asn Thr
             180                 185                 190
Ser Asn Asp Ser Val Ser Ser Ala Lys Arg His Thr Pro Ser Asp Gly
             195                 200                 205
Gln Ser Thr Gln Glu Val Ser Gly Arg Tyr Asp Pro Asn Phe Asp Ala
             210                 215                 220
Ser Arg Asn Leu Ala Thr Ala Gly Gln Ser Gln Leu Gly Gln His Ser
225                 230                 235                 240
Asp Met Ser Gly Met Ala Gly Met Gln Gly Ser Gln Gln Thr Pro His
                 245                 250                 255
Ser Gln Pro Ser Leu Gly Gly Ala Ile Asp Ala Ile His Leu Asn His
             260                 265                 270
Phe Asn Thr Leu Asn Asp Ser Asn Arg Pro Gln Met Ser Val Pro Asp
             275                 280                 285
Leu Arg Ser Leu Gln Met Leu His Pro Ser Gly Ala Asn Thr Arg Ser
             290                 295                 300
Pro Ser Gly Ala Leu Pro Pro Gln Gly Met Asn Ser Gly Tyr Asn Asp
305                 310                 315                 320
Gly Ala Tyr Ser Leu Met Asn Ala Ser Glu Ala Asn His Pro Ser Ile
                 325                 330                 335
Asn Gln Tyr Arg Leu Gly Asn Ser Ala Glu Asn Pro Pro Ala Pro Phe
             340                 345                 350
Leu Gly Leu Ser Pro Pro Ala Gln Ser Pro Gly Trp Leu Ser Leu Pro
             355                 360                 365
Ser Pro Ser Pro Ala Asn Phe Ala Ser Phe Ser Met Pro Pro Phe Ser
370                 375                 380
Ser Thr Leu Arg Tyr Pro Val Leu Gln Pro Val Leu Pro His Ile Ala
385                 390                 395                 400
Ser Ile Ile Pro Gln Ser Leu Ala Cys Asp Leu Leu Asp Val Tyr Phe
             405                 410                 415
Thr Ser Phe Ser Pro Ser His Leu Ser Pro Gln Ser Pro Tyr Val Val
             420                 425                 430
Gly Tyr Ile Phe Arg Lys Gln Ser Phe Leu His Pro Thr Lys Pro Arg
             435                 440                 445
Val Cys Ser Pro Gly Leu Leu Ala Ser Met Leu Trp Val Ala Ala Gln
```

-continued

```
              450                 455                 460
Thr Ser Asp Ala Ala Phe Leu Thr Ser Pro Ser Ala Arg Gly Arg
465                 470                 475                 480

Val Cys Gln Lys Leu Leu Glu Leu Thr Val Gly Leu Leu Arg Pro Leu
                485                 490                 495

Ile His Gly Pro Ala Pro Gly Glu Thr Ser Pro Asn Tyr Ala Ala Asn
                500                 505                 510

Met Val Ile Asn Gly Val Ala Leu Gly Gly Phe Gly Val Ser Met Asp
                515                 520                 525

Gln Leu Gly Ala Gln Ser Ser Ala Thr Gly Ala Val Asp Asp Val Ala
            530                 535                 540

Thr Tyr Val His Leu Ala Thr Val Ile Ser Ala Ser Glu Tyr Lys Ala
545                 550                 555                 560

Ala Ser Met Arg Trp Trp Thr Ala Ala Trp Ser Leu Ala Arg Glu Leu
                565                 570                 575

Lys Leu Gly Arg Glu Leu Pro Pro Asn Ala Pro Gln Pro Arg Gln Asp
                580                 585                 590

Gly Glu Pro Glu Asp Asp Thr Asp Val Asp Met Ser Lys Arg Asn Leu
                595                 600                 605

Pro Pro Leu Ile Thr Ser Val Gly Gly Asn Ser Gly Ser Thr Ile Leu
610                 615                 620

Asn Val Thr Glu Glu Arg Glu Glu Arg Arg Arg Leu Trp Trp Leu
625                 630                 635                 640

Leu Tyr Ala Thr Asp Arg His Leu Ala Leu Cys Tyr Asn Arg Pro Leu
                645                 650                 655

Thr Leu Leu Asp Lys Glu Cys Glu Gly Leu Leu Gln Pro Met Asn Asp
                660                 665                 670

Asp Leu Trp Gln Ala Gly Asp Phe Ala Gly Ala Thr Tyr Arg Gln Val
                675                 680                 685

Gly Pro Gln Val Glu Cys Thr Gly His Ser Met Phe Gly Phe Leu
                690                 695                 700

Pro Leu Met Thr Ile Leu Gly Glu Ile Val Asp Leu Gln Gln Ala Lys
705                 710                 715                 720

Glu His Pro Arg Phe Gly Arg Val Phe Arg Asn Ser Ala Asp Trp Asp
                725                 730                 735

His Gln Val Leu Glu Ile Thr Arg Gln Leu Asp Thr Tyr Ala Gln Ser
                740                 745                 750

Leu Lys Glu Phe Glu Ala Arg Tyr Thr Ser Ser Leu Ala Leu Gly Ala
                755                 760                 765

Gly Glu Ser Glu Ala Ala Ile Glu Gly Ser His Leu Asp His Val Ser
                770                 775                 780

Pro Ser Gly Arg Ser Thr Ser Thr Ala Gly Ser Arg Val Asn Glu Ser
785                 790                 795                 800

Ile Val His Thr Lys Met Val Ala Tyr Gly Thr His Ile Met His
                805                 810                 815

Val Leu His Val Leu Leu Ala Gly Lys Trp Asp Pro Ile Asn Leu Leu
                820                 825                 830

Glu Asp His Asp Leu Trp Ile Ser Ser Glu Ser Phe Ile Ala Ala Met
                835                 840                 845

Ser His Ala Val Gly Ala Ala Asp Ala Ala Asp Ile Leu Glu Tyr
            850                 855                 860

Asp Pro Asp Ile Thr Phe Met Pro Phe Phe Gly Ile Tyr Leu Leu
865                 870                 875                 880
```

-continued

```
Gln Gly Ser Phe Leu Leu Leu Ala Ala Asp Lys Leu Gln Gly Asp
            885                 890                 895

Val Ser Pro Ser Val Val Arg Ala Cys Glu Thr Ile Val Arg Ala His
        900                 905                 910

Glu Ala Cys Val Val Thr Leu Asn Thr Glu Tyr Gln Arg Thr Phe Arg
    915                 920                 925

Lys Val Met Arg Ser Ala Leu Ala Gln Val Arg Gly Arg Met Pro Glu
930                 935                 940

Asp Phe Gly Glu Gln Gln Arg Arg Arg Glu Val Leu Ala Leu Tyr
945                 950                 955                 960

Arg Trp Thr Gly Asp Gly Ser Gly Leu Ala Leu
                965                 970

<210> SEQ ID NO 31
<211> LENGTH: 907
<212> TYPE: PRT
<213> ORGANISM: Aspergillus terreus
<220> FEATURE:
<221> NAME/KEY: XlnRAterreus
<222> LOCATION: (1)..(907)

<400> SEQUENCE: 31

Met Ala Pro Ser Gln Thr Ile Gly Leu Asp Thr Leu Ala Glu Gly Ser
1               5                   10                  15

Gln Tyr Ser Leu Glu Gln Leu Gln Leu Ser Arg Glu Ala Gly Asn Asp
            20                  25                  30

Ala Ala Thr Ala Thr Ser Ser Thr Ser Leu Arg Ser Ser Ser Phe Ser
        35                  40                  45

Lys Ser Thr Asp Gln Ser Val Ser Asn Pro Ser Gly Asn His His Ser
    50                  55                  60

Asn Asn Gly Pro Pro Ser Asp Phe Lys Ser Ser Gln Arg Asp Pro Leu
65                  70                  75                  80

Ala Glu Ala Arg Ser Ala Ile Arg Lys Asn Ser Thr Ser Ala Pro Val
                85                  90                  95

Arg Arg Arg Ile Ser Arg Ala Cys Asp Gln Cys Asn Gln Leu Arg Thr
            100                 105                 110

Lys Cys Asp Gly Gln His Pro Cys Ala His Cys Ile Glu Phe Gly Leu
        115                 120                 125

Thr Cys Glu Tyr Ala Arg Glu Arg Lys Lys Arg Gly Lys Ala Ser Lys
    130                 135                 140

Lys Asp Leu Ala Ala Ala Ala Ala Ala Ala Ala Gly Ser Thr
145                 150                 155                 160

Ser Ser Ser Thr Ala Asn Asp Gly Gly Pro Met Leu Thr Lys Gly His
                165                 170                 175

Ser Pro Ser Asp Gly Arg Ser Ser His Glu Ile Asn Gly Arg Tyr Asp
            180                 185                 190

Pro Ala Phe Asp Ala Ala Arg Thr Leu Thr Asn Ser Ala Gln Ser Gln
        195                 200                 205

Leu Gln Ser His Ala Asp Val Pro Gly Met Val Gly Met Gln Asn Ser
    210                 215                 220

Gln Gln Pro His Ser Gln Pro Leu Gly Ala Ala Leu Asp Ala Leu
225                 230                 235                 240

His Leu Asn His Phe Ser Ala Leu Asn Glu Ser Asn Arg Pro Gln Met
                245                 250                 255

Ser Val Pro Asp Leu Arg Thr Leu Gln Met Leu His Pro Ser Gly Thr
            260                 265                 270
```

```
Asn Pro Arg Ser Pro Ser Ala Val Leu Pro Ser Gln Gly Leu Asn Ser
            275                 280                 285

Tyr Asn Glu Thr Ala Tyr Ser Leu Met Asn Pro Gln Glu Ser Asn Pro
        290                 295                 300

Ala Ser Met Asn His Phe Arg Leu Gly Ser Ser Ala Glu Asn Gln Pro
305                 310                 315                 320

Pro Ser Phe Leu Gly Leu Ser Pro Pro Ala Gln Ser Pro Gly Trp Leu
                325                 330                 335

Pro Leu Pro Ser Pro Ser Pro Ala Asn Phe Pro Ser Phe Ser Met Asn
                340                 345                 350

Pro Tyr Pro Ser Thr Leu Arg Tyr Pro Val Leu Gln Pro Val Leu Pro
            355                 360                 365

His Ile Ala Ser Ile Ile Pro Gln Ser Leu Ala Cys Asp Leu Leu Asp
        370                 375                 380

Val Tyr Phe Thr Ser Phe Ser Pro Ser His Leu Ser Pro Leu Ser Pro
385                 390                 395                 400

Tyr Val Val Ala Tyr Ile Phe Arg Lys Gln Ser Phe Leu His Pro Thr
                405                 410                 415

Lys Pro Arg Val Cys Ser Pro Gly Leu Leu Ala Ser Met Leu Trp Val
                420                 425                 430

Ala Ala Gln Thr Ser Asp Ala Ala Phe Leu Thr Ser Pro Pro Ser Ala
            435                 440                 445

Arg Gly Arg Val Cys Gln Lys Leu Leu Glu Leu Thr Ile Gly Leu Leu
        450                 455                 460

Arg Pro Leu Ile His Gly Pro Ala Pro Gly Thr Ser Pro Asn Tyr
465                 470                 475                 480

Ala Ala Asn Met Val Ile Asn Gly Val Ala Leu Gly Gly Phe Gly Val
                485                 490                 495

Ser Met Asp Gln Leu Gly Ala Gln Ser Thr Ala Thr Gly Ala Val Asp
            500                 505                 510

Asp Val Ala Thr Tyr Val His Leu Ala Thr Val Val Ser Ala Ser Glu
        515                 520                 525

Tyr Lys Ala Ala Ser Ile Arg Trp Trp Thr Ala Ala Trp Ser Leu Ala
530                 535                 540

Arg Glu Leu Lys Leu Gly Arg Glu Leu Pro Pro Asn Thr Asn Thr Ala
545                 550                 555                 560

Arg Gln Asp Gly Asp Arg Asp Ala Asp Ser Asp Val Asp Met Ser Lys
                565                 570                 575

Arg Asn Leu Pro Ser Leu Val Thr Ser Val Gly His Gly Ser Gly Thr
                580                 585                 590

Pro Leu Asn Val Thr Glu Glu Arg Glu Glu Arg Arg Leu Trp
            595                 600                 605

Trp Leu Leu Tyr Ala Thr Asp Arg His Leu Ala Leu Cys Tyr Asn Gln
        610                 615                 620

Pro Leu Arg Leu Leu Asp Lys Glu Cys Glu Gly Leu Leu Gln Pro Met
625                 630                 635                 640

Asn Asp Asp Leu Trp Gln Ala Gly Asp Phe Gly Ala Val Gly Tyr Arg
                645                 650                 655

Gln Val Gly Pro Pro Ile Glu Cys Ser Gly His Ser Met Phe Gly Tyr
                660                 665                 670

Phe Leu Pro Leu Met Thr Ile Leu Gly Gly Ile Val Asp Leu Gln Gln
            675                 680                 685

Ala Lys Glu His Pro Arg Phe Gly Ile Ala Phe Arg Asn Ser Ser Glu
        690                 695                 700
```

```
Trp Glu His Gln Val Leu Glu Leu Thr Arg Gln Leu Glu Thr Tyr Gly
705                 710                 715                 720

Gln Ser Leu Lys Glu Phe Glu Ser Arg Tyr Thr Ser Ser Leu Ala Leu
            725                 730                 735

Gly Ala Ala Asp Asn Glu Thr Ile Val Asp Gly His Leu Asp His
        740                 745                 750

Val Ser Pro Ser Gly Arg Ser Ser Thr Val Gly Ser Arg Ile Asn
        755                 760                 765

Glu Ser Ile Val His Thr Lys Met Val Ala Tyr Gly Thr His Ile
        770                 775                 780

Met His Val Leu His Ile Leu Leu Ala Gly Lys Trp Asp Pro Ile Asn
785                 790                 795                 800

Leu Leu Glu Asp Gln Asp Leu Trp Ile Ser Ser Glu Ser Phe Ile Thr
            805                 810                 815

Ala Met Gly His Ala Val Gly Ala Ala Asp Ala Ala Asp Ile Leu
        820                 825                 830

Glu Tyr Asp Pro Asp Leu Ser Phe Met Pro Phe Phe Phe Gly Ile Tyr
            835                 840                 845

Leu Leu Gln Gly Ser Phe Leu Leu Leu Ala Ala Asp Lys Leu Gln
        850                 855                 860

Gly Asp Ala Ser Pro Ser Val Val Arg Ala Cys Glu Thr Ile Val Arg
865                 870                 875                 880

Ala His Glu Ala Cys Val Val Thr Leu Asn Thr Glu Tyr Gln Val Arg
                885                 890                 895

Ser His Ser Gln Gly Tyr Ala Pro Arg Leu Tyr
                900                 905

<210> SEQ ID NO 32
<211> LENGTH: 938
<212> TYPE: PRT
<213> ORGANISM: Fusarium oxysporum
<220> FEATURE:
<221> NAME/KEY: XlnRFoxysporm
<222> LOCATION: (1)..(938)

<400> SEQUENCE: 32

Met Leu Ser Asn Pro Leu Gln Arg Phe Ser Pro Tyr Gln Asn Ile Thr
1               5                   10                  15

Ser Ser Asn Ile Ser Pro Asp Gly Asn Val Gln Gln Gly Thr Met Ser
            20                  25                  30

Gly Thr Gly Leu Glu Ser Leu Gly Gln Ser His Gln Tyr Pro Ile Gln
        35                  40                  45

Pro Leu Ser Gln Ala Val Pro Leu Ser Asn Ala His Leu Glu Arg Pro
    50                  55                  60

Gly Pro Gln Val Lys Asn Arg Gln His Pro Tyr Gly Ile His Pro Arg
65                  70                  75                  80

Asn Ala Ser Thr Ser Gly Pro Ile Arg Arg Ile Ser Arg Ala Cys
                85                  90                  95

Asp Gln Cys Asn Gln Leu Arg Thr Lys Cys Asp Gly His Pro Cys
            100                 105                 110

Ala His Cys Ile Glu Phe Gly Leu Gly Cys Glu Tyr Ile Arg Glu Arg
        115                 120                 125

Lys Lys Arg Gly Lys Ala Ser Arg Lys Glu Leu Ala Gln Gln Ala Ala
130                 135                 140

Ala Gln Ala Ala Ala Ala Asn Gly Gln Thr Leu Asp Glu Ser Thr
145                 150                 155                 160
```

```
Ser Glu Asn Gly Gln Ser Gly Asn Lys Gly Leu Asp Ser Ser Asn Met
            165                 170                 175
Val Leu Glu Gln Gln Ser Asn Glu Arg His Pro Ser Thr Ser Ser Lys
            180                 185                 190
Ser Ser Arg Asp Pro Gly Asp Val Met Arg His Thr Gln Gly Leu
        195                 200                 205
Glu Gly Leu Asp Pro Leu Gly Asn Ile Ser Glu Gln Pro His Leu Gly
            210                 215                 220
Arg Ser Ser Leu Asp Gly Glu His Ile Glu Asn Asn Gly Gly Leu Asp
225                 230                 235                 240
Leu Asn Gly Phe Gly Ser Met Ala His Gly Tyr Glu Thr Gln Gly Leu
            245                 250                 255
Glu Gly Pro Val Leu Asn Gly Gln Ser Tyr Ala Ala Asn Gly Arg Gly
            260                 265                 270
Asn Met Pro Gly Tyr Ala Glu Phe Pro Tyr Ser Met Gln Ala Gln Ser
        275                 280                 285
Pro Pro Asn Phe Ala Asn Asn Pro Thr Phe Arg Met Gly Asn Ser Pro
290                 295                 300
Leu Gly Tyr Ser Met Gly Lys Gly Thr Ser Pro Gly Trp Gly Ile Ser
305                 310                 315                 320
Met Ala Ser Pro Pro Gly Gln Tyr Gln Ser Gln Val Pro Ala Pro Ala
            325                 330                 335
Phe Asn Asn Ser Lys Leu Arg Tyr Pro Val Leu Glu Pro Leu Val Pro
            340                 345                 350
Tyr Leu Asn Asn Pro Ile Pro Ile Pro Leu Ala Cys Asp Leu Ile Asp
            355                 360                 365
Leu Tyr Phe Ala Ser Ser Ser Ala Gln Met His Pro Met Ser Pro
        370                 375                 380
Tyr Val Leu Gly Phe Val Phe Arg Lys Arg Tyr Phe Leu Asp Gln Thr
385                 390                 395                 400
Arg Pro Arg Pro Cys Gln Pro Ala Leu Leu Ala Ser Met Leu Trp Val
            405                 410                 415
Ala Ala Gln Thr Ser Asp Ala Pro Phe Leu Ala Ser Thr Pro Ser Ala
            420                 425                 430
Arg Ala Lys Thr Cys Gln Lys Leu Leu Glu Leu Thr Val Tyr Leu Leu
            435                 440                 445
Arg Pro Leu Ile His Thr Ala Pro Ser Asp Ala Pro Ser Pro Val Ala
450                 455                 460
Asp Gly Val Ala Leu Gly Gly Leu Gly Val Ala Met Pro Gly Ser Ile
465                 470                 475                 480
Ser Leu Asp Ala Thr Ser Gly Glu Ser Gly Pro Phe Gly Ala Ala Gly
            485                 490                 495
Ser Leu Asp Asp Val Ile Thr Tyr Ile His Leu Ala Val Val Ser
            500                 505                 510
Ala Ser Glu Tyr Lys Gly Ala Ser Met Arg Trp Trp Thr Ala Ala Trp
            515                 520                 525
Gly Leu Ala Arg Glu Leu Lys Leu Gly Arg Glu Leu Pro Pro Gly Pro
            530                 535                 540
Ser Pro Ala Thr Gln Glu Asn Met Asp Thr Asp Thr Ala Asp Asp Gly
545                 550                 555                 560
Glu Gly Gly Ile Ser Gly Ser Gly Tyr Val Gly Glu Glu Arg Glu
            565                 570                 575
Glu Arg Arg Arg Ile Trp Trp Leu Leu Tyr Ile Val Asp Arg His Leu
```

```
                580                 585                 590
Ala Leu Cys Tyr Asn Arg Pro Leu Phe Leu Asp Ile Glu Cys Gln
            595                 600                 605

Gly Leu Leu Gln Pro Met Asp Asp Ala Arg Trp Gln Ser Gly Asp Phe
        610                 615                 620

Ser Gly His Ser Asn Ser Thr Thr Asp Pro Asn Leu Leu Gly Thr Ser
625                 630                 635                 640

Pro Glu Gly Tyr Gly Ala Asp Met Thr Gln Ala His Gly Pro Gln Tyr
                645                 650                 655

Glu Cys Arg Gly His Ser Ile Phe Gly Tyr Phe Leu Pro Leu Met Thr
            660                 665                 670

Ile Leu Gly Glu Ile Val Asp Leu His His Ala Lys Asn His Pro Arg
        675                 680                 685

Phe Gly Thr Gly Phe Arg Gln Gly His Glu Trp Asn Ala Gln Thr Ala
    690                 695                 700

Glu Ile Thr Arg His Leu Glu Ile Tyr Glu Gln Ser Leu Gln Ala Phe
705                 710                 715                 720

Glu His Lys Asn Leu Pro Arg Pro Ala Glu Arg Val Asp Ala Gln
                725                 730                 735

Asn Glu Gly Asn Glu Arg Ser Gly Val Pro Asp Ala Asn Thr Pro Ser
            740                 745                 750

Ala His Ser Val His Thr Asn Gly Ser Asn Arg Leu Thr Glu Ser Asn
        755                 760                 765

Ile Gln Thr Arg Ile Val Ile Ala Tyr Gly Thr His Val Met His Val
    770                 775                 780

Leu His Ile Leu Leu Ala Gly Lys Trp Asp Pro Ile Asn Leu Leu Asp
785                 790                 795                 800

Asp Glu Asp Leu Trp Ile Ser Ser Gln Gly Phe Ile Thr Ser Thr Ser
                805                 810                 815

His Ala Val Ala Ala Glu Ala Ile Asp Gln Ile Leu Glu Phe Asp
            820                 825                 830

Pro Gly Leu Glu Phe Met Pro Phe Phe Phe Gly Ile Tyr Leu Leu Gln
        835                 840                 845

Gly Ser Phe Leu Leu Leu Ile Ala Asp Lys Leu Gln Ser Glu Ala
    850                 855                 860

Ser Pro Ser Val Ala Lys Ala Cys Glu Thr Ile Val Arg Ala His Glu
865                 870                 875                 880

Ala Cys Val Val Thr Leu Ser Thr Glu Tyr Gln Arg Lys Phe Ser Lys
                885                 890                 895

Val Met Arg Ser Ala Leu Ala Gln Val Arg Gly Arg Val Pro Glu Asp
            900                 905                 910

Leu Gly Glu Gln Gln Gln Arg Arg Glu Leu Leu Ala Val Tyr Arg
        915                 920                 925

Trp Thr Lys Asp Gly Thr Gly Leu Ala Leu
    930                 935

<210> SEQ ID NO 33
<211> LENGTH: 944
<212> TYPE: PRT
<213> ORGANISM: Neurospora crassa
<220> FEATURE:
<221> NAME/KEY: XlnRNcrassa
<222> LOCATION: (1)..(944)

<400> SEQUENCE: 33

Met Leu Ser Asn Pro Leu His Arg Phe Ala Pro Tyr His Ala Met Pro
```

-continued

```
1               5                   10                  15
Ser Pro Thr Leu Leu Ser Gly Gly His Val Thr Ala Ser His Leu His
            20                  25                  30

Ala Ala Gly Leu Asp Thr Met Gly Pro Gly Ser His Tyr Ala Leu Gln
            35                  40                  45

Gln Leu Gln Gln His Val Ser Val His Asn His His Leu Ala Arg Ala
        50                  55                  60

Gly Pro Gln Pro Lys His Arg Gln His Pro Tyr Gly Pro Val Thr Arg
65                  70                  75                  80

Ala Thr Gly Ala Ala Gly Pro Ile Arg Arg Ile Ser Arg Ala Cys
                85                  90                  95

Asp Gln Cys Asn Gln Leu Arg Thr Lys Cys Asp Gly Gln His Pro Cys
                100                 105                 110

Ala His Cys Ile Glu Phe Gly Leu Gly Cys Glu Tyr Ile Arg Glu Arg
            115                 120                 125

Lys Lys Arg Gly Lys Ala Ser Arg Lys Asp Leu Ala Ala Gln Ala Ala
        130                 135                 140

Ala Ala Ala Ala Ala Gln Leu Asn Gly His Lys Asn Pro Ser Gln Ala
145                 150                 155                 160

Gly Glu Asn Asp Gln Ser Pro Pro Asn Arg Thr Glu Ser Thr Thr Ala
                165                 170                 175

Thr Lys Arg Ala Ser Ser Leu Pro Ile Glu His Gln Thr Ser Asn
            180                 185                 190

Asp Lys Thr Met Ser Asp Met Ser Glu Gly Ser Val Arg Ser Gln Arg
                195                 200                 205

Thr Gly Ser Met Asp Ser Ile Asp Leu Gly Ala His Gln Thr His Ile
            210                 215                 220

Ala Ser His Pro Gly Ala Met Asp Arg Asp Leu Glu Ser Pro Ala Ala
225                 230                 235                 240

Leu Asp Leu Ser Tyr Gly Asn Val His Gln Glu Tyr His Arg Gln Gly
                245                 250                 255

Met Gly Ala His Leu Met Asn Gly Ala Ser His His Thr Pro Tyr Gly
                260                 265                 270

Ser Asn Gln Ala Ala Met Ser Asn Tyr Pro Asp Leu Pro Tyr Ala Leu
            275                 280                 285

His Thr Gln Ser Pro Thr Gly Tyr Ser Ala Asn Thr Ser Ser Gly Phe
        290                 295                 300

Arg Ile Gly Ala Ser Pro Leu Ser Ala Tyr Pro Met Ala Gly Gly Ser
305                 310                 315                 320

Thr Ser Pro Gly Trp Met Asn Leu Ala Ser Pro Pro Gln Phe Ala
                325                 330                 335

Gln His Ile Pro Gln Pro Thr Tyr Ser His Ala Gln Leu Arg Tyr Pro
            340                 345                 350

Val Leu Glu Pro Leu Leu Pro His Leu Gly Asn Leu Met Pro Val Ser
        355                 360                 365

Leu Ala Cys Asp Leu Ile Asp Leu Tyr Phe Ala Ser Ser Ser Ala
            370                 375                 380

Gln Met His Pro Met Ser Pro Tyr Val Leu Gly Phe Val Phe Arg Lys
385                 390                 395                 400

Arg Ser Phe Leu His Pro Thr Lys Pro Arg Gln Cys Gln Pro Ala Leu
                405                 410                 415

Leu Ala Ser Met Leu Trp Val Ala Ala Gln Thr Ser Asp Ala Pro Phe
            420                 425                 430
```

```
Leu Thr Ser Val Pro Ser Ala Arg Gly Lys Ile Cys Gln Lys Leu Leu
        435                 440                 445

Glu Leu Thr Val Ser Leu Leu Lys Pro Leu Ile His Thr Pro Ser Glu
    450                 455                 460

Glu Pro Ser Pro Val Ser Ser Pro Ile Val Asp Gly Val Ala Leu Gly
465                 470                 475                 480

Gly Leu Gly Val Ala Leu Pro Gly Ser Ile Ser Met Asp Ala Leu Thr
                485                 490                 495

Gly Glu Thr Gly Ala Phe Gly Ala Ala Gly Thr Leu Asp Asp Val Val
                500                 505                 510

Thr Tyr Ile His Leu Ala Thr Val Val Ser Ala Ser Glu Tyr Lys Gly
            515                 520                 525

Ala Ser Leu Arg Trp Trp Asn Ala Ala Trp Ser Leu Ala Arg Glu Leu
        530                 535                 540

Lys Leu Gly Arg Glu Ile Pro Gln Asn Ser Pro Ser Met Gln Asn Ser
545                 550                 555                 560

Gly Ser Glu Leu Asp Gly Glu Met Gly Asn Ile Pro Gly Met Ile Thr
                565                 570                 575

Glu Glu Glu Arg Glu Glu Arg Arg Ile Trp Trp Leu Val Tyr Ile
                580                 585                 590

Val Asp Arg His Leu Ala Leu Cys Tyr Asn Arg Pro Leu Phe Leu Leu
            595                 600                 605

Asp Ile Glu Cys Asp Gly Leu Leu Gln Pro Met Asp Asp Thr Asp Tyr
        610                 615                 620

Gln Asn Gly Asn Phe Tyr Ala Tyr Thr Asp Pro Asn Val Leu Ala Ser
625                 630                 635                 640

Asp Pro Asn Thr Pro Ala Ala Arg His Arg Gly Pro Ser Phe Val Cys
                645                 650                 655

Thr Gly His Ser Ile Phe Gly Tyr Phe Leu Pro Leu Met Thr Ile Leu
                660                 665                 670

Gly Glu Ile Val Asp Leu His His Ala Arg Asn His Pro Arg Phe Gly
            675                 680                 685

Val Gly Phe Arg Ser Ser Arg Glu Trp Asp Asp Gln Thr Ala Glu Ile
        690                 695                 700

Thr Arg His Leu Glu Ile Tyr Glu Glu Ser Ile Lys Arg Phe Glu His
705                 710                 715                 720

Arg Asn Leu Ser Leu Ser Ala Gln Ala Gln Ala Ala Asp Glu Lys Ala
                725                 730                 735

Ala Glu Ala Ala Gly Val Pro Thr Ala Asn Asp Val Pro His Asp Ala
                740                 745                 750

Gly Thr Pro Ser Val Gln Ser Val His Ser Val His Thr Thr Ser Ser
            755                 760                 765

Arg Met Thr Glu Ser Asp Ile Gln Thr Arg Ile Val Met Ala Tyr Gly
        770                 775                 780

Thr His Val Met His Val Leu His Ile Leu Leu Thr Gly Lys Trp Asp
785                 790                 795                 800

Pro Ile Asn Leu Leu Asp Asp Asn Asp Leu Trp Ile Ser Ser Gln Gly
                805                 810                 815

Phe Ile Thr Ala Thr Gly His Ala Val Ser Ala Glu Ala Ile Ser
                820                 825                 830

Asn Ile Leu Glu Tyr Asp Pro Gly Leu Glu Phe Met Pro Phe Phe Phe
            835                 840                 845

Gly Ile Tyr Leu Leu Gln Gly Ser Phe Leu Leu Leu Ile Ala Asp
        850                 855                 860
```

```
Lys Leu Gln Val Glu Ala Ser Pro Ser Val Val Lys Ala Cys Glu Thr
865                 870                 875                 880

Ile Ile Arg Ala His Glu Ala Cys Val Val Thr Leu Asn Thr Glu Tyr
                885                 890                 895

Gln Arg Asn Phe Ser Arg Val Met Arg Ser Ala Leu Ala Gln Val Arg
            900                 905                 910

Gly Arg Val Pro Glu Asp Leu Gly Glu Gln His Gln Arg Arg Arg Glu
        915                 920                 925

Leu Leu Ala Leu Tyr Arg Trp Thr Gly Asp Gly Thr Gly Leu Ala Leu
    930                 935                 940
```

<210> SEQ ID NO 34
<211> LENGTH: 958
<212> TYPE: PRT
<213> ORGANISM: Penicillum canescens
<220> FEATURE:
<221> NAME/KEY: XlnRPcanescens
<222> LOCATION: (1)..(958)

<400> SEQUENCE: 34

```
Met Ser Thr Thr Ser Thr Ser Leu Gln Ser Phe Ala Asn Ser Tyr Ser
1               5                   10                  15

Pro Phe Ser Ser Arg Pro Gln Pro Asn Arg Met Ala Gln Ser Gln Thr
            20                  25                  30

Pro Gly Leu Asp Thr Leu Ala Glu Gly Ser Gln Tyr Ala Leu Glu Gln
        35                  40                  45

Leu Gln Leu Ala Arg Gln Ala Ser Ala Ser Asn Pro Pro Thr Asp Ser
    50                  55                  60

Glu Gly Lys Pro Val Ser Glu Ser Glu Ala Leu Glu Pro Pro Pro Tyr
65                  70                  75                  80

Arg Glu Gln Asn Gly Thr His Ser Gly Ser Lys Ser Ser Ser Gln Gln
                85                  90                  95

His Asp Pro Leu Val Asp Ala Arg Ser Ala Ile Arg Lys Asn Ser Thr
            100                 105                 110

Ala Thr Ala Val Arg Arg Ile Ser Arg Ala Cys Asp Gln Cys Asn
        115                 120                 125

Gln Leu Arg Thr Lys Cys Asp Gly Gln Pro Cys Ala His Cys Ile
    130                 135                 140

Glu Phe Gly Leu Ser Cys Glu Tyr Ala Arg Glu Arg Lys Lys Arg Gly
145                 150                 155                 160

Lys Ala Ser Lys Lys Asp Leu Ala Ala Ala Ala Val Ala Thr Ser
                165                 170                 175

Thr Ser Asp Lys Gly Leu Gln Asp Gly Gly Ser Val His Gly Asn Ser
            180                 185                 190

Pro Asn Gly His Ser Ser His Glu Val Ser Met Pro Tyr Asp Pro Ala
        195                 200                 205

Phe Asp Ala Ala Arg Ala Val Pro Glu Ser Ala Gln Pro Pro Leu Arg
    210                 215                 220

Asn His Ser Val Pro Gly Ile Ser Arg Ile Gln Gln Asn Asn His Ser
225                 230                 235                 240

Ala Ser Gly His Pro Gln Gln Gln Val Gly Ser Gly Ile Asp Ser Ile
                245                 250                 255

Ser Leu Asn Tyr Gly Asn Val Pro Asp Ser Asn Arg Pro Ser Met Ser
            260                 265                 270

Val Pro Asp Leu Arg Ser Leu Gln Met Met Gln Asn Gly Asn Pro
    275                 280                 285
```

-continued

Arg Ser Pro Ala Ala Met Ile His Ser Gln Gly Phe Gly Ser Gly Tyr
    290                 295                 300

His Asp Gly Ala Tyr Pro Leu Met Asn Ser His Asp Thr Asn Ala Asn
305                 310                 315                 320

Ser Ile Gly Gln Phe Arg Leu Gly Gly Ser Ala Glu Asn Pro Ser Ala
                325                 330                 335

Ser Phe Leu Gly Gly Phe Ser Pro Pro Ala Gln Ser Pro Ser Trp Leu
            340                 345                 350

Pro Leu Pro Ser Pro Ser Pro Ala Asn Phe Pro Ser Phe Ser Met Ala
        355                 360                 365

Pro Phe Ala Ser Thr Leu Arg Tyr Pro Val Leu Gln Pro Val Leu Pro
370                 375                 380

His Ile Ala Ser Ile Ile Pro Gln Ser Leu Ala Cys Asp Leu Leu Asp
385                 390                 395                 400

Val Tyr Phe Thr Ser Ser Ser Ser His Met Ser Pro Leu Ser Pro
                405                 410                 415

Tyr Val Val Gly Phe Val Phe Arg Lys Gln Ser Phe Leu His Pro Thr
            420                 425                 430

Lys Pro Arg Val Cys Ser Pro Gly Leu Leu Ala Ser Met Leu Trp Val
        435                 440                 445

Ala Ala Gln Thr Ser Glu Ala Ala Phe Leu Thr Ser Pro Pro Ser Ala
450                 455                 460

Arg Gly Arg Val Cys Gln Lys Leu Leu Glu Leu Thr Ile Gly Leu Leu
465                 470                 475                 480

Arg Pro Leu Ile His Gly Pro Ala Thr Gly Glu Ala Ser Pro Asn Tyr
                485                 490                 495

Ala Ala Asn Met Val Ile Asn Gly Val Ala Leu Gly Gly Phe Gly Val
            500                 505                 510

Ser Met Asp Gln Leu Gly Ala Gln Ser Ser Ala Thr Gly Ala Val Asp
        515                 520                 525

Asp Val Ala Thr Tyr Val His Leu Ala Thr Val Val Ser Ala Ser Glu
530                 535                 540

Tyr Lys Ala Ala Ser Met Arg Trp Trp Thr Ala Ala Trp Ser Leu Ala
545                 550                 555                 560

Arg Glu Leu Lys Leu Gly Arg Glu Leu Pro Pro Asn Thr Asn Arg Gln
                565                 570                 575

Asp Gly Glu Leu Glu Gly Glu Ser Glu Met Asp Leu Asn Gly Asn Lys
            580                 585                 590

Arg Gln Thr Thr Ser Leu Leu Asn Ser Met Gly His Gly Pro Gly Ser
        595                 600                 605

Ser Ser Ile Asn Leu Ser Glu Glu Glu Arg Glu Arg Arg Ile
610                 615                 620

Trp Trp Leu Leu Tyr Val Met Asp Arg His Leu Ala Leu Cys Tyr Asn
625                 630                 635                 640

Arg Pro Leu Thr Leu Leu Asp Lys Glu Cys Glu Gly Leu Leu Gln Pro
                645                 650                 655

Met Asn Asp Asp Leu Trp Gln Ala Gly Asp Phe Ser Ala Ala Ser Tyr
            660                 665                 670

Arg Arg Ala Gly Pro Ala Phe Glu Cys Thr Ser His Ser Thr Phe Gly
        675                 680                 685

Tyr Phe Leu Pro Leu Met Ser Ile Leu Gly Glu Ile Val Asp Leu Gln
690                 695                 700

His Ala Arg Asn His Pro Arg Phe Gly Leu His Phe Arg Asn Ser Gly

```
705                 710                 715                 720

Glu Trp Glu Ser Gln Ala Met Glu Ile Thr Arg Gln Leu Asp Val Tyr
                725                 730                 735

Ala Gln Ser Leu Lys Glu Phe Glu Ala Arg Tyr Thr Ser Ser Leu Ala
            740                 745                 750

Leu Gly Gly Asp Asn Asp Thr Ala Met Glu Gly Ala His Ile Asn His
        755                 760                 765

Val Ser Pro Ser Gly Arg Ser Asn Ser Ser Thr Val Gly Ser His Val
    770                 775                 780

Ser Glu Ser Ile Val His Thr Arg Met Val Val Ala Tyr Gly Thr His
785                 790                 795                 800
Ile Met His Val Leu His Ile Leu Leu Ala Gly Lys Trp Asp Pro Ile
                805                 810                 815
Asn Leu Leu Asp Asp Asn Asp Leu Trp Ile Ser Ser Asp Ser Phe Ile
            820                 825                 830

Thr Ala Met Gly His Ala Val Ser Ala Ala Glu Ala Ala Ser Asp Ile
        835                 840                 845

Leu Glu Tyr Asp Pro Asp Leu Ser Phe Met Pro Phe Phe Phe Gly Ile
    850                 855                 860

Tyr Leu Leu Gln Gly Ser Phe Leu Leu Leu Leu Thr Ala Asp Lys Leu
865                 870                 875                 880
Gln Gly Asp Ala Ser Pro Ser Val Val Arg Ala Cys Glu Thr Ile Val
                885                 890                 895

Arg Ala His Glu Ala Cys Val Val Thr Leu Asn Thr Glu Tyr Gln Arg
            900                 905                 910

Thr Phe Arg Lys Val Met Arg Ser Ala Leu Ala Gln Val Arg Gly Arg
        915                 920                 925

Val Pro Glu Asp Phe Gly Glu Gln Gln Gln Arg Arg Arg Glu Val Leu
    930                 935                 940

Ala Leu Tyr Arg Trp Ser Gly Asp Gly Ser Gly Leu Ala Leu
945                 950                 955

<210> SEQ ID NO 35
<211> LENGTH: 925
<212> TYPE: PRT
<213> ORGANISM: Pyrenophora tritici
<220> FEATURE:
<221> NAME/KEY: XlnRPtritici
<222> LOCATION: (1)..(925)

<400> SEQUENCE: 35

Met Leu Ser Thr Asn Leu His Gln Tyr Pro Ser Ala Phe Ser His Leu
1               5                   10                  15

Pro Ala Pro Asn Met Val Glu His Gln His Gln His His His Leu Ala
            20                  25                  30

Ala Pro His Met Gly His Ser Pro Leu Asp Thr Leu Ala His Thr Ser
        35                  40                  45

Gln Tyr Ala Ala Leu Gln Phe His Gln Asn Arg His Val Leu Pro Ser
    50                  55                  60

Gly Lys Ser Leu Val Lys Asn His Arg Leu Pro Tyr Ala Ser Gly Pro
65                  70                  75                  80

Leu Ala Pro Arg Asn His Arg Asp Met Leu Gln Glu Arg Ser Gly Arg
                85                  90                  95

Ala Asn Ser Thr Ser Gly Pro Cys Ala His Cys Ile Glu Phe Gly Leu
            100                 105                 110

Thr Cys Glu Tyr Ile Arg Glu Arg Lys Lys Arg Gly Lys Ala Ser Arg
```

```
            115                 120                 125
Lys Asp Ile Ala Gln Gln Gln Ala Ala Ala Ala Gly Asn Ser
        130                 135                 140
Ala Pro Lys Ser Glu Glu Ser Ser Thr Pro Glu Ala Pro Lys Val
145                 150                 155                 160
Pro Gln Ser Lys Gln Ala Ala Lys Ser Pro Lys Leu Pro Glu Gly Gln
                165                 170                 175
Arg Ala Leu Pro Glu Leu Pro Ser Arg Ser Ala Ser Ile Ala Thr Thr
                180                 185                 190
Arg Pro Asp Met Asp Thr Thr Pro Ile Tyr Pro Asn Arg Thr Met Ser
                195                 200                 205
Leu Ser Ala Ile Asp Asn Ile Pro Glu Val Asp Met His His Gln Met
                210                 215                 220
Ser Glu Ser Met His Pro Met Gln Pro Met Gln Pro His Arg Ile Arg
225                 230                 235                 240
Thr Asp Gly Leu Pro Met His Asn Pro Asn Pro Met Ala Glu Tyr Thr
                245                 250                 255
Ser Met Glu Glu Tyr His Arg Asn Leu Ala Tyr Gln Ser Pro Leu Gln
                260                 265                 270
Met Met Gln Pro Gly Met His Pro Gly Val Ser Ser His Asp Arg Gly
                275                 280                 285
Ile Glu Tyr Ser Asp Ser Pro Tyr Ser Met Met Ser Pro Gln Ser Ala
                290                 295                 300
His Gly Gln Val Pro Ser Asn Pro Phe Arg Ile Ala Glu Glu Gln Ser
305                 310                 315                 320
Asn Met Gly Tyr Met Ala Gln Ser Pro Val Gly Ala Ser Pro Gly Trp
                325                 330                 335
Met Ile Pro Ser Pro Ser Thr Thr Met Tyr Ser Gly Ala Pro His Gln
                340                 345                 350
Thr Pro Ser Gln Gln Leu Arg Tyr Pro Val Leu Gln Pro Leu Val Pro
                355                 360                 365
His Ile Ala Asn Met Met Pro Leu Ser Leu Ala Cys Asp Leu Leu Glu
                370                 375                 380
Leu Tyr Phe Glu Ser Ser Ser Ala Phe Met Gln Pro Val Ser Pro
385                 390                 395                 400
Tyr Val Leu Gly Tyr Val Phe Arg Lys Arg Ser Phe Leu Arg Thr Asn
                405                 410                 415
Ser Pro Arg Val Cys Ser Pro Ala Leu Leu Ala Ser Met Leu Trp Ile
                420                 425                 430
Gly Cys Leu Thr Ser Glu Ser Pro Tyr Leu Ser Ser Pro Ser Ala
                435                 440                 445
Arg Ser Gln Leu Ser Glu Arg Leu Ile Asn Leu Thr Ile Ser Leu Leu
                450                 455                 460
Lys Pro Leu Val His Gln Thr Pro Gly Asp Pro Asp Cys Ser Pro Thr
465                 470                 475                 480
Ala Phe Ala Asn Gly Gly Met Val Asn Gly Val Thr Met Gly Ala Phe
                485                 490                 495
Gly Met Pro Thr His Asp Ser Glu Ile Gly Leu Pro Gly Ala Pro Gly
                500                 505                 510
Gly Leu Asp Asp Val Ala Thr Tyr Met His Leu Ala Ile Val Ile Ser
                515                 520                 525
Ala Ser Glu Tyr Lys Ala Ala Ser Leu Arg Trp Trp Asn Ala Ala Trp
530                 535                 540
```

Ser Leu Ala Arg Glu Leu Lys Leu Gly Lys Glu Val Pro Val Thr Pro
545                 550                 555                 560

Pro Pro Glu Thr Asn Asp Asp Ala Pro Val Asp Val Asp Ala Gly
            565                 570                 575

His Thr Gly Arg Arg Tyr Pro Thr Gly Gln Asn Thr Pro Val Asp Tyr
        580                 585                 590

Thr Glu Glu Gln Arg Glu Arg Arg Ile Trp Trp Leu Leu Phe
        595                 600                 605

Thr Val Asp Arg His Leu Ala Leu Cys Tyr Asn Arg Pro Leu Ser Leu
        610                 615                 620

Leu Asp Val Glu Cys Ser Gly Leu Met Gln Pro Leu Glu Asp Asn Val
625                 630                 635                 640

Trp Gln Ser Gly Glu Phe Phe Glu Val Ser Ala Gln Pro Phe Ser Asp
            645                 650                 655

Ser Thr Phe Arg Arg Arg Gly Pro Ala Phe Glu Cys Thr Gly His Ser
            660                 665                 670

Ile Phe Gly Phe Phe Leu Pro Leu Met Thr Ile Leu Gly Glu Ile Thr
            675                 680                 685

Asp Leu Tyr His Ala Arg Asn His Pro Arg Phe Gly Thr Lys Thr Asp
            690                 695                 700

Trp Asp Asp His Ala Arg Glu Ile Ser Gln Gln Leu Asp Ala Tyr Gly
705                 710                 715                 720

Arg Ser Leu Gln Glu Leu Arg Asn Arg Ala Val Asn Glu Ala Asn Ala
            725                 730                 735

Glu Glu Pro Val His Pro Gly Thr Pro Ser Val Gln Ser Val Asn Ser
            740                 745                 750

Thr Ile Ser Arg Ala Gln Glu Ser Leu Met His Ala Lys Ile Val Glu
            755                 760                 765

Ala Tyr Gly Thr His Leu Met His Thr Leu His Ile Leu Leu Asn Gly
            770                 775                 780

Lys Trp Asp Pro Ile Ser Leu Leu Asp Asp Asn Asp Leu Trp Ile Ser
785                 790                 795                 800

Ser Gln Ser Phe Val Glu Ala Thr Gly His Ala Val Ser Ala Ala Glu
            805                 810                 815

Ala Leu Asn Glu Ile Leu Glu Tyr Asp Pro Asp Leu Ser Phe Met Pro
            820                 825                 830

Phe Phe Phe Gly Ile Tyr Leu Leu Gln Gly Ser Phe Leu Leu Leu Leu
            835                 840                 845

Ile Ala Asp Lys Leu Gln Gly Asp Ala Asn Pro Asn Ile Val Arg Ala
            850                 855                 860

Cys Glu Val Ile Val Arg Ala His Glu Ala Cys Ile Val Thr Leu Asn
865                 870                 875                 880

Thr Glu Tyr Gln Arg Asn Phe Arg Lys Val Met Arg Ser Thr Leu Gln
            885                 890                 895

Gln Val Arg Gly Arg Gly Met Asp Glu His Ala Glu Leu Ala Gln Gln
            900                 905                 910

Arg Pro Gln Gly Asn Val Glu Pro Leu Pro Leu Asp Trp
            915                 920                 925